United States Patent
Müller et al.

[11] Patent Number: 5,977,399
[45] Date of Patent: Nov. 2, 1999

[54] IMINOOXYMETHYLENEANILIDES, PREPARATION THEREOF AND INTERMEDIATES THEREFOR, AND COMPOSITIONS CONTAINING THEM

[75] Inventors: Bernd Müller; Ruth Müller, both of Frankenthal; Herbert Bayer; Hubert Sauter, both of Mannheim; Franz Röhl, Schifferstadt; Eberhard Ammermann, Heppenheim; Gisela Lorenz, Hambach; Norbert Götz, Worms, all of Germany

[73] Assignee: BASF Aktiengesellschaft, Ludwighshafen, Germany

[21] Appl. No.: 08/836,396

[22] PCT Filed: Nov. 10, 1995

[86] PCT No.: PCT/EP95/04428

§ 371 Date: May 6, 1997

§ 102(e) Date: May 6, 1997

[87] PCT Pub. No.: WO96/16030

PCT Pub. Date: May 30, 1996

[30] Foreign Application Priority Data

Nov. 23, 1994 [DE] Germany ............... 44 41 674

[51] Int. Cl.⁶ ................................. C07C 26/00
[52] U.S. Cl. .................. 560/29; 562/621; 564/170; 564/52
[58] Field of Search ............... 560/29; 562/621; 564/170, 52

[56] References Cited
FOREIGN PATENT DOCUMENTS

| | | |
|---|---|---|
| 2127110 | 8/1993 | Canada . |
| 619 301 | 10/1994 | European Pat. Off. . |
| 93/00104 | 8/1993 | WIPO . |

*Primary Examiner*—Paul J. Killos
*Attorney, Agent, or Firm*—Keil & Weinkauf

[57] ABSTRACT

Iminooxymethyleneanilides of the formula I

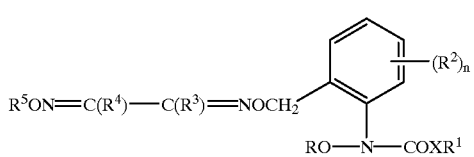

where the substituents and the index have the following meanings:

R is hydrogen,
  unsubst. or subst. alkyl, alkenyl, alkynyl, cycloalkyl, cycloalkenyl, cycloalkynyl, alkylcarbonyl or alkoxycarbonyl;

$R^1$ is alkyl, alkenyl, alkynyl, cycloalkyl or cycloalkenyl and in the case where X is $NR^a$, additionally hydrogen;

X is a direct bond, O or $NR^a$;

$R^a$ is hydrogen, alkyl, alkenyl, alkynyl, cycloalkyl or cycloalkenyl;

$R^2$ is cyano, nitro, trifluoromethyl, halogen, alkyl or alkoxy;

n is 0, 1 or 2;

$R^3$ is hydrogen, hydroxyl, cyano, cyclopropyl, trifluoromethyl, halogen, alkyl, alkoxy or alkylthio;

$R^4$ is hydrogen, hydroxyl, halogen, alkyl, haloalkyl, alkoxy, alkylthio,
  unsubstituted or substituted cycloalkyl, heterocyclyl, aryl, arylalkyl, hetaryl or hetarylalkyl;

$R^5$ is hydrogen,
  unsubstituted or substituted alkyl, cycloalkyl, alkenyl, alkynyl, alkylcarbonyl, alkenylcarbonyl, alkynylcarbonyl or alkylsulfonyl,
  unsubstituted or substituted aryl, hetaryl, arylcarbonyl, hetarylcarbonyl, arylsulfonyl or hetarylsulfonyl;

and their salts, processes and intermediates for their preparation and compositions containing them.

20 Claims, No Drawings

IMINOOXYMETHYLENEANILIDES, PREPARATION THEREOF AND INTERMEDIATES THEREFOR, AND COMPOSITIONS CONTAINING THEM

The present invention relates to iminooxymethyleneanilides of the formula I

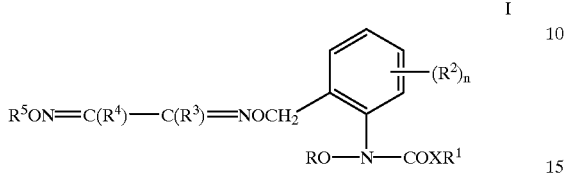

where the substituents and the index have the following meanings:

R is hydrogen,
unsubst. or subst. alkyl, alkenyl, alkynyl, cycloalkyl, cycloalkenyl, cycloalkynyl, alkylcarbonyl or alkoxycarbonyl;

$R^1$ is alkyl, alkenyl, alkynyl, cycloalkyl or cycloalkenyl and in the case where X is $NR^a$, additionally hydrogen;

X is a direct bond, O or $NR^a$;

$R^a$ is hydrogen, alkyl, alkenyl, alkynyl, cycloalkyl or cycloalkenyl;

$R^2$ is cyano, nitro, trifluoromethyl, halogen, $C_1$–$C_4$-alkyl or $C_1$–$C_4$-alkoxy;

n is 0, 1 or 2, it being possible for the radicals $R^2$ to be different if n is 2;

$R^3$ is hydrogen, hydroxyl, cyano, cyclopropyl, trifluoromethyl, halogen, $C_1$–$C_6$-alkyl, $C_1$–$C_6$-alkoxy or $C_1$–$C_6$-alkylthio;

$R^4$ is hydrogen, cyano, nitro, hydroxyl, amino, halogen, $C_1$–$C_6$-alkyl, $C_1$–$C_6$-alkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkenylthio, $C_2$–$C_6$-alkenylamino, n-$C_2$–$C_6$-alkenyl-n-$C_1$–$C_6$-alkylamino, $C_2$–$C_6$-alkynyl, $C_2$–$C_6$-alkynyloxy, $C_2$–$C_6$-alkynylthio, $C_2$–$C_6$-alkynylamino, N-$C_2$–$C_6$-alkynyl-N-$C_1$–$C_6$-alkylamino, it being possible for the hydrocarbon radicals of these groups to be partially or completely halogenated or to carry one to three of the following radicals: cyano, nitro, hydroxyl, mercapto, amino, carboxyl, aminocarbonyl, aminothiocarbonyl, halogen, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio, hetaryl-$C_1$–$C_4$-alkylthio, it being possible for the cyclic radicals in turn to be partially or completely halogenated and/or to carry one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C(=NOR^6)$—$A_n$—[7];

$C_3$–$C_6$-cycloalkyl, $C_3$–$C_6$-cycloalkyloxy, $C_3$–$C_6$-cycloalkylthio, $C_3$–$C_6$-cycloalkylamino, N-$C_3$–$C_6$-cycloalkyl-N-$C_1$–$C_6$-alkylamino, $C_3$–$C_6$-cycloalkenyl, $C_3$–$C_6$-cycloalkenyloxy, $C_3$–$C_6$-cycloalkenylthio, $C_3$–$C_6$-cycloalkenylamino, N-$C_3$–$C_6$-cycloalkenyl-N-$C_1$–$C_6$-alkylamino, heterocyclyl, heterocyclyloxy, heterocyclylthio, heterocyclylamino, N-heterocyclyl-N-$C_1$–$C_6$-alkylamino, aryl, aryloxy, arylthio, arylamino, N-aryl-N-$C_1$–$C_6$-alkylamino, hetaryl, hetaryloxy, hetarylthio, hetarylamino, N-hetaryl-N-$C_1$–$C_6$-alkylamino, it being possible for the cyclic radicals to be partially or completely halogenated or to carry one to three of the following groups: cyano, nitro, hydroxy, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl and hetaryloxy;

$R^5$ is hydrogen, $C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_3$–$C_{10}$-alkynylcarbonyl or $C_1$–$C_{10}$-alkylsulfonyl, it being possible for these radicals to be partially or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy and hetarylthio, it being possible for the cyclic groups in turn to be partially or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^6)$—$A_n$—$R^7$;

aryl, arylcarbonyl, arylsulfonyl, hetaryl, hetarylcarbonyl or hetarylsulfonyl, it being possible for these radicals to be partially or completely halogenated or to carry one to three of the following groups: cyano, nitro, hydroxy, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy or C(=NOR$^6$)—A$_n$—R$^7$;

A being oxygen, sulfur or nitrogen and the nitrogen carrying hydrogen or $C_1$–$C_6$-alkyl;

m being 0 or 1;

R$^6$ being hydrogen, $C_1$–$C_6$-alkyl, $C_2$–$C_6$-alkenyl or $C_2$–$C_6$-alkynyl and R$^7$ being hydrogen, $C_1$–$C_6$-alkyl, $C_2$–$C_6$-alkenyl or $C_2$–$C_6$-alkynyl, and their salts.

The invention additionally relates to processes and intermediates for preparing these compounds, and compositions containing them for controlling animal pests and harmful fungi.

Anilides are disclosed in the literature as fungicides (WO-A 93/15 046).

It is an object of the present invention to provide novel compounds having an improved action.

We have found that this object is achieved by the iminooxymethyleneanilides I defined at the beginning. We have additionally found processes and intermediates for their preparation, and compositions containing them for controlling animal pests and harmful fungi and their use in this context.

The compounds I are obtainable in various ways by processes known per se in the literature.

Basically, it is insignificant in the synthesis of the compounds I whether the group —N(OR)—COXR$^1$ or the group —CH$_2$ON=C(R$^3$)—C(R$^4$)=NOR$^5$ is synthesized first.

The synthesis of the group —N(OR)—COXR$^1$ is known, for example, from the literature cited at the beginning. In general, the synthesis can be carried out starting from compounds of the formula XA

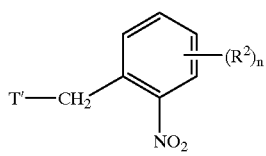

XA where T' is hydrogen or a group O=C(R$^4$)—C(R$^3$)=NO—, HON=C(R$^4$)—C(R$^3$)=NO— or R$^5$ON=C(R$^4$)—C(R$^3$)=NO—.

Compounds XB where T' is not hydrogen can be prepared according to the processes described in the following in items 1 to 6.

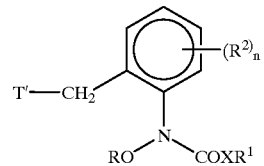

XB

The manner of synthesis of the —CH$_2$ON=C(R$^3$)—C(R$^4$)=NOR$^5$ side chain depends essentially on the nature of the substituents R$^3$ and R$^4$.

1. In the case where R$^3$ and R$^4$ independently of one another are hydrogen, one of the C-organic radicals indicated or hydroxyl or alkoxy, a procedure is in general used in the synthesis of the group —CH$_2$ON=C(R$^3$)—C(R$^4$)=NOR$^5$ in which a benzyl derivative of the formula II is reacted with an oxime of the formula III.

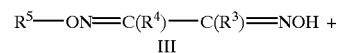

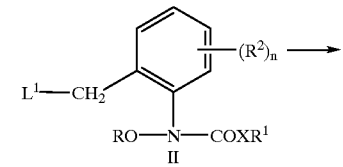

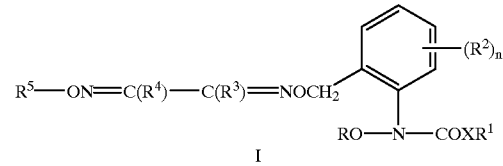

L$^1$ in the formula II is a nucleophilically replaceable leaving group, eg. a halogen or sulfonate group, preferably chlorine, bromine, iodine, mesylate, tosylate or triflate.

The reaction is carried out in a manner known per se in an inert organic solvent in the presence of a base, eg. sodium hydride, potassium hydroxide, potassium carbonate or triethylamine according to the methods described in Houben-Weyl, Vol. E 14b, p. 370ff and Houben-Weyl, Vol. 10/1, p. 1189ff.

The oxime III needed is obtained by reaction of a corresponding dioxime IV with a nucleophilically substituted reagent VI

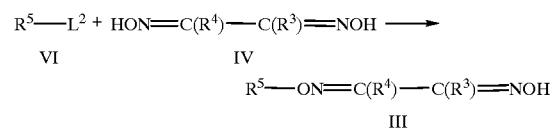

L$^2$ in the formula VI is a nucleophilically replaceable leaving group, eg. a halogen or sulfonate group, preferably chlorine, bromine, iodine, mesylate, tosylate or triflate.

The reaction is carried out in a manner known per se in an inert organic solvent in the presence of a base, eg. potassium carbonate, potassium hydroxide, sodium hydride, pyridine or triethylamine according to the methods described. in Houben-Weyl, Vol. E 14b, p.

307ff, p. 370ff and p. 385ff; Houben-Weyl, Vol. 10/4, p. 55ff, p. 180ff and p. 217ff; Houben-Weyl, Vol. E 5, p. 780ff.

1.1 Alternatively, the compounds I can also be obtained by first converting the benzyl derivative II into a corresponding benzyloxime of the formula V using the dioxime derivative IV, V then being reacted with the nucleophilically substituted reagent VI to give I.

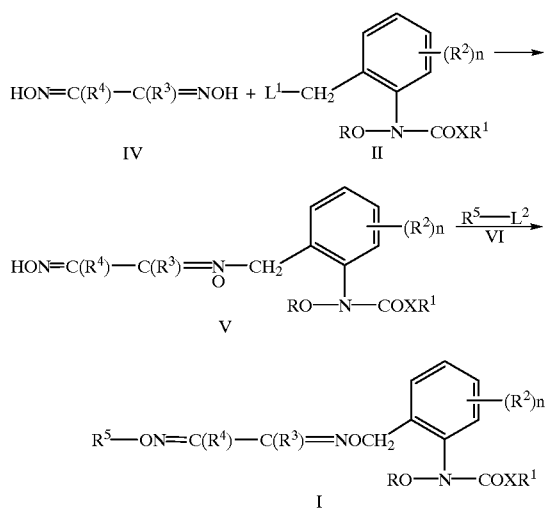

The reaction is carried out in a manner known per se in an inert organic solvent in the presence of a base, eg. potassium carbonate, potassium hydroxide, sodium hydride, pyridine or triethylamine according to the methods described in Houben-Weyl, Vol. 10/1, p. 1189ff; Houben-Weyl, Vol. E 14b, p. 307ff, p. 370ff and p. 385ff; Houben-Weyl, Vol. 10/4, p. 55ff, p. 180ff and p. 217ff; Houben-Weyl, Vol. E 5, p. 780ff.

1.2 In a similar manner, it is likewise possible to prepare the required oxime of the formula III from a ketooxime [sic] VII by reaction with a hydroxylamine IXa or its salt IXb.

$$\left\{\begin{array}{c} R^5\text{—}ONH_2 \\ IXa \\ or \\ R^5\text{—}ONH_3^{\oplus}Q^{\ominus} \\ IXb \end{array}\right\} + O{=}C(R^4)\text{—}C(R^3){=}NOH \longrightarrow \text{VII}$$

$$R^5\text{—}ON{=}C(R^4)\text{—}C(R^3){=}NOH$$
III $Q^{\ominus}$ in the formula IXb is the anion of an acid, in particular an inorganic acid, eg. halide such as chloride.

The reaction is carried out in a manner known per se in an inert organic solvent according to the methods described in EP-A 513 580; Houben-Weyl, Vol. 10/4, p. 73ff; Houben-Weyl, Vol. E 14b, p. 369ff and p. 385ff.

1.3 Alternatively, the compounds I can also be obtained by first converting the benzyl derivative II into a corresponding benzylketoxime of the formula VIII using the ketooxime [sic] derivative VII, VIII then being reacted with the hydroxylamine IXa or its salt IXb to give I.

The reaction is carried out in a manner known per se in an inert organic solvent according to the methods described in Houben-Weyl, Vol. E 14b, p. 369ff; Houben-Weyl, Vol. 10/1, p. 1189ff and Houben-Weyl, Vol. 10/4, p. 73ff or EP-A 513 580.

1.4 A further possibility of preparing the compounds I is the reaction of the benzyl derivative II with N-hydroxyphthalimide and subsequent hydrazinolysis to give the benzylhydroxylamine IIa and the further reaction of IIa with a carbonyl compound X.

The reaction is carried out in a manner known per se in an inert organic solvent according to the methods described in EP-A 463 488, DE-Appl. No. 42 28 867.3.

The required carbonyl compound X is obtained by reaction of a corresponding oxime ketone VIIa with a nucleophilically substituted reagent VI

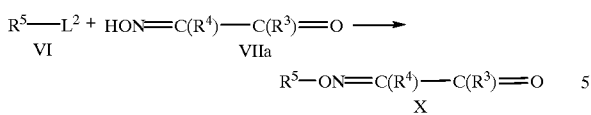

or by reaction of a corresponding diketone XI with a hydroxylamine IXa or its salt IXb

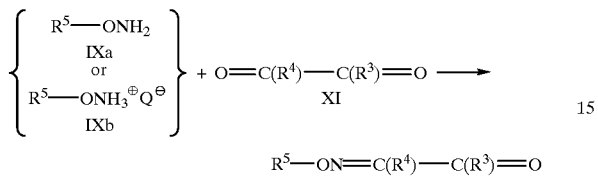

The reactions are carried out in a manner known per se in an inert organic solvent according to the methods described in EP-A 513 580, Houben-Weyl, Vol. 10/4, p. 55ff, p. 73ff, p. 180ff and p. 217ff; Houben-Weyl, Vol. E 14b, p. 307ff and 369ff, Houben-Weyl, Vol. E 5, p. 780ff.

1.5 Correspondingly, the compounds I can also be obtained by first converting the benzylhydroxylamine IIa into the corresponding benzyloxime of the formula V using the oxime ketone VIIa, V then being reacted with the nucleophilically substituted reagent VI as described above to give I.

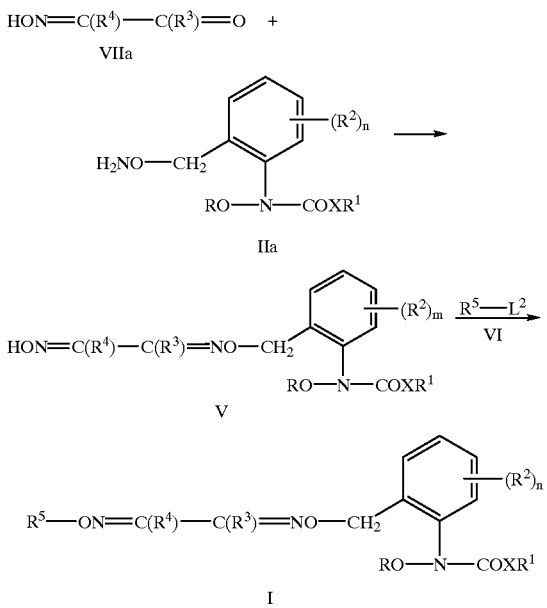

1.6 In a similar manner, the compounds I can likewise be prepared by first converting the benzylhydroxylamine IIa into the benzyloxime of the formula VIII using the diketone of the formula XI and then reacting VIII with the hydroxylamine IXa or its salt IXb as described above to give I.

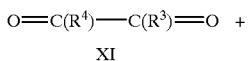

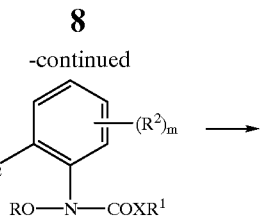

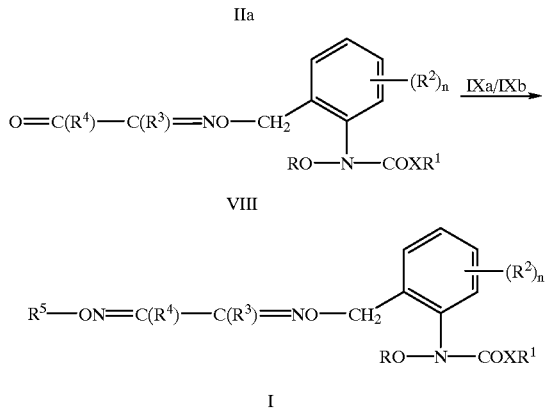

2. Compounds where $R^3$ and/or $R^4$ are a halogen atom are obtained from the corresponding precursors, where the radical concerned is a hydroxyl group, by methods known per se (cf. Houben-Weyl, Vol. E5, p. 631; J. Org. Chem. 36 (1971), 233; J. Org. Chem. 57 (1992), 3245). Preferably, the appropriate reactions to give the halogen derivative are performed in stages I and VIII.

3. Compounds where $R^3$ and/or $R^4$ are an alkoxy or alkylthio group are obtained from the corresponding precursors, where the radical concerned is a halogen atom, by methods known per se (cf. Houben-Weyl, Vol. E5, p. 826ff and 1280ff, J. Org. Chem. 36 (1971), 233, J. Org. Chem. 46 (1981), 3623). Preferably, the appropriate reactions of the halogen derivative are performed in stages I and VIII.

4. Compounds where $R^3$ and/or $R^4$ are an alkoxy group are also obtained from the corresponding precursors where the radical concerned is a hydroxyl group, by methods known per se (cf. Houben-Weyl, Vol. E5, p. 826–829, Aust. J. Chem. 27 (1974), 1341–9). Preferably, the corresponding reactions to give the alkoxy derivatives are performed in stages I and VIII.

Compounds of the formula I where X is $NR^a$ can additionally be obtained by the following processes:

5. For example, compounds of this type are obtained starting from intermediates of the formula X

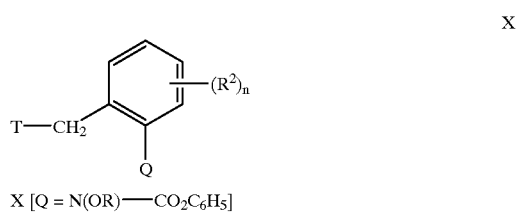

where Q is $N(OR)$—$CO_2C_6H_5$ and T is $O=C(R^4)$—$C(R^3)=NO$—, $HON=C(R^4)$—$C(R^3)=NO$— or $R^5ON=C(R^4)$—$C(R^3)=NO$—, by reaction with an amine of the formula $HNR^aR^1$ (or ammonia in the case where $R^a$ and $R^1$ are hydrogen).

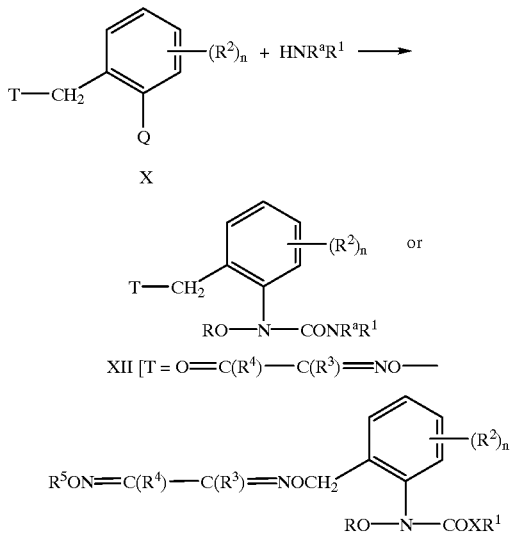

The conversion of the side chain (in the case where T is O=C(R$^4$)—C(R$^3$)=NO— or R$^5$ON=C(R$^4$)—C(R$^3$)=NO—≡ formula XII) is carried out by the methods described above.

6. Alternatively to the preparation method described in item 5, the compounds I where X is NR$^a$ are also obtained according to the following reaction scheme starting from compounds I (or their precursors) where XR$^1$ is a C$_1$-C$_4$-alkoxy group.

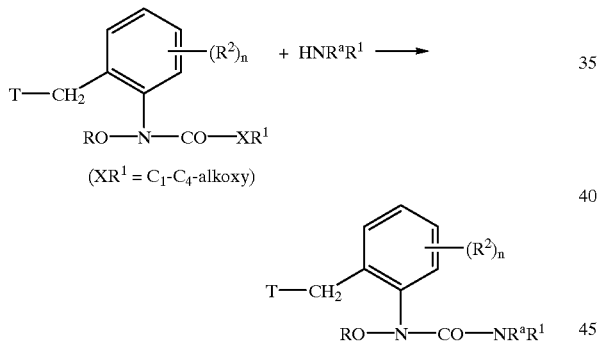

The compounds II are known (WO-A 93/15 046) or can be prepared by the methods described therein.

On account of their C=N double bonds, the compounds I can be obtained during preparation as E/Z isomer mixtures which can be separated into the individual compounds in a customary manner, eg. by crystallization or chromatography.

If isomer mixtures are obtained in the synthesis, in general, however, separation is not absolutely necessary, as the individual isomers can in some cases be converted into one another during preparation for application or during application (eg. under the action of light, acid or base). Corresponding conversions can also be carried out after application, for example in the treated plant or in the harmful fungus or animal pest to be controlled during the treatment of plants.

With reference to the —C(R$^3$)=NOCH$_2$— double bond, with respect to their activity the cis isomers of the compounds I are preferred (configuration based on the radical R$^3$ in relation to the —OCH$_2$— group).

The compounds I can contain acidic or basic centers and accordingly form acid addition products or base addition products or salts.

Acids for acid addition products are, inter alia, inorganic acids (eg. hydrohalic acids such as hydrochloric and hydrobromic acid, phosphoric acid, sulfuric acid, nitric acid), organic acids (eg. formic acid, acetic acid, oxalic acid, malonic acid, lactic acid, malic acid, succinic acid, tartaric acid, citric acid, salicylic acid, p-toluenesulfonic acid, dodecylbenzenesulfonic acid) or other proton-acidic compounds (eg. saccharin).

Bases for base addition products are, inter alia, oxides, hydroxides, carbonates or hydrogencarbonates of alkali metals or alkaline earth metals (eg. potassium or sodium hydroxide or carbonate) or ammonium compounds (eg. ammonium hydroxide).

In the definitions of the compounds I given at the beginning, collective terms were used which are generally representative of the following groups:

Halogen: fluorine, chlorine, bromine and iodine;

Alkyl: straight-chain or branched alkyl groups having 1 to 4, 6 or 10 carbon atoms, eg. C$_1$-C$_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Alkylamino: an amino group which carries a straight-chain or branched alkyl group having 1 to 6 carbon atoms as mentioned above;

Dialkylamino: an amino group which carries two straight-chain or branched alkyl groups which are independent of one another, each having 1 to 6 carbon atoms as mentioned above;

Alkylcarbonyl: straight-chain or branched alkyl groups having 1 to 10 carbon atoms, which are bonded to the structure via a carbonyl group (—CO—);

Alkylsulfonyl: straight-chain or branched alkyl groups having 1 to 6 or 10 carbon atoms, which are bonded to the structure via a sulfonyl group (—SO$_2$—);

Alkylsulfoxyl: straight-chain or branched alkyl groups having 1 to 6 carbon atoms, which are bonded to the structure via a sulfoxyl group (—S(=O)—);

Alkylaminocarbonyl: alkylamino groups having 1 to 6 carbon atoms as mentioned above, which are bonded to the structure via a carbonyl group (—CO—);

Dialkylaminocarbonyl: dialkylamino groups each having 1 to 6 carbon atoms per alkyl radical as mentioned above, which are bonded to the structure via a carbonyl group (—CO—);

Alkylaminothiocarbonyl: alkylamino groups having 1 to 6 carbon atoms as mentioned above, which are bonded to the structure via a thiocarbonyl group (—CS—);

Dialkylaminothiocarbonyl: dialkylamino groups each having 1 to 6 carbon atoms per alkyl radical as mentioned above, which are bonded to the structure via a thiocarbonyl group (—CS—);

Haloalkyl: straight-chain or branched alkyl groups having 1 to 6 carbon atoms, it being possible for the hydrogen atoms in these groups to be partly or completely replaced by halogen atoms as mentioned above, eg. C$_1$-C$_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 4 or 6 carbon atoms as mentioned above, which are bonded to the structure via an oxygen atom (—O—), eg. $C_1$–$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

Alkoxycarbonyl: straight-chain or branched alkyl groups having 1 to 6 carbon atoms, which are bonded to the structure via an oxycarbonyl group (—OC(=O)—);

Haloalkoxy: straight-chain or branched alkyl groups having 1 to 6 carbon atoms, it being possible for the hydrogen atoms in these groups to be partly or completely replaced by halogen atoms as mentioned above, and these groups being bonded to the structure via an oxygen atom;

Alkylthio: straight-chain or branched alkyl groups having 1 to 4 or 6 carbon atoms as mentioned above, which are bonded to the structure via a sulfur atom (—S—), eg. $C_1$–$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

Cycloalkyl: monocyclic alkyl groups having 3 to 6 carbon ring members, eg. cyclopropyl, cyclobutyl, cyclopentyl and cyclohexyl;

Alkenyl: straight-chain or branched alkenyl groups having 2 to 6 or 10 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-di-methyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkenyloxy: straight-chain or branched alkenyl groups having 2 to 6 carbon atoms and a double bond in any desired position, which are bonded to the structure via an oxygen atom (—O—);

Alkenylthio or alkenylamino: straight-chain or branched alkenyl groups having 2 to 6 carbon atoms and a double bond in any desired position, which are bonded to the structure (alkenylthio) via a sulfur atom or (alkenylamino) a nitrogen atom.

Alkenylcarbonyl: straight-chain or branched alkenyl groups having 2 to 10 carbon atoms and a double bond in any desired position, which are bonded to the structure via a carbonyl group (—CO—);

Alkynyl: straight-chain or branched alkynyl groups having 3 to 10 carbon atoms and a triple bond in any desired position, eg. $C_3$–$C_6$-alkynyl such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

Alknyloxy or alkynylthio and alkynylamino: straight-chain or branched alkynyl groups having 2 to 6 carbon atoms and a triple bond in any desired position, which are bonded to the structure (alkynyloxy) via an oxygen atom or (alkynylthio) via a sulfur atom or (alkynylamino) via a nitrogen atom.

Alkynylcarbonyl: straight-chain or branched alkynyl groups having 3 to 10 carbon atoms and a triple bond in any desired position, which are bonded to the structure via a carbonyl group (—CO—);

Cycloalkenyl or cycloalkenyloxy, cycloalkenylthio and cycloalkenylamino: monocyclic alkenyl groups having 3 to 6 carbon ring members, which are bonded to the structure directly or (cycloalkenyloxy) via an oxygen atom or (cycloalkenylthio) a sulfur atom or (cycloalkenylamino) via a nitrogen atom, eg. cyclopropenyl, cyclobutenyl, cyclopentenyl or cyclohexenyl.

Cycloalkoxy or cycloalkylthio and cycloalkylamino: monocyclic alkenyl groups having 3 to 6 carbon ring members, which are bonded to the structure (cycloalkyloxy) via an oxygen atom or (cycloalkylthio) a sulfur atom or (cycloalkylamino) via a nitrogen atom, eg. cyclopropyl, cyclobutyl, cyclopentyl or cyclohexyl;

Heterocyclyl or heterocyclyloxy, heterocyclylthio and heterocyclylamino: three- to six-membered, saturated or partially unsaturated mono- or polycyclic heterocycles which contain one to three hetero atoms selected from a group consisting of oxygen, nitrogen and sulfur, and which are bonded to the structure directly or (heterocyclyloxy) via an oxygen atom or (heterocyclylthio) via a sulfur atom or (heterocyclylamino) via a nitrogen atom, eg. 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroitidazol-5-yl, 4,5-dihydroimidazol-2-yl, 4,5-dihydroitidazol-4-yl, 4,5-dihydroimidazol-5-yl, 2,5-dihydroimidazol-2-yl, 2,5-dihydroitidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl, Aryl or aryloxy, arylthio, arylcarbonyl and arylsulfonyl: aromatic mono- or polycyclic hydrocarbon radicals which are bonded to the structure directly or (aryloxy) via an oxygen atom (—O—) or (arylthio) a sulfur atom (—S—), (arylcarbonyl) via a carbonyl group (—CO—) or (arylsulfonyl) via a sulfonyl group (—SO$_2$—), eg. phenyl, naphthyl and phenanthrenyl or phenyloxy, naphthyloxy and phenanthrenyloxy and the corresponding carbonyl and sulfonyl radicals;

Arylamino: aromatic mono- or polycyclic hydrocarbon radicals which are bonded to the structure via a nitrogen atom.

Hetaryl or hetaryloxy, hetarylthio, hetarylcarbonyl and hetarylsulfonyl: aromatic mono- or polycyclic radicals which beside carbon ring members can additionally contain one to four nitrogen atoms, or one to three nitrogen atoms and an oxygen or a sulfur atom, or an oxygen or a sulfur atom and which are bonded to the structure directly or (hetaryloxy) via an oxygen atom (—O—) or (hetarylthio) a sulfur atom (—S—), (hetarylcarbonyl) via a carbonyl group (—CO—) or (hetarylsulfonyl) via a sulfonyl group (—SO$_2$—), eg.

5-membered heteroaryl, containing one to three nitrogen atoms: 5-membered ring heteroaryl groups which beside carbon atoms can contain one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl, 1,2,3-triazolyl and 1,3,4-triazol-2-yl;

5-membered heteroaryl, containing one to four nitrogen atoms or one to three nitrogen atoms and a sulfur or oxygen atom or an oxygen or a sulfur atom: 5-membered ring heteroaryl groups which beside carbon atoms can contain one to four nitrogen atoms or one to three nitrogen atoms and a sulfur or oxygen atom, or an oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered heteroaryl, containing one to three nitrogen atoms or a nitrogen atom and/or an oxygen or sulfur atom: 5-membered ring heteroaryl groups which in addition to carbon atoms can contain one to four nitrogen atoms, or one to three nitrogen atoms and a sulfur or oxygen atom or an oxygen or a sulfur atom as ring members, and in which two adjacent carbon ring members or a nitrogen and an adjacent carbon ring member can be bridged by a buta-1,3-diene-1,4-diyl group;

5-membered heteroaryl bonded via nitrogen, containing one to four nitrogen atoms, or benzo-fused 5-membered heteroaryl bonded via nitrogen, containing one to three nitrogen atoms: 5-membered ring heteroaryl groups which beside carbon atoms can contain one to four nitrogen atoms or one to three nitrogen atoms as ring members, and in which two adjacent carbon ring members or a nitrogen and an adjacent carbon ring member can be bridged by a buta-1,3-diene-1,4-diyl group, these rings being bonded to the structure via one of the nitrogen ring members;

6-membered heteroaryl, containing one to three or one to four nitrogen atoms: 6-membered ring heteroaryl groups which beside carbon atoms can contain one to three or one to four nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered heteroaryl, containing one to four nitrogen atoms: 6-membered ring heteroaryl groups in which two adjacent carbon ring members can be bridged by a buta-1,3-diene-1,4-diyl group, eg. quinoline, isoquinoline, quinazoline and quinoxaline, or the corresponding oxy, thio, carbonyl or sulfonyl groups.

Hetarylamino: aromatic mono- or polycyclic radicals which, in addition to carbon ring members, can additionally contain one to four nitrogen atoms or one to three nitrogen atoms and an oxygen or a sulfur atom and which are bonded to the structure via a nitrogen atom.

The statement partially or completely halogenated is intended to express that in the groups characterized in this way the hydrogen atoms can be partly or completely replaced by identical or different halogen atoms as mentioned above.

With respect to their biological action, preferred compounds of the formula I are those where n is 0 or 1, in particular 0.

In addition, preferred compounds I are those where R is hydrogen, $C_1$–$C_4$-alkyl or $C_1$–$C_2$-haloalkyl.

Preferred compounds I are additionally those where $R^1X$ is methyl, ethyl, methoxy or methylamino.

Preferred compounds I are equally those where $R^3$ is hydrogen, hydroxyl, cyano, cyclopropyl, chlorine, methyl, ethyl, 1-methylethyl, trifluoromethyl, methoxy, methylthio or phenyl.

Preferred compounds I are additionally those where $R^3$ is methyl.

In addition, preferred compounds I are those where $R^3$ is methoxy.

Preferred compounds I are additionally those where $R^3$ is hydroxyl.

In addition, preferred compounds I are those where $R^3$ is chlorine.

In addition, preferred compounds I are those where $R^4$ is hydrogen, hydroxyl, cyclopropyl, chlorine, methyl, ethyl, isopropyl, n-butyl, isobutyl, tert-butyl, methoxy or methylthio.

Preferred compounds I are additionally those where $R^4$ is methyl.

In addition, preferred compounds I are those where $R^4$ is methoxy.

Preferred compounds I are additionally those where $R^4$ is hydroxyl.

In addition, preferred compounds I are those where $R^4$ is ethyl.

Preferred compounds I are additionally those where $R^4$ is isopropyl.

Preferred compounds I are additionally those where $R^4$ is cyclopropyl.

In addition, preferred compounds I are those where $R^4$ is unsubst. or subst. aryl or hetaryl.

In addition, preferred compounds I are those where $R^4$ is unsubst. or subst. pyridyl, pyrimidyl, pyrazinyl, pyridazinyl or triazinyl.

In addition, preferred compounds I are those where $R^4$ is unsubst. or subst. furyl, thienyl or pyrrolyl.

In addition, preferred compounds I are those where $R^4$ is unsubst. or subst. oxazolyl, thiazolyl, isoxazolyl, isothiazolyl, pyrazolyl or imidazolyl.

In addition, preferred compounds I are those where $R^4$ is unsubst. or subst. oxadiazolyl, thiadiazolyl or triazolyl.

Preferred compounds I are additionally those where $R^4$ is phenyl which is unsubstituted or carries one or two of the following groups: nitro, cyano, hydroxyl, amino, aminocarbonyl, aminothiocarbonyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino, $C_1$–$C_4$-alkylsulfonyl, $C_1$–$C_4$-alkoxycarbonyl, $C_1$–$C_4$-alkylaminocarbonyl or di-$C_1$–$C_4$-alkylaminocarbonyl.

Preferred compounds I are additionally those where $R^5$ is hydrogen, $C_1$–$C_6$-alkyl, arylalkyl, hetarylalkyl, aryloxyalkyl, hetaryloxyalkyl, aryl or hetaryl.

In addition, preferred compounds I are those where $R^5$ is $C_1$–$C_6$-alkyl.

Preferred compounds I are additionally those where $R^5$ is methyl or ethyl.

In addition, preferred compounds I are those where $R^5$ is arylalkyl or hetarylalkyl.

Preferred compounds I are additionally those where $R^5$ is aryloxyalkyl or hetaryloxyalkyl.

Preferred compounds I are additionally those where $R^5$ is aryl or hetaryl.

In particular, with respect to their use preferred compounds I are those compiled in the following Tables. The groups mentioned for a substituent in the Tables are additionally considered per se (independently of the combination in which they are mentioned) to be a particularly preferred embodiment of the substituent concerned.

Table 1

Compounds of the formula I (n=0) where R is hydrogen, $R^1X$ is methyl and the combination of the substituents $R^3$, $R^4$ and $R^5$ for a compound in each case corresponds to one line of Table A Table 2

Compounds of the formula I (n=0) where R is hydrogen, $R^1X$ is ethyl and the combination of the substituents $R^3$, $R^4$ and $R^5$ for a compound in each case corresponds to one line of Table A Table 3

Compounds of the formula I (n=0) where R is hydrogen, $R^1X$ is methoxy and the combination of the substituents $R^3$, $R^4$ and $R^5$ for a compound in each case corresponds to one line of Table A Table 4

Compounds of the formula I (n=0) where R is hydrogen, $R^1X$ is ethoxy and the combination of the substituents $R^3$, $R^4$ and $R^5$ for a compound in each case corresponds to one line of Table A Table 5

Compounds of the formula I (n=0) where R is hydrogen, $R^1X$ is methylamino and the combination of the substituents $R^3$, $R^4$ and $R^5$ for a compound in each case corresponds to one line of Table A Table 6

Compounds of the formula I (n=0) where R is methyl, $R^1X$ is methyl and the combination of the substituents $R^3$, $R^4$ and $R^5$ for a compound in each case corresponds to one line of Table A Table 7
Compounds of the formula I (n=0) where R is methyl, $R^1X$ is ethyl and the combination of the substituents $R^3$, $R^4$ and $R^5$ for a compound in each case corresponds to one line of Table A Table 8
Compounds of the formula I (n=0) where R is methyl, $R^1X$ is methoxy and the combination of the substituents $R^3$, $R^4$ and $R^5$ for a compound in each case corresponds to one line of Table A Table 9
Compounds of the formula I (n=0) where R is methyl, $R^1X$ is ethoxy and the combination of the substituents $R^3$, $R^4$ and $R^5$ for a compound in each case corresponds to one line of Table A Table 10
Compounds of the formula I (n=0) where R is methyl, $R^1X$ is methylamino and the combination of the substituents $R^3$, $R^4$ and $R^5$ for a compound in each case corresponds to one line of Table A Table 11
Compounds of the formula I (n=0) where R is ethyl, $R^1X$ is methyl and the combination of the substituents $R^3$, $R^4$ and $R^5$ for a compound in each case corresponds to one line of Table A Table 12
Compounds of the formula I (n=0) where R is ethyl, $R^1X$ is ethyl and the combination of the substituents $R^3$, $R^4$ and $R^5$ for a compound in each case corresponds to one line of Table A Table 13
Compounds of the formula I (n=0) where R is ethyl, $R^1X$ is methoxy and the combination of the substituents $R^3$, $R^4$ and $R^5$ for a compound in each case corresponds to one line of Table A Table 14
Compounds of the formula I (n=0) where R is ethyl, $R^1X$ is ethoxy and the combination of the substituents $R^3$, $R^4$ and $R^5$ for a compound in each case corresponds to one line of Table A Table 15
Compounds of the formula I (n=0) where R is ethyl, $R^1X$ is methylamino and the combination of the substituents $R^3$, $R^4$ and $R^5$ for a compound in each case corresponds to one line of Table A Table 16
Compounds of the formula I, where $R^2_n$ is 3-chloro, R is hydrogen, $R^1X$ is methyl and the combination of the substituents $R^3$, $R^4$ and $R^5$ for a compound in each case corresponds to one line of Table A Table 17
Compounds of the formula I, where $R^2n$ is 3-chloro, R is hydrogen, $R^1X$ is ethyl and the combination of the substituents $R^3$, $R^4$ and $R^5$ for a compound in each case corresponds to one line of Table A Table 18
Compounds of the formula I, where $R^2_n$ is 3-chloro, R is hydrogen, $R^1X$ is methoxy and the combination of the substituents $R^3$, $R^4$ and $R^5$ for a compound in each case corresponds to one line of Table A Table 19
Compounds of the formula I, where $R^2_n$ is 3-chloro, R is hydrogen, $R^1X$ is ethoxy and the combination of the substituents $R^3$, $R^4$ and $R^5$ for a compound in each case corresponds to one line of Table A Table 20
Compounds of the formula I, where $R^2_n$ is 3-chloro, R is hydrogen, $R^1X$ is methylamino and the combination of the substituents $R^3$, $R^4$ and $R^5$ for a compound in each case corresponds to one line of Table A Table 21
Compounds of the formula I, where $R^2_n$ is 3-chloro, R is methyl, $R^1X$ is methyl and the combination of the substituents $R^3$, $R^4$ and $R^5$ for a compound in each case corresponds to one line of Table A Table 22
Compounds of the formula I, where $R^2_n$ is 3-chloro, R is methyl, $R^1X$ is ethyl and the combination of the substituents $R^3$, $R^4$ and $R^5$ for a compound in each case corresponds to one line of Table A Table 23
Compounds of the formula I, where $R^2_n$ is 3-chloro, R is methyl, $R^1X$ is methoxy and the combination of the substituents $R^3$, $R^4$ and $R^5$ for a compound in each case corresponds to one line of Table A Table 24
Compounds of the formula I, where $R^2_n$ is 3-chloro, R is methyl, $R^1X$ is ethoxy and the combination of the substituents $R^3$, $R^4$ and. $R^5$ for a compound in each case corresponds to one line of Table A Table 25
Compounds of the formula I, where $R^2_n$ is 3-chloro, R is methyl, $R^1X$ is methylamino and the combination of the substituents $R^3$, $R^4$ and $R^5$ for a compound in each case corresponds to one line of Table A Table 26
Compounds of the formula I, where $R^2_n$ is 3-chloro, R is ethyl, $R^1X$ is methyl and the combination of the substituents $R^3$, $R^4$ and $R^5$ for a compound in each case corresponds to one line of Table A Table 27
Compounds of the formula I, where $R^2_n$ is 3-chloro, R is ethyl, $R^1X$ is ethyl and the combination of the substituents $R^3$, $R^4$ and $R^5$ for a compound in each case corresponds to one line of Table A Table 28
Compounds of the formula I, where $R^2_n$ is 3-chloro, R is ethyl, $R^1X$ is methoxy and the combination of the substituents $R^3$, $R^4$ and $R^5$ for a compound in each case corresponds to one line of Table A Table 29
Compounds of the formula I, where $R^2_n$ is 3-chloro, R is ethyl, $R^1X$ is ethoxy and the combination of the substituents $R^3$, $R^4$ and $R^5$ for a compound in each case corresponds to one line of Table A Table 30
Compounds of the formula I, where $R^2_n$ is 3-chloro, R is ethyl, $R^1X$ is methylamino and the combination of the substituents $R^3$, $R^4$ and $R^5$ for a compound in each case corresponds to one line of Table A Table 31
Compounds of the formula I, where $R^2_n$ is 6-methyl, R is hydrogen, $R^1X$ is methyl and the combination of the substituents $R^3$, $R^4$ and $R^5$ for a compound in each case corresponds to one line of Table A Table 32
Compounds of the formula I, where $R^2_n$ is 6-methyl, R is hydrogen, $R^1X$ is ethyl and the combination of the substituents $R^3$, $R^4$ and $R^5$ for a compound in each case corresponds to one line of Table A Table 33
Compounds of the formula I, where $R^2_n$ is 6-methyl, R is hydrogen, $R^1X$ is methoxy and the combination of the substituents $R^3$, $R^4$ and $R^5$ for a compound in each case corresponds to one line of Table A Table 34

Compounds of the formula I, where $R^2{}_n$ is 6-methyl, R is hydrogen, $R^1X$ is ethoxy and the combination of the substituents $R^3$, $R^4$ and $R^5$ for a compound in each case corresponds to one line of Table A Table 35

Compounds of the formula I, where $R^2{}_n$ is 6-methyl, R is hydrogen, $R^1X$ is methylamino and the combination of the substituents $R^3$, $R^4$ and $R^5$ for a compound in each case corresponds to one line of Table A Table 36

Compounds of the formula I, where $R^2{}_n$ is 6-methyl, R is methyl, $R^1X$ is methyl and the combination of the substituents $R^3$, $R^4$ and $R^5$ for a compound in each case corresponds to one line of Table A Table 37

Compounds of the formula I, where $R^2{}_n$ is 6-methyl, R is methyl, $R^1X$ is ethyl and the combination of the substituents $R^3$, $R^4$ and $R^5$ for a compound in each case corresponds to one line of Table A Table 38

Compounds of the formula I, where $R^2{}_n$ is 6-methyl, R is methyl, $R^1X$ is methoxy and the combination of the substituents $R^3$, $R^4$ and $R^5$ for a compound in each case corresponds to one line of Table A Table 39

Compounds of the formula I, where $R^2{}_n$ is 6-methyl, R is methyl, $R^1X$ is ethoxy and the combination of the substituents $R^3$, $R^4$ and $R^5$ for a compound in each case corresponds to one line of Table A Table 40

Compounds of the formula I, where $R^2{}_n$ is 6-methyl, R is methyl, $R^1X$ is methylamino and the combination of the substituents $R^3$, $R^4$ and $R^5$ for a compound in each case corresponds to one line of Table A Table 41

Compounds of the formula I, where $R^2{}_n$ is 6-methyl, R is ethyl, $R^1X$ is methyl and the combination of the substituents $R^3$, $R^4$ and $R^5$ for a compound in each case corresponds to one line of Table A Table 42

Compounds of the formula I, where $R^2{}_n$ is 6-methyl, R is ethyl, $R^1X$ is ethyl and the combination of the substituents $R^3$, $R^4$ and $R^5$ for a compound in each case corresponds to one line of Table A Compounds of the formula I, where $R^2{}_n$ is 6-methyl, R is ethyl, $R^1X$ is methoxy and the combination of the substituents $R^3$, $R^4$ and $R^5$ for a compound in each case corresponds to one line of Table A Table 44

Compounds of the formula I, where $R^2{}_n$ is 6-methyl, R is ethyl, $R^1X$ is ethoxy and the combination of the substituents $R^3$, $R^4$ and $R^5$ for a compound in each case corresponds to one line of Table A Table 45

Compounds of the formula I, where $R^2{}_n$ is 6-methyl, R is ethyl, $R^1X$ is methylamino and the combination of the substituents $R^3$, $R^4$ and $R^5$ for a compound in each case corresponds to one line of Table A

TABLE A

| No. | $R^3$ | $R^4$ | $R^5$ |
|---|---|---|---|
| 1 | $CH_3$ | $CH_3$ | H |
| 2 | $CH_3$ | $CH_3$ | $CH_3$ |
| 3 | $CH_3$ | $CH_3$ | $C_2H_5$ |
| 4 | $CH_3$ | $CH_3$ | n-$C_3H_7$ |
| 5 | $CH_3$ | $CH_3$ | i-$C_3H_7$ |
| 6 | $CH_3$ | $CH_3$ | Cyclopropyl |
| 7 | $CH_3$ | $CH_3$ | n-$C_4H_9$ |
| 8 | $CH_3$ | $CH_3$ | s-$C_4H_9$ |
| 9 | $CH_3$ | $CH_3$ | i-$C_4H_9$ |
| 10 | $CH_3$ | $CH_3$ | t-$C_4H_9$ |
| 11 | $CH_3$ | $CH_3$ | n-$C_5H_{11}$ |
| 12 | $CH_3$ | $CH_3$ | i-$C_5H_{11}$ |
| 13 | $CH_3$ | $CH_3$ | neo-$C_5H_{11}$ |
| 14 | $CH_3$ | $CH_3$ | Cyclopentyl |
| 15 | $CH_3$ | $CH_3$ | n-$C_6H_{13}$ |
| 16 | $CH_3$ | $CH_3$ | Cyclohexyl |
| 17 | $CH_3$ | $CH_3$ | n-$C_8H_{17}$ |
| 18 | $CH_3$ | $CH_3$ | $CH_2CH_2Cl$ |
| 19 | $CH_3$ | $CH_3$ | $(CH_2)_4Cl$ |
| 20 | $CH_3$ | $CH_3$ | $CH_2CN$ |
| 21 | $CH_3$ | $CH_3$ | $CH_2CH_2CN$ |
| 22 | $CH_3$ | $CH_3$ | $(CH_2)_3CN$ |
| 23 | $CH_3$ | $CH_3$ | $(CH_2)_4CN$ |
| 24 | $CH_3$ | $CH_3$ | $(CH_2)_6CN$ |
| 25 | $CH_3$ | $CH_3$ | Cyclohexylmethyl |
| 26 | $CH_3$ | $CH_3$ | 2-Cyclohexyleth-1-yl |
| 27 | $CH_3$ | $CH_3$ | Cyclopropylmethyl |
| 28 | $CH_3$ | $CH_3$ | 2-Cyclopropyleth-1-yl |
| 29 | $CH_3$ | $CH_3$ | 2-Methoxyeth-1-yl |
| 30 | $CH_3$ | $CH_3$ | 2-Ethoxyeth-1-yl |
| 31 | $CH_3$ | $CH_3$ | 2-Isopropoxyeth-1-yl |
| 32 | $CH_3$ | $CH_3$ | 3-Methoxyprop-1-yl |
| 33 | $CH_3$ | $CH_3$ | 3-Ethoxyprop-1-yl |
| 34 | $CH_3$ | $CH_3$ | 3-Isopropoxyprop-1-yl |
| 35 | $CH_3$ | $CH_3$ | 4-Methoxybut-1-yl |
| 36 | $CH_3$ | $CH_3$ | 4-Isopropoxybut-1-yl |
| 37 | $CH_3$ | $CH_3$ | Propen-3-yl |
| 38 | $CH_3$ | $CH_3$ | But-2-en-1-yl |

TABLE A-continued

| No. | R³ | R⁴ | R⁵ |
|---|---|---|---|
| 39 | CH₃ | CH₃ | 3-Methylbut-2-en-1-yl |
| 40 | CH₃ | CH₃ | 2-Vinyloxyeth-1-yl |
| 41 | CH₃ | CH₃ | Allyloxyeth-1-yl |
| 42 | CH₃ | CH₃ | 2-Trifluoromethoxyeth-1-yl |
| 43 | CH₃ | CH₃ | 3-Trifluoromethoxyprpp-1-yl |
| 44 | CH₃ | CH₃ | 4-Difluoromethoxybut-1-yl |
| 45 | CH₃ | CH₃ | Hydroxycarbonylmethyl |
| 46 | CH₃ | CH₃ | Methoxycarbonylmethyl |
| 47 | CH₃ | CH₃ | Aminocarbonylmethyl |
| 48 | CH₃ | CH₃ | N-Methylaminocarbonylmethyl |
| 49 | CH₃ | CH₃ | N,N-Dimethylaminocarbonyl-methyl |
| 50 | CH₃ | CH₃ | 2-Hydroxycarbonyleth-1-yl |
| 51 | CH₃ | CH₃ | 2-Methoxycarbonyleth-1-yl |
| 52 | CH₃ | CH₃ | 2-Aminocarbonyleth-1-yl |
| 53 | CH₃ | CH₃ | 2-N-Methylaminocarbonyleth-1-yl |
| 54 | CH₃ | CH₃ | 2-Dimethylaminocarbonyleth-1-yl |
| 55 | CH₃ | CH₃ | 2-Aminoeth-1-yl |
| 56 | CH₃ | CH₃ | 2-Aminoprop-1-yl |
| 57 | CH₃ | CH₃ | 4-Aminobut-1-yl |
| 58 | CH₃ | CH₃ | 3-Dimethylaminoprop-1-yl |
| 59 | CH₃ | CH₃ | 4-Aminothiocarbonylbut-1-yl |
| 60 | CH₃ | CH₃ | 2-Oxopropyl |
| 61 | CH₃ | CH₃ | Cyclohexyl |
| 62 | CH₃ | CH₃ | Cyclopropyl |
| 63 | CH₃ | CH₃ | Cyclopentyl |
| 64 | CH₃ | CH₃ | 2-Methoxylminoprop-1-yl |
| 65 | CH₃ | CH₃ | 2-Methoxylminoeth-1-yl |
| 66 | CH₃ | CH₃ | 6-Aminocarbonylhex-1-yl |
| 67 | CH₃ | CH₃ | 3-Aminothiocarbonylprop-1-yl |
| 68 | CH₃ | CH₃ | 2-Aminothiocarbonyleth-1-yl |
| 69 | CH₃ | CH₃ | Aminothiocarbonylmethyl |
| 70 | CH₃ | CH₃ | 4-(N,N-Dimethylamino)but-1-yl |
| 71 | CH₃ | CH₃ | 2-(Methylthio)eth-1-yl |
| 72 | CH₃ | CH₃ | 2-(Methylsulfonyl)eth-1-yl |
| 73 | CH₃ | CH₃ | 4-(Methylthio)prop-1-yl |
| 74 | CH₃ | CH₃ | 4-(Methylsulfonyl)prop-1-yl |
| 75 | CH₃ | CH₃ | Benyzl |
| 76 | CH₃ | CH₃ | 2-F—C₆H₄—CH₂ |
| 77 | CH₃ | CH₃ | 3-F—C₆H₄—CH₂ |
| 78 | CH₃ | CH₃ | 4-F—C₆H₄—CH₂ |
| 79 | CH₃ | CH₃ | 2,3-F₂—C₆H₃—CH₂ |
| 80 | CH₃ | CH₃ | 2,4-F₂—C₆H₃—CH₂ |
| 81 | CH₃ | CH₃ | 2,5-F₂—C₆H₃—CH₂ |
| 82 | CH₃ | CH₃ | 2,6-F₂—C₆H₃—CH₂ |
| 83 | CH₃ | CH₃ | 3,4-F₂—C₆H₃—CH₂ |
| 84 | CH₃ | CH₃ | 3,5-F₂—C₆H₃—CH₂ |
| 85 | CH₃ | CH₃ | 2-Cl—C₆H₄—CH₂ |
| 86 | CH₃ | CH₃ | 3-Cl—C₆H₄—CH₂ |
| 87 | CH₃ | CH₃ | 4-Cl—C₆H₄—CH₂ |
| 88 | CH₃ | CH₃ | 2,3-Cl₂—C₆H₃—CH₂ |
| 89 | CH₃ | CH₃ | 2,4-Cl₂—C₆H₃—CH₂ |
| 90 | CH₃ | CH₃ | 2,5-Cl₂—C₆H₃—CH₂ |
| 91 | CH₃ | CH₃ | 2,6-Cl₂—C₆H₃—CH₂ |
| 92 | CH₃ | CH₃ | 3,4-Cl₂—C₆H₃—CH₂ |
| 93 | CH₃ | CH₃ | 3,5-Cl₂—C₆H₃—CH₂ |
| 94 | CH₃ | CH₃ | 2,3,4-Cl₃—C₆H₂—CH₂ |
| 95 | CH₃ | CH₃ | 2,3,5-Cl₃—C₆H₂—CH₂ |
| 96 | CH₃ | CH₃ | 2,3,6-Cl₃—C₆H₂—CH₂ |
| 97 | CH₃ | CH₃ | 2,4,5-Cl₃—C₆H₂—CH₂ |
| 98 | CH₃ | CH₃ | 2,4,6-Cl₃—C₆H₂—CH₂ |
| 99 | CH₃ | CH₃ | 3,4,5-Cl₃—C₆H₂—CH₂ |
| 100 | CH₃ | CH₃ | 2-Br—C₆H₄—CH₂ |
| 101 | CH₃ | CH₃ | 3-Br—C₆H₄—CH₂ |
| 102 | CH₃ | CH₃ | 4-Br—C₆H₄—CH₂ |
| 103 | CH₃ | CH₃ | 2,3-Br₂—C₆H₃—CH₂ |
| 104 | CH₃ | CH₃ | 2,4-Br₂—C₆H₃—CH₂ |
| 105 | CH₃ | CH₃ | 2,5-Br₂—C₆H₃—CH₂ |
| 106 | CH₃ | CH₃ | 2,6-Br₂—C₆H₃—CH₂ |
| 107 | CH₃ | CH₃ | 3,4-Br₂—C₆H₃—CH₂ |
| 108 | CH₃ | CH₃ | 3,5-Br₂—C₆H₃—CH₂ |
| 109 | CH₃ | CH₃ | 2-F, 3-Cl—C₆H₃—CH₂ |
| 110 | CH₃ | CH₃ | 2-F, 4-Cl—C₆H₃—CH₂ |
| 111 | CH₃ | CH₃ | 2-F, 5-Cl—C₆H₃—CH₂ |
| 112 | CH₃ | CH₃ | 2-F, 3-Br—C₆H₃—CH₂ |
| 113 | CH₃ | CH₃ | 2-F, 4-Br—C₆H₃—CH₂ |
| 114 | CH₃ | CH₃ | 2-F, 5-Br—C₆H₃—CH₂ |
| 115 | CH₃ | CH₃ | 2-Cl, 3-Br—C₆H₃—CH₂ |

TABLE A-continued

| No. | R³ | R⁴ | R⁵ |
|---|---|---|---|
| 116 | CH₃ | CH₃ | 2-Cl, 4-Br—C₆H₃—CH₂ |
| 117 | CH₃ | CH₃ | 2-Cl, 5-Br—C₆H₃—CH₂ |
| 118 | CH₃ | CH₃ | 3-F, 4-Cl—C₆H₃—CH₂ |
| 119 | CH₃ | CH₃ | 3-F, 5-Cl—C₆H₃—CH₂ |
| 120 | CH₃ | CH₃ | 3-F, 6-Cl—C₆H₃—CH₂ |
| 121 | CH₃ | CH₃ | 3-F, 4-Br—C₆H₃—CH₂ |
| 122 | CH₃ | CH₃ | 3-F, 5-Br—C₆H₃—CH₂ |
| 123 | CH₃ | CH₃ | 3-F, 6-Br—C₆H₃—CH₂ |
| 124 | CH₃ | CH₃ | 3-Cl, 4-Br—C₆H₃—CH₂ |
| 125 | CH₃ | CH₃ | 3-Cl, 5-Br—C₆H₃—CH₂ |
| 126 | CH₃ | CH₃ | 3-Cl, 6-Br—C₆H₃—CH₂ |
| 127 | CH₃ | CH₃ | 4-F, 5-Cl—C₆H₃—CH₂ |
| 128 | CH₃ | CH₃ | 4-F, 6-Cl—C₆H₃—CH₂ |
| 129 | CH₃ | CH₃ | 4-F, 5-Br—C₆H₃—CH₂ |
| 130 | CH₃ | CH₃ | 4-F, 6-Br—C₆H₃—CH₂ |
| 131 | CH₃ | CH₃ | 4-Cl, 5-Br—C₆H₃—CH₂ |
| 132 | CH₃ | CH₃ | 5-F, 6-Cl—C₆H₃—CH₂ |
| 133 | CH₃ | CH₃ | 5-F, 6-Br—C₆H₃—CH₂ |
| 134 | CH₃ | CH₃ | 5-Cl, 6-Br—C₆H₃—CH₂ |
| 135 | CH₃ | CH₃ | 3-Br, 4-Cl, 5-Br—C₆H₂—CH₂ |
| 136 | CH₃ | CH₃ | 2-CN—C₆H₄—CH₂ |
| 137 | CH₃ | CH₃ | 3-CN—C₆H₄—CH₂ |
| 138 | CH₃ | CH₃ | 4-CN—C₆H₄—CH₂ |
| 139 | CH₃ | CH₃ | 2-NO₂—C₆H₄—CH₂ |
| 140 | CH₃ | CH₃ | 3-NO₂—C₆H₄—CH₂ |
| 141 | CH₃ | CH₃ | 4-NO₂—C₆H₄—CH₂ |
| 142 | CH₃ | CH₃ | 2-CH₃—C₆H₄—CH₂ |
| 143 | CH₃ | CH₃ | 3-CH₃—C₆H₄—CH₂ |
| 144 | CH₃ | CH₃ | 4-CH₃—C₆H₄—CH₂ |
| 145 | CH₃ | CH₃ | 2,3-(CH₃)₂—C₆H₃—CH₂ |
| 146 | CH₃ | CH₃ | 2,4-(CH₃)₂—C₆H₃—CH₂ |
| 147 | CH₃ | CH₃ | 2,5-(CH₃)₂—C₆H₃—CH₂ |
| 148 | CH₃ | CH₃ | 2,6-(CH₃)₂—C₆H₃—CH₂ |
| 149 | CH₃ | CH₃ | 3,4-(CH₃)₂—C₆H₃—CH₂ |
| 150 | CH₃ | CH₃ | 3,5-(CH₃)₂—C₆H₃—CH₂ |
| 151 | CH₃ | CH₃ | 2-C₂H₅—C₆H₄—CH₂ |
| 152 | CH₃ | CH₃ | 3-C₂H₅—C₆H₄—CH₂ |
| 153 | CH₃ | CH₃ | 4-C₂H₅—C₆H₄—CH₂ |
| 154 | CH₃ | CH₃ | 2-i-C₃H₇—C₆H₄—CH₂ |
| 155 | CH₃ | CH₃ | 3-i-C₃H₇—C₆H₄—CH₂ |
| 156 | CH₃ | CH₃ | 4-i-C₃H₇—C₆H₄—CH₂ |
| 157 | CH₃ | CH₃ | 2-Cyclohexyl-C₆H₄—CH₂ |
| 158 | CH₃ | CH₃ | 3-Cyclohexyl-C₆H₄—CH₂ |
| 159 | CH₃ | CH₃ | 4-Cyclohexyl-C₆H₄—CH₂ |
| 160 | CH₃ | CH₃ | 2-Vinyl-C₆H₄—CH₂ |
| 161 | CH₃ | CH₃ | 3-Vinyl-C₆H₄—CH₂ |
| 162 | CH₃ | CH₃ | 4-Vinyl-C₆H₄—CH₂ |
| 163 | CH₃ | CH₃ | 2-Allyl-C₆H₄—CH₂ |
| 164 | CH₃ | CH₃ | 3-Allyl-C₆H₄—CH₂ |
| 165 | CH₃ | CH₃ | 4-Allyl-C₆H₄—CH₂ |
| 166 | CH₃ | CH₃ | 2-C₆H₅—C₆H₄—CH₂ |
| 167 | CH₃ | CH₃ | 3-C₆H₅—C₆H₄—CH₂ |
| 168 | CH₃ | CH₃ | 4-C₆H₅—C₆H₄—CH₂ |
| 169 | CH₃ | CH₃ | 3-CH₃, 5-t-C₄H₉—C₆H₃—CH₂ |
| 170 | CH₃ | CH₃ | 2-OH—C₆H₄—CH₂ |
| 171 | CH₃ | CH₃ | 3-OH—C₆H₄—CH₂ |
| 172 | CH₃ | CH₃ | 4-OH—C₆H₄—CH₂ |
| 173 | CH₃ | CH₃ | 2-OCH₃—C₆H₄—CH₂ |
| 174 | CH₃ | CH₃ | 3-OCH₃—C₆H₄—CH₂ |
| 175 | CH₃ | CH₃ | 4-OCH₃—C₆H₄—CH₂ |
| 176 | CH₃ | CH₃ | 2,3-(OCH₃)₂—C₆H₃—CH₂ |
| 177 | CH₃ | CH₃ | 2,4-(OCH₃)₂—C₆H₃—CH₂ |
| 178 | CH₃ | CH₃ | 2,5-(OCH₃)₂—C₆H₃—CH₂ |
| 179 | CH₃ | CH₃ | 3,4-(OCH₃)₂—C₆H₃—CH₂ |
| 180 | CH₃ | CH₃ | 3,5-(OCH₃)₂—C₆H₃—CH₂ |
| 181 | CH₃ | CH₃ | 3,4,5-(OCH₃)₃—C₆H₂—CH₂ |
| 182 | CH₃ | CH₃ | 2-OC₂H₅—C₆H₄—CH₂ |
| 183 | CH₃ | CH₃ | 3-OC₂H₅—C₆H₄—CH₂ |
| 184 | CH₃ | CH₃ | 4-OC₂H₅—C₆H₄—CH₂ |
| 185 | CH₃ | CH₃ | 2-O-(n-C₃H₇)—C₆H₄—CH₂ |
| 186 | CH₃ | CH₃ | 3-O-(n-C₃H₇)—C₆H₄—CH₂ |
| 187 | CH₃ | CH₃ | 4-O-(n-C₃H₇)—C₆H₄—CH₂ |
| 188 | CH₃ | CH₃ | 2-O-(i-C₃H₇)—C₆H₄—CH₂ |
| 189 | CH₃ | CH₃ | 3-O-(i-C₃H₇)—C₆H₄—CH₂ |
| 190 | CH₃ | CH₃ | 4-O-(i-C₃H₇)—C₆H₄—CH₂ |
| 191 | CH₃ | CH₃ | 4-O-(n-C₄H₉)—C₆H₄—CH₂ |
| 192 | CH₃ | CH₃ | 3-O-(t-C₄H₉)—C₆H₄—CH₂ |

TABLE A-continued

| No. | R³ | R⁴ | R⁵ |
|---|---|---|---|
| 193 | CH₃ | CH₃ | 4-O-(n-C₆H₁₃)—C₆H₄—CH₂ |
| 194 | CH₃ | CH₃ | 2-O-Allyl-C₆H₄—CH₂ |
| 195 | CH₃ | CH₃ | 3-O-Allyl-C₆H₄—CH₂ |
| 196 | CH₃ | CH₃ | 4-O-Allyl-C₆H₄—CH₂ |
| 197 | CH₃ | CH₃ | 2-CF₃—C₆H₄—CH₂ |
| 198 | CH₃ | CH₃ | 3-CF₃—C₆H₄—CH₂ |
| 199 | CH₃ | CH₃ | 4-CF₃—C₆H₄—CH₂ |
| 200 | CH₃ | CH₃ | 2-Acetyl-C₆H₄—CH₂ |
| 201 | CH₃ | CH₃ | 3-Acetyl-C₆H₄—CH₂ |
| 202 | CH₃ | CH₃ | 4-Acetyl-C₆H₄—CH₂ |
| 203 | CH₃ | CH₃ | 2-Methoxycarbonyl-C₆H₄—CH₂ |
| 204 | CH₃ | CH₃ | 3-Methoxycarbonyl-C₆H₄—CH₂ |
| 205 | CH₃ | CH₃ | 4-Methoxycarbonyl-C₆H₄—CH₂ |
| 206 | CH₃ | CH₃ | 2-Aminocarbonyl-C₆H₄—CH₂ |
| 207 | CH₃ | CH₃ | 3-Aminocarbonyl-C₆H₄—CH₂ |
| 208 | CH₃ | CH₃ | 4-Aminocarbonyl-C₆H₄—CH₂ |
| 209 | CH₃ | CH₃ | 2-Dimethylaminbcarbonyl-C₆H₄—CH₂ |
| 210 | CH₃ | CH₃ | 3-Dimethy-aminocarbonyl-C₆H₄—CH₂ |
| 211 | CH₃ | CH₃ | 4-Dimethylaminocarbonyl-C₆H₄—CH₂ |
| 212 | CH₃ | CH₃ | 2-(N-Methylaminocarbonyl)-C₆H₄—CH₂ |
| 213 | CH₃ | CH₃ | 3-(N-Methylaminocarbonyl)-C₆H₄—CH₂ |
| 214 | CH₃ | CH₃ | 4-(N-Methylaminocarbonyl)-C₆H₄—CH₂ |
| 215 | CH₃ | CH₃ | 2-H₂N—C₆H₄—CH₂ |
| 216 | CH₃ | CH₃ | 3-H₂N—C₆H₄—CH₂ |
| 217 | CH₃ | CH₃ | 4-H₂N—C₆H₄—CH₂ |
| 218 | CH₃ | CH₃ | 2-Aminothiocarbonyl-C₆H₄—CH₂ |
| 219 | CH₃ | CH₃ | 3-Aminothiocarbonyl-C₆H₄—CH₂ |
| 220 | CH₃ | CH₃ | 4-Aminothiocarbonyl-C₆H₄—CH₂ |
| 221 | CH₃ | CH₃ | 2-Methoxyiminomethyl-C₆H₄—CH₂ |
| 222 | CH₃ | CH₃ | 3-Methoxyiminomethyl-C₆H₄—CH₂ |
| 223 | CH₃ | CH₃ | 4-Methoxyiminomethyl-C₆H₄—CH₂ |
| 224 | CH₃ | CH₃ | 2-Formyl-C₆H₄—CH₂ |
| 225 | CH₃ | CH₃ | 3-Formyl-C₆H₄—CH₂ |
| 226 | CH₃ | CH₃ | 4-Formyl-C₆H₄—CH₂ |
| 227 | CH₃ | CH₃ | 2-(1'-Methoxyiminoeth-1'-yl)-C₆H₄—CH₂ |
| 228 | CH₃ | CH₃ | 3-(1'-Methoxyiminoeth-1'-yl)-C₆H₄—CH₂ |
| 229 | CH₃ | CH₃ | 4-(1'-Methoxyiminoeth-1'-yl)-C₆H₄—CH₂ |
| 230 | CH₃ | CH₃ | 2-SCH₃—C₆H₄—CH₂ |
| 231 | CH₃ | CH₃ | 3-SCH₃—C₆H₄—CH₂ |
| 232 | CH₃ | CH₃ | 4-SCH₃—C₆H₄—CH₂ |
| 233 | CH₃ | CH₃ | 2-SO₂CH₃—C₆H₄—CH₂ |
| 234 | CH₃ | CH₃ | 3-SO₂CH₃—C₆H₄—CH₂ |
| 235 | CH₃ | CH₃ | 4-SO₂CH₃—C₆H₄—CH₂ |
| 236 | CH₃ | CH₃ | 2-OCF₃—C₆H₄—CH₂ |
| 237 | CH₃ | CH₃ | 3-OCF₃—C₆H₄—CH₂ |
| 238 | CH₃ | CH₃ | 4-OCF₃—C₆H₄—CH₂ |
| 239 | CH₃ | CH₃ | 2-OCHF₂—C₆H₄—CH₂ |
| 240 | CH₃ | CH₃ | 3-OCHF₂—C₆H₄—CH₂ |
| 241 | CH₃ | CH₃ | 4-OCHF₂—C₆H₄—CH₂ |
| 242 | CH₃ | CH₃ | 3-CF₃, 4-OCF₃—C₆H₃—CH₂ |
| 243 | CH₃ | CH₃ | 1-Naphthyl-CH₂ |
| 244 | CH₃ | CH₃ | 2-Naphthyl-CH₂ |
| 245 | CH₃ | CH₃ | 2-Phenoxyeth-1-yl |
| 246 | CH₃ | CH₃ | 2-(2'-Chlorophenoxy)eth-1-yl |
| 247 | CH₃ | CH₃ | 2-(3'-Chlorophenoxy)eth-1-yl |
| 248 | CH₃ | CH₃ | 2-(4'-Chlorophenoxy)eth-1-yl |
| 249 | CH₃ | CH₃ | 2-(3',5'-Dichlorophenoxy)eth-1-yl |
| 250 | CH₃ | CH₃ | 2-(2'-Cyanophenoxy)eth-1-yl |
| 251 | CH₃ | CH₃ | 2-(3'-Cyanophenoxy)eth-1-yl |
| 252 | CH₃ | CH₃ | 2-(4'-Cyanophenoxy)eth-1-yl |
| 253 | CH₃ | CH₃ | 2-(2'-Methylphenoxy)eth-1-yl |
| 254 | CH₃ | CH₃ | 2-(3'-Methylphenoxy)eth-1-yl |
| 255 | CH₃ | CH₃ | 2-(4'-Methylphenoxy)eth-1-yl |
| 256 | CH₃ | CH₃ | 2-(3'-t-Butylphenoxy)eth-1-yl |
| 257 | CH₃ | CH₃ | 2-(4'-t-Butylphenoxy)eth-1-yl |
| 258 | CH₃ | CH₃ | 2-(2'-Nitrophenoxy)eth-1-yl |
| 259 | CH₃ | CH₃ | 2-(3'-Nitrophenoxy)eth-1-yl |
| 260 | CH₃ | CH₃ | 2-(4'-Nitrophenoxy)eth-1-yl |
| 261 | CH₃ | CH₃ | 2-(2'-Methoxyphenoxy)eth-1-yl |
| 262 | CH₃ | CH₃ | 2-(3'-Methoxyphenoxy)eth-1-yl |
| 263 | CH₃ | CH₃ | 2-(4'-Methoxyphenoxy)eth-1-yl |
| 264 | CH₃ | CH₃ | 2-(2'-Trifluoromethylphenoxy)eth-1-yl |
| 265 | CH₃ | CH₃ | 2-(3'-Trifluoromethylphenoxy)eth-1-yl |
| 266 | CH₃ | CH₃ | 2-(4'-Trifluoromethylphenoxy)eth-1-yl |
| 267 | CH₃ | CH₃ | 2-(2'-Acetylphenoxy)eth-1-yl |
| 268 | CH₃ | CH₃ | 2-(3'-Acetylphenoxy)eth-1-yl |
| 269 | CH₃ | CH₃ | 2-(4'-Acetylphenoxy)eth-1-yl |

TABLE A-continued

| No. | R³ | R⁴ | R⁵ |
|---|---|---|---|
| 270 | CH₃ | CH₃ | 2-(2'-Methoxycarbbnyl)eth-1-yl |
| 271 | CH₃ | CH₃ | 2-(3'-Methoxycarbonyl)eth-1-yl |
| 272 | CH₃ | CH₃ | 2-(4'-Methoxycarbonyl)eth-1-yl |
| 273 | CH₃ | CH₃ | 2-(2'-Dimethylaminocarbonyl)eth-1-yl |
| 274 | CH₃ | CH₃ | 2-(3'-Dimethylaminocarbonyl)eth-1-yl |
| 275 | CH₃ | CH₃ | 2-(4'-Dimethylaminocarbonyl)eth-1-yl |
| 276 | CH₃ | CH₃ | 2-(2'-Aminothiocarbonyl)eth-1-yl |
| 277 | CH₃ | CH₃ | 2-(3'-Aminothiocarbonyl)eth-1-yl |
| 278 | CH₃ | CH₃ | 2-(4'-Aminothiocarbonyl)eth-1-yl |
| 279 | CH₃ | CH₃ | 2-(2'-Methylsulfonyl)eth-1-yl |
| 280 | CH₃ | CH₃ | 2-(3'-Methylsu1fonyl)eth-1-yl |
| 281 | CH₃ | CH₃ | 2-(4'-Methylsulfonyl)eth-1-yl |
| 282 | CH₃ | CH₃ | 3-Phenoxyprop-1-yl |
| 283 | CH₃ | CH₃ | 3-(2'-Chlorophenoxy)prop-1-yl |
| 284 | CH₃ | CH₃ | 3-(3'-Chlorophenoxy)prop-1-yl |
| 285 | CH₃ | CH₃ | 3-(4'-Chlorophenoxy)prop-1-yl |
| 286 | CH₃ | CH₃ | 3-(3',5',Dichlorophenoxy)prop-1-yl [sic] |
| 287 | CH₃ | CH₃ | 3-(2'-Cyanophenoxy)prop-1-yl |
| 288 | CH₃ | CH₃ | 3-(3'-Cyanophenoxy)prop-1-yl |
| 289 | CH₃ | CH₃ | 3-(4'-Cyanophenoxy)prop-1-yl |
| 290 | CH₃ | CH₃ | 3-(2'-Methylphenoxy)prop-1-yl |
| 291 | CH₃ | CH₃ | 3-(3'-Methylphenoxy)prop-1-yl |
| 292 | CH₃ | CH₃ | 3-(4'-Methylphenoxy)prop-1-yl |
| 293 | CH₃ | CH₃ | 3-(2'-Methoxyphenoxy)prop-1-yl |
| 294 | CH₃ | CH₃ | 3-(3'-Methoxyphenoxy)prop-1-yl |
| 295 | CH₃ | CH₃ | 3-(4'-Methoxyphenoxy)prop-1-yl |
| 296 | CH₃ | CH₃ | 3-(2'-Trifluoromethylphenoxy)prop-1-yl |
| 297 | CH₃ | CH₃ | 3-(3'-Trifluoromethylphenoxy)prop-1-yl |
| 298 | CH₃ | CH₃ | 3-(4'-TrifluoromethYlphenoxy)prop-1-yl |
| 299 | CH₃ | CH₃ | 4-Phenoxybut-1-yl |
| 300 | CH₃ | CH₃ | 2-Phenyleth-1-yl |
| 301 | CH₃ | CH₃ | 2-(2'-Chlorophenyl)eth-1-yl |
| 302 | CH₃ | CH₃ | 2-(3'-Chlorophenyl)eth-1-yl |
| 303 | CH₃ | CH₃ | 2-(4'-Chlorophenyl)eth-1-yl |
| 304 | CH₃ | CH₃ | 2-(3',5'-Dichlorophenyl)eth-1-yl |
| 305 | CH₃ | CH₃ | 2-(2'-Cyanophenyl)eth-1-yl |
| 306 | CH₃ | CH₃ | 2-(3'-Cyanophenyl)eth-1-yl |
| 307 | CH₃ | CH₃ | 2-(4'-Cyanophenyl)eth-1-yl |
| 308 | CH₃ | CH₃ | 2-(2'-Methylphenyl)eth-1-yl |
| 309 | CH₃ | CH₃ | 2-(3'-Methylphenyl)eth-1-yl |
| 310 | CH₃ | CH₃ | 2-(4'-Methylphenyl)eth-1-yl |
| 311 | CH₃ | CH₃ | 2-(2'-Methoxyphenyl)eth-1-yl |
| 312 | CH₃ | CH₃ | 2-(3'-Methoxyphenyl)eth-1-yl |
| 313 | CH₃ | CH₃ | 2-(4'-Methoxyphenyl)eth-1-yl |
| 314 | CH₃ | CH₃ | 2-(2'-Trifluoromethylphenyl)eth-1-yl |
| 315 | CH₃ | CH₃ | 2-(3'-Trifluoromethylphenyl)eth-1-yl |
| 316 | CH₃ | CH₃ | 2-(4'-Trifluoromethylphenyl)eth-1-yl |
| 317 | CH₃ | CH₃ | 3-Phenylprop-1-yl |
| 318 | CH₃ | CH₃ | 3-(2'-Chlorophenyl)prop-1-yl |
| 319 | CH₃ | CH₃ | 3-(3'-Chlorophenyl)prop-1-yl |
| 320 | CH₃ | CH₃ | 3-(4'-Chlorophenyl)prop-1-yl |
| 321 | CH₃ | CH₃ | 3-(2'-Cyanophenyl)prop-1-yl |
| 322 | CH₃ | CH₃ | 3-(3'-Cyanophenyl)prop-1-yl |
| 323 | CH₃ | CH₃ | 3-(4'-Cyanophenyl)prop-1-yl |
| 324 | CH₃ | CH₃ | 3-(2'-Trifluoromethylphenyl)prop-1-yl |
| 325 | CH₃ | CH₃ | 4-Phenylbut-1-yl |
| 326 | CH₃ | CH₃ | 4-(4'-Chlorophenyl)but-1-yl |
| 327 | CH₃ | CH₃ | 6-(4'-Chlorophenyl)hex-1-yl |
| 328 | CH₃ | CH₃ | 2-Pyridylmethyl |
| 329 | CH₃ | CH₃ | 3-Pyridylmethyl |
| 330 | CH₃ | CH₃ | 4-Pyridylmethyl |
| 331 | CH₃ | CH₃ | 4-Chloropyridin-2-ylmethyl |
| 332 | CH₃ | CH₃ | 5-Chloropyridin-2-ylmethyl |
| 333 | CH₃ | CH₃ | 6-Chloropyridin-2-ylmethyl |
| 334 | CH₃ | CH₃ | 5-Chloropyridin-3-ylmethyl |
| 335 | CH₃ | CH₃ | 6-Chloropyridin-3-ylmethyl |
| 336 | CH₃ | CH₃ | 2-Chlropyridin-4-ylmethyl |
| 337 | CH₃ | CH₃ | 2-Pyrimidinylmethyl |
| 338 | CH₃ | CH₃ | 4-Chloropyrimidin-2-ylmethyl |
| 339 | CH₃ | CH₃ | 5-Chloropyrimidin-2-ylmethyl |
| 340 | CH₃ | CH₃ | 2-Chloropyrimidin-4-ylmethyl |
| 341 | CH₃ | CH₃ | 6-Chloropyrimidin-4-ylmethyl |
| 342 | CH₃ | CH₃ | 2-Chloropyrimidin-5-ylmethyl |
| 343 | CH₃ | CH₃ | 4-Pyridazinylmethyl |
| 344 | CH₃ | CH₃ | 2-Pyrazinylmethyl |
| 345 | CH₃ | CH₃ | 5-Chloropyrazin-2-ylmethyl |
| 346 | CH₃ | CH₃ | 6-Chloropyrazin-2-ylmethyl |

TABLE A-continued

| No. | R³ | R⁴ | R⁵ |
|---|---|---|---|
| 347 | CH₃ | CH₃ | 3-Pyridazinylmethyl |
| 348 | CH₃ | CH₃ | 6-Chloropyridazin-3-ylmethyl |
| 349 | CH₃ | CH₃ | 1,3,5-Triazinylmethyl |
| 350 | CH₃ | CH₃ | 2-Furylmethyl |
| 351 | CH₃ | CH₃ | 3-Furylmethyl |
| 352 | CH₃ | CH₃ | 4-Bromofur-2-ylmethyl |
| 353 | CH₃ | CH₃ | 5-Chlorofur-2-ylmethyl |
| 354 | CH₃ | CH₃ | 2-Thienylmethyl |
| 355 | CH₃ | CH₃ | 3-Thienylmethyl |
| 356 | CH₃ | CH₃ | 5-Methylthien-3-ylmethyl |
| 357 | CH₃ | CH₃ | 5-Chlorothien-2-ylmethyl |
| 358 | CH₃ | CH₃ | 2-Chlorothien-4-ylmethyl |
| 359 | CH₃ | CH₃ | 2-Pyrrolylmethyl |
| 360 | CH₃ | CH₃ | 3-Pyrrolylmethyl |
| 361 | CH₃ | CH₃ | 2-Oxazolylmethyl |
| 362 | CH₃ | CH₃ | 4-Methyloxazol-2-ylmethyl |
| 363 | CH₃ | CH₃ | 5-Methyloxazol-2-ylmethyl |
| 364 | CH₃ | CH₃ | 4-Chlorooxazol-2-ylmethyl |
| 365 | CH₃ | CH₃ | 5-Chlorooxazol-2-ylmethyl |
| 366 | CH₃ | CH₃ | 4-Oxazolylmethyl |
| 367 | CH₃ | CH₃ | 2-Methyloxazol-4-ylmethyl |
| 368 | CH₃ | CH₃ | 5-Methyloxazol-4-ylmethyl |
| 369 | CH₃ | CH₃ | 2-Chlorooxazol-4-ylmethyl |
| 370 | CH₃ | CH₃ | 5-Chlorooxazol-4-ylmethyl |
| 371 | CH₃ | CH₃ | 5-Oxazolylmethyl |
| 372 | CH₃ | CH₃ | 2-Methyloxazol-5-ylmethyl |
| 373 | CH₃ | CH₃ | 4-Methyloxazol-5-ylmethyl |
| 374 | CH₃ | CH₃ | 2-Chlorooxazol-5-ylmethyl |
| 375 | CH₃ | CH₃ | 4-Chlorooxazol-5-ylmethyl |
| 376 | CH₃ | CH₃ | 2-Thiazolylmethyl |
| 377 | CH₃ | CH₃ | 4-Methylthiazol-2-ylmethyl |
| 378 | CH₃ | CH₃ | 5-Methylthiazol-2-ylmethyl |
| 379 | CH₃ | CH₃ | 4-Chlorothiazol-2-ylmethyl |
| 380 | CH₃ | CH₃ | 5-Chlorothiazol-2-ylmethyl |
| 381 | CH₃ | CH₃ | 4-Thiazolylmethyl |
| 382 | CH₃ | CH₃ | 2-Methylthiazol-4-ylmethyl |
| 383 | CH₃ | CH₃ | 5-Methylthiazol-4-ylmethyl |
| 384 | CH₃ | CH₃ | 2-Chlorothiazol-4-ylmethyl |
| 385 | CH₃ | CH₃ | 5-Chlorothiazol-4-ylmethyl |
| 386 | CH₃ | CH₃ | 5-Thiazolylmethyl |
| 387 | CH₃ | CH₃ | 2-Methylthiazol-5-ylmethyl |
| 388 | CH₃ | CH₃ | 4-Methylthiazol-5-ylmethyl |
| 389 | CH₃ | CH₃ | 2-Chlorothiazol-5-ylmethyl |
| 390 | CH₃ | CH₃ | 4-Chlorothiazol-5-ylmethyl |
| 391 | CH₃ | CH₃ | 3-Isoxazolylmethyl |
| 392 | CH₃ | CH₃ | 4-Methylisoxazol-3-ylmethyl |
| 393 | CH₃ | CH₃ | 5-Methylisoxazol-3-ylmethyl |
| 394 | CH₃ | CH₃ | 4-Chloroisoxazol-3-ylmethyl |
| 395 | CH₃ | CH₃ | 5-Chloroisoxazol-3-ylmethyl |
| 396 | CH₃ | CH₃ | 4-Isoxazolylmethyl |
| 397 | CH₃ | CH₃ | 3-Methylisoxazol-4-ylmethyl |
| 398 | CH₃ | CH₃ | 5-Methylisoxazol-4-ylmethyl |
| 399 | CH₃ | CH₃ | 3-Chloroisoxazol-4-ylmethyl |
| 400 | CH₃ | CH₃ | 5-Chloroisoxazol-4-Y1methyl |
| 401 | CH₃ | CH₃ | 5-Isoxazolylmethyl |
| 402 | CH₃ | CH₃ | 3-Methylisoxazol-5-ylmethyl |
| 403 | CH₃ | CH₃ | 4-Methylisoxazol-5-ylmethyl |
| 404 | CH₃ | CH₃ | 3-Chloroisoxazol-5-ylmethyl |
| 405 | CH₃ | CH₃ | 4-Chloroisoxazol-5-ylmethyl |
| 406 | CH₃ | CH₃ | 3-Isothiazolylmethyl |
| 407 | CH₃ | CH₃ | 4-Methylisothiazol-3-ylmethyl |
| 408 | CH₃ | CH₃ | 5-Methylisothiazol-3-ylmethyl |
| 409 | CH₃ | CH₃ | 4-Chloroisothiazol-3-ylmethyl |
| 410 | CH₃ | CH₃ | 5-Chloroisothiazol-3-ylmethyl |
| 411 | CH₃ | CH₃ | 4-Isothiazolylmethyl |
| 412 | CH₃ | CH₃ | 3-Methylisothiazol-4-ylmethyl |
| 413 | CH₃ | CH₃ | 5-Methylisothiazol-4-ylmethyl |
| 414 | CH₃ | CH₃ | 3-Chloroisothiazol-4-ylmethyl |
| 415 | CH₃ | CH₃ | 5-Chloroisothiazol-4-ylmethyl |
| 416 | CH₃ | CH₃ | 5-Isothiazolylmethyl |
| 417 | CH₃ | CH₃ | 3-Methylisothiazol-5-ylmethyl |
| 418 | CH₃ | CH₃ | 4-Methylisothiazol-5-ylmethyl |
| 419 | CH₃ | CH₃ | 3-Chloroisothiazol-5-ylmethyl |
| 420 | CH₃ | CH₃ | 4-Chloroisothiazol-5-ylmethyl |
| 421 | CH₃ | CH₃ | 4-Imidazolylmethyl |
| 422 | CH₃ | CH₃ | 1-Phenylpyrazol-3-ylmethyl |
| 423 | CH₃ | CH₃ | 1-Methylimidazol-4-ylmethyl |

TABLE A-continued

| No. | R³ | R⁴ | R⁵ |
|---|---|---|---|
| 424 | CH₃ | CH₃ | 1-Phenyl-1,2,4-triazol-3-ylmethyl |
| 425 | CH₃ | CH₃ | 1,2,4-Oxadiazol-3-ylmethyl |
| 426 | CH₃ | CH₃ | 5-Chloro-1,2,4-oxadiazol-3-ylmethyl |
| 427 | CH₃ | CH₃ | 5-Methyl-1,2,4-oxadiazol-3-ylmethyl |
| 428 | CH₃ | CH₃ | 5-Trifluoromethyl-1,2,4-oxadiazol-3-ylmethyl |
| 429 | CH₃ | CH₃ | 1,3,4-oxadiazol-2-ylmethyl |
| 430 | CH₃ | CH₃ | 5-Chloro-1,3,4-oxadiazol-2-ylmethyl |
| 431 | CH₃ | CH₃ | 5-Methyl-1,3,4-oxadiazol-2-ylmethyl |
| 432 | CH₃ | CH₃ | 5-Methoxy-1,3,4-oxadiazol-2-ylmethyl |
| 433 | CH₃ | CH₃ | 1,2,4-Thiadiazol-3-ylmethyl |
| 434 | CH₃ | CH₃ | 5-Chloro-1,2,4-thiadiazol-3-ylmethyl |
| 435 | CH₃ | CH₃ | 5-Methyl-1,2,4-thiadiazol-3-ylmethyl |
| 436 | CH₃ | CH₃ | 1,3,4-Thiadiazol-2-yl-ethyl |
| 437 | CH₃ | CH₃ | 5-Chloro-1,3,4-thiadiazol-2-ylmethyl |
| 438 | CH₃ | CH₃ | 5-Methyl-1,3,4-thiadiazol-2-ylmethyl |
| 439 | CH₃ | CH₃ | 5-Cyano-1,3,4-thiadiazol-2-ylmethyl |
| 440 | CH₃ | CH₃ | 2-(2'-Pyridinyloxy)eth-1-yl |
| 441 | CH₃ | CH₃ | 2-(3'-Pyridinyloxy)eth-1-yl |
| 442 | CH₃ | CH₃ | 2-(4'-Pyridinyloxy)eth-1-yl |
| 443 | CH₃ | CH₃ | 2-(2'-Pyrimidinyloxy)eth-1-yl |
| 444 | CH₃ | CH₃ | 2-(4'-Pyrimidinyloxy)eth-1-yl |
| 445 | CH₃ | CH₃ | 2-(5'-Pyrimidinyloxy)eth-1-yl |
| 446 | CH₃ | CH₃ | 2-(2'-Pyrazinyloxy)eth-1-yl |
| 447 | CH₃ | CH₃ | 2-(2'-Pyridazinyloxy)eth-1yl |
| 448 | CH₃ | CH₃ | 2-(3'-Pyridazinyloxy)eth-1-yl |
| 449 | CH₃ | CH₃ | 2-(1',3',5'-Triazinyloxy)eth-1-yl |
| 450 | CH₃ | CH₃ | 2-(5'-Methylisoxazol-3'-yloxy)eth-1-yl |
| 451 | CH₃ | CH₃ | 2-(5'-Chloroisoxazol-3'-yloxy)eth-1-yl |
| 452 | CH₃ | CH₃ | 2-(2'-Methoxythiazol-4'-yloxy)eth-1-yl |
| 453 | CH₃ | CH₃ | 2-(4'-Chlorooxazol-2'-yloxy)eth-1-yl |
| 454 | CH₃ | CH₃ | 2-(1'-Phenyl-1'H-1',2',4'-triazol-3'-yloxy)ethl-yl |
| 455 | CH₃ | CH₃ | 2-(1'-Phenylpyrazol-3'-yloxy)eth-1-yl |
| 456 | CH₃ | CH₃ | C₆H₅ |
| 457 | CH₃ | CH₃ | 2-Cl—C₆H₄ |
| 458 | CH₃ | CH₃ | 3-Cl—C₆H₄ |
| 459 | CH₃ | CH₃ | 4-Cl—C₆H₄ |
| 460 | CH₃ | CH₃ | 2,3-Cl₂—C₆H₃ |
| 461 | CH₃ | CH₃ | 2,4-Cl₂—C₆H₃ |
| 462 | CH₃ | CH₃ | 2,5-Cl₂—C₆H₃ |
| 463 | CH₃ | CH₃ | 3,4-Cl₂—C₆H₃ |
| 464 | CH₃ | CH₃ | 3,5-Cl₂—C₆H₃ |
| 465 | CH₃ | CH₃ | 4-CN—C₆H₄ |
| 466 | CH₃ | CH₃ | 2-NO₂—C₆H₄ |
| 467 | CH₃ | CH₃ | 3-NO₂—C₆H₄ |
| 468 | CH₃ | CH₃ | 4-NO₂—C₆H₄ |
| 469 | CH₃ | CH₃ | 2,4-(NO₂)₂—C₆H₃ |
| 470 | CH₃ | CH₃ | 2-CH₃—C₆H₄ |
| 471 | CH₃ | CH₃ | 3-CH₃—C₆H₄ |
| 472 | CH₃ | CH₃ | 4-CH₃—C₆H₄ |
| 473 | CH₃ | CH₃ | 2,3-(CH₃)₂—C₆H₃ |
| 474 | CH₃ | CH₃ | 2,4-(CH₃)₂—C₆H₃ |
| 475 | CH₃ | CH₃ | 2,5-(CH₃)₂—C₆H₃ |
| 476 | CH₃ | CH₃ | 2,6-(CH₃)₂—C₆H₃ |
| 477 | CH₃ | CH₃ | 2-C₆H₅—C₆H₄ |
| 478 | CH₃ | CH₃ | 3-C₆H₅—C₆H₄ |
| 479 | CH₃ | CH₃ | 4-C₆H₅—C₆H₄ |
| 480 | CH₃ | CH₃ | 3-OCH₃—C₆H₄ |
| 481 | CH₃ | CH₃ | 4-OCH₃—C₆H₄ |
| 482 | CH₃ | CH₃ | 3-Acetyl-C₆H₄ |
| 483 | CH₃ | CH₃ | 4-Acetyl-C₆H₄ |
| 484 | CH₃ | CH₃ | 3-Methoxycarbonyl-C₆H₄ |
| 485 | CH₃ | CH₃ | 4-Methoxycarbonyl-C₆H₄ |
| 486 | CH₃ | CH₃ | 3-CF₃—C₆H₄ |
| 487 | CH₃ | CH₃ | 4-CF₃—C₆H₄ |
| 488 | CH₃ | CH₃ | 2-Naphthyl |
| 489 | CH₃ | CH₃ | 6-Chloropyridazin-3-yl |
| 490 | CH₃ | CH₃ | 5-Chloropyrazin-2-yl |
| 491 | CH₃ | CH₃ | Quinolin-2-yl |
| 492 | CH₃ | CH₃ | 2,5-Dimethylpyrazin-3-yl |
| 493 | CH₃ | CH₃ | Pyrazin-2-yl |
| 494 | CH₃ | CH₃ | 3-Chloropyrid-2-yl |
| 495 | CH₃ | CH₃ | 6-Chloropyrid-2-yl |
| 496 | CH₃ | CH₃ | 4-Trifluoromethyl, 6-Chloropyrid-2-yl |
| 497 | CH₃ | CH₃ | 4-Trifluoromethylpyrid-2-yl |
| 498 | CH₃ | CH₃ | 6-Trifluoromethylpyrid-2-yl |
| 499 | CH₃ | CH₃ | 6-Methoxypyrid-2-yl |
| 500 | CH₃ | CH₃ | 5-Chloropyrid-2-yl |

TABLE A-continued

| No. | R³ | R⁴ | R⁵ |
|---|---|---|---|
| 501 | CH₃ | CH₃ | Pyrid-2-yl |
| 502 | CH₃ | CH₃ | Benzothiazol-2-yl |
| 503 | CH₃ | CH₃ | 7-Chloroquinolin-4-yl |
| 504 | CH₃ | CH₃ | 3-Nitropyrid-2-yl |
| 505 | CH₃ | CH₃ | Pyrrol-3-yl |
| 506 | CH₃ | CH₃ | Pyrrol-2-yl |
| 507 | CH₃ | CH₃ | 2,6-Dioctylpyrid-4-yl |
| 508 | CH₃ | CH₃ | 5-Nitropyrid-2-yl |
| 509 | CH₃ | CH₃ | Pyrid-4-yl |
| 510 | CH₃ | CH₃ | Pyrid-3-yl |
| 511 | CH₃ | CH₃ | Pyrimidin-2-yl |
| 512 | CH₃ | CH₃ | Pyrimidin-4-yl |
| 513 | CH₃ | CH₃ | Ouinazolin-4-yl |
| 514 | CH₃ | CH₃ | 6-Chloropyrimidin-4-yl |
| 515 | CH₃ | CH₃ | 6-Methoxypyrimidin-4-yl |
| 516 | CH₃ | CH₃ | 2,5,6-Trichloropyrimidin-4-yl |
| 517 | CH₃ | CH₃ | 2,6-Dimethylpyrimidin-4-yl |
| 518 | CH₃ | CH₃ | 2-Methyl, 6-Chloropyrimidin-4-yl |
| 519 | CH₃ | CH₃ | 2-Methyl, 6-Ethoxypyrimidin-4-yl |
| 520 | CH₃ | CH₃ | 4,5,6-Trichloropyrimidin-2-yl |
| 521 | CH₃ | CH₃ | 4,6-Dimethoxypyrimidin-2-yl |
| 522 | CH₃ | CH₃ | 4,6-Dimethylpyrimidin-2-yl |
| 523 | CH₃ | CH₃ | 4,6-Dich1oropyrimidin-2-yl |
| 524 | CH₃ | CH₃ | 4-Methyl, 6-Methoxypyrimidin-2-yl |
| 525 | CH₃ | CH₃ | 4-Chloro, 6-Methoxypyrimidin-2-yl |
| 526 | CH₃ | CH₃ | 6-Chloroquinoxalin-2-yl |
| 527 | CH₃ | CH₃ | 3,6-Dichloro-1,2,4-triazin-5-yl |
| 528 | CH₃ | CH₃ | 4-Methoxy-1,3,5-triazin-2-yl |
| 529 | CH₃ | CH₃ | 4-Ethoxy-1,3,5-triazin-2-yl |
| 530 | CH₃ | CH₃ | 4,6-Dichloro-1,3,5-triazin-2-yl |
| 531 | CH₃ | CH₃ | 4-Ethoxy,6-Chloro-1,3,5-triazin-2-yl |
| 532 | CH₃ | CH₃ | Isoxazol-3-yl |
| 533 | CH₃ | CH₃ | Thien-2-yl |
| 534 | CH₃ | CH₃ | Fur-2-yl |
| 535 | CH₃ | CH₃ | Thiatriazol-5-yl |
| 536 | CH₃ | CH₃ | (E)-1-Chloropropen-3-yl |
| 537 | CH₃ | CH₃ | (E)-4-(4'-Chlorophenyl)but-2-en-1-yl |
| 538 | CH₃ | CH₃ | Propyn-3-yl |
| 539 | CH₃ | CH₃ | Methylcarbonyl |
| 540 | CH₃ | CH₃ | Ethylcarbonyl |
| 541 | CH₃ | CH₃ | n-Propylcarbonyl |
| 542 | CH₃ | CH₃ | i-Propylcarbonyl |
| 543 | CH₃ | CH₃ | n-Butylcarbonyl |
| 544 | CH₃ | CH₃ | s-Butylcarbonyl |
| 545 | CH₃ | CH₃ | i-Butylcarbonyl |
| 546 | CH₃ | CH₃ | t-Butylcarbonyl |
| 547 | CH₃ | CH₃ | n-Pentylcarbonyl |
| 548 | CH₃ | CH₃ | i-Pentylcarbonyl |
| 549 | CH₃ | CH₃ | neo-Pentylcarbonyl |
| 550 | CH₃ | CH₃ | n-Hexylcarbonyl |
| 551 | CH₃ | CH₃ | n-Octylcarbonyl |
| 552 | CH₃ | CH₃ | 1-Propenylcarbonyl |
| 553 | CH₃ | CH₃ | 2-Penten-1-yl-carbonyl |
| 554 | CH₃ | CH₃ | 2,5-Heptadien-1-yl-carbonyl |
| 555 | CH₃ | CH₃ | Benzoyl |
| 556 | CH₃ | CH₃ | 2-Chlorobenzoyl |
| 557 | CH₃ | CH₃ | 3-Chlorobenzoyl |
| 558 | CH₃ | CH₃ | 4-Chlorobenzoyl |
| 559 | CH₃ | CH₃ | 2-Cyanobenzoyl |
| 560 | CH₃ | CH₃ | 3-Cyanobenzoyl |
| 561 | CH₃ | CH₃ | 4-Cyanobenzoyl |
| 562 | CH₃ | CH₃ | 4-Methoxybenzoyl |
| 563 | CH₃ | CH₃ | 2-Pyridylcarbonyl |
| 564 | CH₃ | CH₃ | 3-Pyridylcarbonyl |
| 565 | CH₃ | CH₃ | 4-Pyridylcarbonyl |
| 566 | CH₃ | CH₃ | 2-Pyrimidinylcarbonyl |
| 567 | CH₃ | CH₃ | 2-Oxazolylcarbonyl |
| 568 | CH₃ | CH₃ | 4-Methylisoxazol-5-ylcarbonyl |
| 569 | CH₃ | CH₃ | Methylsulfonyl |
| 570 | CH₃ | CH₃ | Ethylsulfonyl |
| 571 | CH₃ | CH₃ | n-Propylsulfonyl |
| 572 | CH₃ | CH₃ | i-Propylsulfonyl |
| 573 | CH₃ | CH₃ | n-Butylsulfonyl |
| 574 | CH₃ | CH₃ | t-Butylsulfonyl |
| 575 | CH₃ | CH₃ | n-Pentylsulfonyl |
| 576 | CH₃ | CH₃ | neo-Pentylsulfonyl |
| 577 | CH₃ | CH₃ | n-Hexylsulfonyl |

TABLE A-continued

| No. | R³ | R⁴ | R⁵ |
|---|---|---|---|
| 578 | CH₃ | CH₃ | n-Octylsulfonyl |
| 579 | CH₃ | CH₃ | Phenylsulfonyl |
| 580 | CH₃ | CH₃ | 2-Chlorophenylsulfonyl |
| 581 | CH₃ | CH₃ | 3-Chlorophenylsulfonyl |
| 582 | CH₃ | CH₃ | 4-Chlorophenylsulfonyl |
| 583 | CH₃ | CH₃ | 2-Cyanophenylsulfonyl |
| 584 | CH₃ | CH₃ | 3-Cyanophenylsulfonyl |
| 585 | CH₃ | CH₃ | 4-Cyanophenylsulfonyl |
| 586 | CH₃ | CH₃ | 2-Pyridylsulfonyl |
| 587 | CH₃ | CH₃ | 3-Pyridylsulfonyl |
| 588 | CH₃ | CH₃ | 4-Pyridylsulfonyl |
| 589 | CH₃ | CH₃ | 2-Pyrimidinylsulfonyl |
| 590 | CH₃ | CH₃ | 4-Oxazolylsulfonyl |
| 591 | CH₃ | CH₃ | 5-Chlorothiazol-2ylsulfonyl [sic] |
| 592 | CH₃ | CH₃ | 2-t-C₄H₉—C₆H₄—CH₂ |
| 593 | CH₃ | CH₃ | 3-t-C₄H₉—C₆H₄—CH₂ |
| 594 | CH₃ | CH₃ | 4-t-C₄H₉—C₆H₄—CH₂ |
| 595 | CH₃ | CH₃ | 2-(4'-Chlorothiazol-2'-yloxy)eth-1-yl |
| 596 | CH₃ | CH₃ | 2-(1'-Methylpyrazol-4'-yloxy)eth-1-yl |
| 597 | CH₃ | CH₃ | 4-Br—C₆H₄ |
| 598 | CH₃ | CH₃ | 3,5-(CH₃)₂—C₆H₃ |
| 599 | CH₃ | CH₃ | 4-C₂H₅—C₆H₄ |
| 600 | CH₃ | CH₃ | 3-Dimethylaminocarbonyl-C₆H₄ |
| 601 | CH₃ | CH₃ | 4-Dimethylaminocarbonyl-C₆H₄ |
| 602 | CH₃ | CH₃ | 2-Hydroxyprop-1-yl |
| 603 | CH₃ | CH₃ | 6-Hydroxy-2-methylpyrimidin-4-ylmethyl |
| 604 | CH₃ | CH₃ | [6-OH,2-CH(CH₃)₂-pyrimidin-4-yl]-CH₂ |
| 605 | CH₃ | CH₃ | [6-OH,2-CH(CH₂)₂-pyrimidin-4-yl]-CH₂ |
| 606 | CH₃ | CH₃ | 5-(2'-Furan)pent-1-yl |
| 607 | CH₃ | CH₃ | 5-(2'-N-Methylpyrrol)pent-1-yl |
| 608 | CH₃ | CH₃ | [2-(4-Cl—C₆H₄)oxazol-4-yl]-CH₂ |
| 609 | CH₃ | CH₃ | 3-CF₃-pyridin-2-yl |
| 610 | CH₃ | CH₃ | 5-CF₃-pyridin-2-yl |
| 611 | CH₃ | CH₃ | 6-(2'-Thienyl)hex-1-yl |
| 612 | CH₃ | t-C₄H₉ | H |
| 613 | CH₃ | t-C₄H₉ | CH₃ |
| 614 | CH₃ | t-C₄H₉ | C₂H₅ |
| 615 | CH₃ | t-C₄H₉ | n-C₃H₇ |
| 616 | CH₃ | t-C₄H₉ | i-C₃H₇ |
| 617 | CH₃ | t-C₄H₉ | Cyclopropyl |
| 618 | CH₃ | t-C₄H₉ | n-C₄H₉ |
| 619 | CH₃ | t-C₄H₉ | t-C₄H₉ |
| 620 | CH₃ | t-C₄H₉ | n-C₆H₁₃ |
| 621 | CH₃ | t-C₄H₉ | (E)-1-Chloropropen-3-yl |
| 622 | CH₃ | t-C₄H₉ | Propyn-3-yl |
| 623 | CH₃ | t-C₄H₉ | 3-Methylbut-2-en-1-yl |
| 624 | CH₃ | t-C₄H₉ | 2-Naphthyl-CH₂ |
| 625 | CH₃ | t-C₄H₉ | 4-Cl—C₆H₄—CH₂ |
| 626 | CH₃ | t-C₄H₉ | (E)-4-(4'-Chlorophenyl)but-2-en-1-yl |
| 627 | CH₃ | t-C₄H₉ | 6-(4'-Chlorophenyl)hex-1-yl |
| 628 | CH₃ | t-C₄H₉ | 3-CF₃—C₆H₄ |
| 629 | CH₃ | C₆H₅ | H |
| 630 | CH₃ | C₆H₅ | CH₃ |
| 631 | CH₃ | C₆H₅ | C₂H₅ |
| 632 | CH₃ | C₆H₅ | n-C₃H₇ |
| 633 | CH₃ | C₆H₅ | i-C₃H₇ |
| 634 | CH₃ | C₆H₅ | Cyclopropyl |
| 635 | CH₃ | C₆H₅ | n-C₄H₉ |
| 636 | CH₃ | C₆H₅ | t-C₄H₉ |
| 637 | CH₃ | C₆H₅ | n-C₆H₁₃ |
| 638 | CH₃ | C₆H₅ | 4-Cl—C₆H₄—CH₂ |
| 639 | CH₃ | C₆H₅ | 3-CF₃—C₆H₄ |
| 640 | CH₃ | C₆H₅ | 6-(4'-Chlorophenyl)hex-1-yl |
| 641 | CH₃ | C₆H₅ | (E)-4-(4'-Chlorophenyl)but-2-en-1-yl |
| 642 | CH₃ | H | H |
| 643 | CH₃ | H | CH₃ |
| 644 | CH₃ | H | C₂H₅ |
| 645 | CH₃ | H | n-C₃H₇ |
| 646 | CH₃ | H | i-C₃H₇ |
| 647 | CH₃ | OH | H |
| 648 | CH₃ | OH | CH₃ |
| 649 | CH₃ | OH | C₂H₅ |
| 650 | CH₃ | OH | n-C₃H₇ |
| 651 | CH₃ | OH | i-C₃H₇ |
| 652 | CH₃ | Cl | CH₃ |
| 653 | CH₃ | Cl | C₂H₅ |
| 654 | CH₃ | Cl | n-C₃H₇ |

TABLE A-continued

| No. | R³ | R⁴ | R⁵ |
|---|---|---|---|
| 655 | $CH_3$ | Cl | $i\text{-}C_3H_7$ |
| 656 | $CH_3$ | $OCH_3$ | H |
| 657 | $CH_3$ | $OCH_3$ | $CH_3$ |
| 658 | $CH_3$ | $OCH_3$ | $C_2H_5$ |
| 659 | $CH_3$ | $OCH_3$ | $n\text{-}C_3H_7$ |
| 660 | $CH_3$ | $OCH_3$ | $i\text{-}C_3H_7$ |
| 661 | $CH_3$ | $SCH_3$ | H |
| 662 | $CH_3$ | $SCH_3$ | $CH_3$ |
| 663 | $CH_3$ | $SCH_3$ | $C_2H_5$ |
| 664 | $CH_3$ | $SCH_3$ | $n\text{-}C_3H_7$ |
| 665 | $CH_3$ | $SCH_3$ | $i\text{-}C_3H_7$ |
| 666 | $CH_3$ | Cyclopropyl | H |
| 667 | $CH_3$ | Cyclopropyl | $CH_3$ |
| 668 | $CH_3$ | Cyclopropyl | $C_2H_5$ |
| 669 | $CH_3$ | Cyclopropyl | $n\text{-}C_3H_7$ |
| 670 | $CH_3$ | Cyclopropyl | $i\text{-}C_3H_7$ |
| 671 | $CH_3$ | 2-Pyridyl | H |
| 672 | $CH_3$ | 2-Pyridyl | $CH_3$ |
| 673 | $CH_3$ | 2-Pyridyl | $C_2H_5$ |
| 674 | $CH_3$ | 2-Pyridyl | $n\text{-}C_3H_7$ |
| 675 | $CH_3$ | 2-Pyridyl | $i\text{-}C_3H_7$ |
| 676 | $CH_3$ | 3-Pyridyl | H |
| 677 | $CH_3$ | 3-Pyridyl | $CH_3$ |
| 678 | $CH_3$ | 3-Pyridyl | $C_2H_5$ |
| 679 | $CH_3$ | 3-Pyridyl | $n\text{-}C_3H_7$ |
| 680 | $CH_3$ | 3-Pyridyl | $i\text{-}C_3H_7$ |
| 681 | $CH_3$ | 4-Pyridyl | H |
| 682 | $CH_3$ | 4-Pyridyl | $CH_3$ |
| 683 | $CH_3$ | 4-Pyridyl | $C_2H_5$ |
| 684 | $CH_3$ | 4-Pyridyl | $n\text{-}C_3H_7$ |
| 685 | $CH_3$ | 4-Pyridyl | $i\text{-}C_3H_7$ |
| 686 | $CH_3$ | 2-Pyridimidyl | H |
| 687 | $CH_3$ | 2-Pyridimidyl | $CH_3$ |
| 688 | $CH_3$ | 2-Pyridimidyl | $C_2H_5$ |
| 689 | $CH_3$ | 2-Pyridimidyl | $n\text{-}C_3H_7$ |
| 690 | $CH_3$ | 2-Pyridimidyl | $i\text{-}C_3H_7$ |
| 691 | $CH_3$ | 4-Pyridimidyl [sic] | H |
| 692 | $CH_3$ | 4-Pyridimidyl | $CH_3$ |
| 693 | $CH_3$ | 4-Pyridimidyl | $C_2H_5$ |
| 694 | $CH_3$ | 4-Pyridimidyl | $n\text{-}C_3H_7$ |
| 695 | $CH_3$ | 4-Pyridimidyl | $i\text{-}C_3H_7$ |
| 696 | $CH_3$ | 5-Pyridimidyl | H |
| 697 | $CH_3$ | 5-Pyridimidyl | $CH_3$ |
| 698 | $CH_3$ | 5-Pyridimidyl | $C_2H_5$ |
| 699 | $CH_3$ | 5-Pyridimidyl | $n\text{-}C_3H_7$ |
| 700 | $CH_3$ | 5-Pyridimidyl | $i\text{-}C_3H_7$ |
| 701 | $CH_3$ | 1,3,5-Triazinyl | H |
| 702 | $CH_3$ | 1,3,5-Triazinyl | $CH_3$ |
| 703 | $CH_3$ | 1,3,5-Triazinyl | $C_2H_5$ |
| 704 | $CH_3$ | 1,3,5-Triazinyl | $n\text{-}C_3H_7$ |
| 705 | $CH_3$ | 1,3,5-Triazinyl | $i\text{-}C_3H_7$ |
| 706 | $CH_3$ | 2-Furyl | H |
| 707 | $CH_3$ | 2-Furyl | $CH_3$ |
| 708 | $CH_3$ | 2-Furyl | $C_2H_5$ |
| 709 | $CH_3$ | 2-Furyl | $n\text{-}C_3H_7$ |
| 710 | $CH_3$ | 2-Furyl | $i\text{-}C_3H_7$ |
| 711 | $CH_3$ | 3-Furyl | H |
| 712 | $CH_3$ | 3-Furyl | $CH_3$ |
| 713 | $CH_3$ | 3-Furyl | $C_2H_5$ |
| 714 | $CH_3$ | 3-Furyl | $n\text{-}C_3H_7$ |
| 715 | $CH_3$ | 3-Furyl | $i\text{-}C_3H_7$ |
| 716 | $CH_3$ | 2-Thienyl | H |
| 717 | $CH_3$ | 2-Thienyl | $CH_3$ |
| 718 | $CH_3$ | 2-Thienyl | $C_2H_5$ |
| 719 | $CH_3$ | 2-Thienyl | $n\text{-}C_3H_7$ |
| 720 | $CH_3$ | 2-Thienyl | $i\text{-}C_3H_7$ |
| 721 | $CH_3$ | 3-Thienyl | H |
| 722 | $CH_3$ | 3-Thienyl | $CH_3$ |
| 723 | $CH_3$ | 3-Thienyl | $C_2H_5$ |
| 724 | $CH_3$ | 3-Thienyl | $n\text{-}C_3H_7$ |
| 725 | $CH_3$ | 3-Thienyl | $i\text{-}C_3H_7$ |
| 726 | $CH_3$ | 2-Oxazolyl | H |
| 727 | $CH_3$ | 2-Oxazolyl | $CH_3$ |
| 728 | $CH_3$ | 2-Oxazolyl | $C_2H_5$ |
| 729 | $CH_3$ | 2-Oxazolyl | $n\text{-}C_3H_7$ |
| 730 | $CH_3$ | 2-Oxazolyl | $i\text{-}C_3H_7$ |
| 731 | $CH_3$ | 4-Oxazolyl | H |

TABLE A-continued

| No. | R³ | R⁴ | R⁵ |
|---|---|---|---|
| 732 | CH₃ | 4-Oxazolyl | CH₃ |
| 733 | CH₃ | 4-Oxazolyl | C₂H₅ |
| 734 | CH₃ | 4-Oxazolyl | n-C₃H₇ |
| 735 | CH₃ | 4-Oxazolyl | i-C₃H₇ |
| 736 | CH₃ | 2-Thiazolyl | H |
| 737 | CH₃ | 2-Thiazolyl | CH₃ |
| 738 | CH₃ | 2-Thiazolyl | C₂H₅ |
| 739 | CH₃ | 2-Thiazolyl | n-C₃H₇ |
| 740 | CH₃ | 2-Thiazolyl | i-C₃H₇ |
| 741 | CH₃ | 4-Thiazolyl | H |
| 742 | CH₃ | 4-Thiazolyl | CH₃ |
| 743 | CH₃ | 4-Thiazolyl | C₂H₅ |
| 744 | CH₃ | 4-Thiazolyl | n-C₃H₇ |
| 745 | CH₃ | 4-Thiazolyl | i-C₃H₇ |
| 746 | CH₃ | 3-Isoxazolyl | H |
| 747 | CH₃ | 3-Isoxazolyl | CH₃ |
| 748 | CH₃ | 3-Isoxazolyl | C₂H₅ |
| 749 | CH₃ | 3-Isoxazolyl | n-C₃H₇ |
| 750 | CH₃ | 3-Isoxazolyl | i-C₃H₇ |
| 751 | CH₃ | 5-Isoxazolyl | H |
| 752 | CH₃ | 5-Isoxazolyl | CH₃ |
| 753 | CH₃ | 5-Isoxazolyl | C₂H₅ |
| 754 | CH₃ | 5-Isoxazolyl | n-C₃H₇ |
| 755 | CH₃ | 5-Isoxazolyl | i-C₃H₇ |
| 756 | CH₃ | 2-Imidazolyl | H |
| 757 | CH₃ | 2-Imidazolyl | CH₃ |
| 758 | CH₃ | 2-Imidazolyl | C₂H₅ |
| 759 | CH₃ | 2-Imidazolyl | n-C₃H₇ |
| 760 | CH₃ | 2-Imidazolyl | i-C₃H₇ |
| 761 | CH₃ | 3-Pyrazolyl | H |
| 762 | CH₃ | 3-Pyrazolyl | CH₃ |
| 763 | CH₃ | 3-Pyrazolyl | C₂H₅ |
| 764 | CH₃ | 3-Pyrazolyl | n-C₃H₇ |
| 765 | CH₃ | 3-Pyrazolyl | i-C₃H₇ |
| 766 | CH₃ | 4-Pyrazolyl | H |
| 767 | CH₃ | 4-Pyrazolyl | CH₃ |
| 768 | CH₃ | 4-Pyrazolyl | C₂H₅ |
| 769 | CH₃ | 4-Pyrazolyl | n-C₃H₇ |
| 770 | CH₃ | 4-Pyrazolyl | i-C₃H₇ |
| 771 | OCH₃ | H | H |
| 772 | OCH₃ | H | CH₃ |
| 773 | OCH₃ | H | C₂H₅ |
| 774 | OCH₃ | H | n-C₃H₇ |
| 775 | OCH₃ | H | i-C₃H₇ |
| 776 | OCH₃ | OH | H |
| 777 | OCH₃ | OH | CH₃ |
| 778 | OCH₃ | OH | C₂H₅ |
| 779 | OCH₃ | OH | n-C₃H₇ |
| 780 | OCH₃ | OH | i-C₃H₇ |
| 781 | OCH₃ | Cl | n-C₄H₉ |
| 782 | OCH₃ | Cl | CH₃ |
| 783 | OCH₃ | Cl | C₂H₅ |
| 784 | OCH₃ | Cl | n-C₃H₇ |
| 785 | OCH₃ | Cl | i-C₃H₇ |
| 786 | OCH₃ | OCH₃ | H |
| 787 | OCH₃ | OCH₃ | CH₃ |
| 788 | OCH₃ | OCH₃ | C₂H₅ |
| 789 | OCH₃ | OCH₃ | n-C₃H₇ |
| 790 | OCH₃ | OCH₃ | i-C₃H₇ |
| 791 | OCH₃ | SCH₃ | H |
| 792 | OCH₃ | SCH₃ | CH₃ |
| 793 | OCH₃ | SCH₃ | C₂H₅ |
| 794 | OCH₃ | SCH₃ | n-C₃H₇ |
| 795 | OCH₃ | SCH₃ | i-C₃H₇ |
| 796 | OCH₃ | CH₃ | H |
| 797 | OCH₃ | CH₃ | CH₃ |
| 798 | OCH₃ | CH₃ | C₂H₅ |
| 799 | OCH₃ | CH₃ | n-C₃H₇ |
| 800 | OCH₃ | CH₃ | i-C₃H₇ |
| 801 | OCH₃ | Cyclopropyl | H |
| 802 | OCH₃ | Cyclopropyl | CH₃ |
| 803 | OCH₃ | Cyclopropyl | C₂H₅ |
| 804 | OCH₃ | Cyclopropyl | n-C₃H₇ |
| 805 | OCH₃ | Cyclopropyl | i-C₃H₇ |
| 806 | OCH₃ | 2-Pyridyl | H |
| 807 | OCH₃ | 2-Pyridyl | CH₃ |
| 808 | OCH₃ | 2-Pyridyl | C₂H₅ |

TABLE A-continued

| No. | R³ | R⁴ | R⁵ |
|---|---|---|---|
| 809 | OCH₃ | 2-Pyridyl | n-C₃H₇ |
| 810 | OCH₃ | 2-Pyridyl | i-C₃H₇ |
| 811 | OCH₃ | 3-Pyridyl | H |
| 812 | OCH₃ | 3-Pyridyl | CH₃ |
| 813 | OCH₃ | 3-Pyridyl | C₂H₅ |
| 814 | OCH₃ | 3-Pyridyl | n-C₃H₇ |
| 815 | OCH₃ | 3-Pyridyl | i-C₃H₇ |
| 816 | OCH₃ | 4-Pyridyl | H |
| 817 | OCH₃ | 4-Pyridyl | CH₃ |
| 818 | OCH₃ | 4-Pyridyl | C₂H₅ |
| 819 | OCH₃ | 4-Pyridyl | n-C₃H₇ |
| 820 | OCH₃ | 4-Pyrimidyl | i-C₃H₇ |
| 821 | OCH₃ | 2-Pyrimidyl | H |
| 822 | OCH₃ | 2-Pyrimidyl | CH₃ |
| 823 | OCH₃ | 2-Pyrimidyl | C₂H₅ |
| 824 | OCH₃ | 2-Pyrimidyl | n-C₃H₇ |
| 825 | OCH₃ | 2-Pyrimidyl | i-C₃H₇ |
| 826 | OCH₃ | 4-Pyrimidyl | H |
| 827 | OCH₃ | 4-Pyrimidyl | CH₃ |
| 828 | OCH₃ | 4-Pyrimidyl | C₂H₅ |
| 829 | OCH₃ | 4-Pyrimidyl | n-C₃H₇ |
| 830 | OCH₃ | 4-Pyrimidyl | i-C₃H₇ |
| 831 | OCH₃ | 5-Pyrimidyl | H |
| 832 | OCH₃ | 5-Pyrimidyl | CH₃ |
| 833 | OCH₃ | 5-Pyrimidyl | C₂H₅ |
| 834 | OCH₃ | 5-Pyrimidyl | n-C₃H₇ |
| 835 | OCH₃ | 5-Pyrimidyl | i-C₃H₇ |
| 836 | OCH₃ | 1,3,5-Triazinyl | H |
| 837 | OCH₃ | 1,3,5-Triazinyl | CH₃ |
| 838 | OCH₃ | 1,3,5-Triazinyl | C₂H₅ |
| 839 | OCH₃ | 1,3,5-Triazinyl | n-C₃H₇ |
| 840 | OCH₃ | 1,3,5-Triazinyl | i-C₃H₇ |
| 841 | OCH₃ | 2-Furyl | H |
| 842 | OCH₃ | 2-Furyl | CH₃ |
| 843 | OCH₃ | 2-Furyl | C₂H₅ |
| 844 | OCH₃ | 2-Furyl | n-C₃H₇ |
| 845 | OCH₃ | 2-Furyl | i-C₃H₇ |
| 846 | OCH₃ | 3-Furyl | H |
| 847 | OCH₃ | 3-Furyl | CH₃ |
| 848 | OCH₃ | 3-Furyl | C₂H₅ |
| 849 | OCH₃ | 3-Furyl | n-C₃H₇ |
| 850 | OCH₃ | 3-Furyl | i-C₃H₇ |
| 851 | OCH₃ | 2-Thienyl | H |
| 852 | OCH₃ | 2-Thienyl | CH₃ |
| 853 | OCH₃ | 2-Thienyl | C₂H₅ |
| 854 | OCH₃ | 2-Thienyl | n-C₃H₇ |
| 855 | OCH₃ | 2-Thienyl | i-C₃H₇ |
| 856 | OCH₃ | 3-Thienyl | H |
| 857 | OCH₃ | 3-Thienyl | CH₃ |
| 858 | OCH₃ | 3-Thienyl | C₂H₅ |
| 859 | OCH₃ | 3-Thienyl | n-C₃H₇ |
| 860 | OCH₃ | 3-Thienyl | i-C₃H₇ |
| 861 | OCH₃ | 2-Oxazolyl | H |
| 862 | OCH₃ | 2-Oxazolyl | CH₃ |
| 863 | OCH₃ | 2-Oxazolyl | C₂H₅ |
| 864 | OCH₃ | 2-Oxazolyl | n-C₃H₇ |
| 865 | OCH₃ | 2-Oxazolyl | i-C₃H₇ |
| 866 | OCH₃ | 4-Oxazolyl | H |
| 867 | OCH₃ | 4-Oxazolyl | CH₃ |
| 868 | OCH₃ | 4-Oxazolyl | C₂H₅ |
| 869 | OCH₃ | 4-Oxazolyl | n-C₃H₇ |
| 870 | OCH₃ | 4-Oxazolyl | i-C₃H₇ |
| 871 | OCH₃ | 2-Thiazolyl | H |
| 872 | OCH₃ | 2-Thiazolyl | CH₃ |
| 873 | OCH₃ | 2-Thiazolyl | C₂H₅ |
| 874 | OCH₃ | 2-Thiazolyl | n-C₃H₇ |
| 875 | OCH₃ | 2-Thiazolyl | i-C₃H₇ |
| 876 | OCH₃ | 4-Thiazdlyl | H |
| 877 | OCH₃ | 4-Thiazolyl | CH₃ |
| 878 | OCH₃ | 4-Thiazolyl | C₂H₅ |
| 879 | OCH₃ | 4-Thiazolyl | n-C₃H₇ |
| 880 | OCH₃ | 4-Thiazolyl | i-C₃H₇ |
| 881 | OCH₃ | 3-Isoxazolyl | H |
| 882 | OCH₃ | 3-Isoxazolyl | CH₃ |
| 883 | OCH₃ | 3-Isoxazolyl | C₂H₅ |
| 884 | OCH₃ | 3-Isoxazolyl | n-C₃H₇ |
| 885 | OCH₃ | 3-Isoxazolyl | i-C₃H₇ |

TABLE A-continued

| No. | R³ | R⁴ | R⁵ |
|---|---|---|---|
| 886 | OCH₃ | 5-Isoxazolyl | H |
| 887 | OCH₃ | 5-Isoxazolyl | CH₃ |
| 888 | OCH₃ | 5-Isoxazolyl | C₂H₅ |
| 889 | OCH₃ | 5-Isoxazolyl | n-C₃H₇ |
| 890 | OCH₃ | 5-Isoxazolyl | i-C₃H₇ |
| 891 | OCH₃ | 2-Imidazolyl | H |
| 892 | OCH₃ | 2-Imidazolyl | CH₃ |
| 893 | OCH₃ | 2-Imidazolyl | C₂H₅ |
| 894 | OCH₃ | 2-Imidazolyl | n-C₃H₇ |
| 895 | OCH₃ | 2-Imidazolyl | i-C₃H₇ |
| 896 | OCH₃ | 3-Pyrazolyl | H |
| 897 | OCH₃ | 3-Pyrazolyl | CH₃ |
| 898 | OCH₃ | 3-Pyrazolyl | C₂H₅ |
| 899 | OCH₃ | 3-Pyrazolyl | n-C₃H₇ |
| 900 | OCH₃ | 3-Pyrazolyl | i-C₃H₇ |
| 901 | OCH₃ | 4-Pyrazolyl | H |
| 902 | OCH₃ | 4-Pyrazolyl | CH₃ |
| 903 | OCH₃ | 4-Pyrazolyl | C₂H₅ |
| 904 | OCH₃ | 4-Pyrazolyl | n-C₃H₇ |
| 905 | OCH₃ | 4-Pyrazolyl | i-C₃H₇ |
| 906 | OH | H | H |
| 907 | OH | H | CH₃ |
| 908 | OH | H | C₂H₅ |
| 909 | OH | H | n-C₃H₇ |
| 910 | OH | H | i-C₃H₇ |
| 911 | OH | OH | H |
| 912 | OH | OH | CH₃ |
| 913 | OH | OH | C₂H₅ |
| 914 | OH | OH | n-C₃H₇ |
| 915 | OH | OH | i-C₃H₇ |
| 916 | OH | Cl | n-C₄H₉ |
| 917 | OH | Cl | CH₃ |
| 918 | OH | Cl | C₂H₅ |
| 919 | OH | Cl | n-C₃H₇ |
| 920 | OH | Cl | i-C₃H₇ |
| 921 | OH | OCH₃ | H |
| 922 | OH | OCH₃ | CH₃ |
| 923 | OH | OCH₃ | C₂H₅ |
| 924 | OH | OCH₃ | n-C₃H₇ |
| 925 | OH | OCH₃ | i-C₃H₇ |
| 926 | OH | SCH₃ | H |
| 927 | OH | SCH₃ | CH₃ |
| 928 | OH | SCH₃ | C₂H₅ |
| 929 | OH | SCH₃ | n-C₃H₇ |
| 930 | OH | SCH₃ | i-C₃H₇ |
| 931 | OH | CH₃ | H |
| 932 | OH | CH₃ | CH₃ |
| 933 | OH | CH₃ | C₂H₅ |
| 934 | OH | CH₃ | n-C₃H₇ |
| 935 | OH | CH₃ | i-C₃H₇ |
| 936 | OH | Cyclopropyl | H |
| 937 | OH | Cyclopropyl | CH₃ |
| 938 | OH | Cyclopropyl | C₂H₅ |
| 939 | OH | Cyclopropyl | n-C₃H₇ |
| 940 | OH | Cyclopropyl | i-C₃H₇ |
| 941 | OH | 2-Pyridyl | H |
| 942 | OH | 2-Pyridyl | CH₃ |
| 943 | OH | 2-Pyridyl | C₂H₅ |
| 944 | OH | 2-Pyridyl | n-C₃H₇ |
| 945 | OH | 2-Pyridyl | i-C₃H₇ |
| 946 | OH | 3-Pyridyl | H |
| 947 | OH | 3-Pyridyl | CH₃ |
| 948 | OH | 3-Pyridyl | C₂H₅ |
| 949 | OH | 3-Pyridyl | n-C₃H₇ |
| 950 | OH | 3-Pyridyl | i-C₃H₇ |
| 951 | OH | 4-Pyridyl | H |
| 952 | OH | 4-Pyridyl | CH₃ |
| 953 | OH | 4-Pyridyl | C₂H₅ |
| 954 | OH | 4-Pyridyl | n-C₃H₇ |
| 955 | OH | 4-Pyridyl | i-C₃H₇ |
| 956 | OH | 2-Pyrimidyl | H |
| 957 | OH | 2-Pyrimidyl | CH₃ |
| 958 | OH | 2-Pyrimidyl | C₂H₅ |
| 959 | OH | 2-Pyrimidyl | n-C₃H₇ |
| 960 | OH | 2-Pyrimidyl | i-C₃H₇ |
| 961 | OH | 4-Pyrimidyl | H |
| 962 | OH | 4-Pyrimidyl | CH₃ |

TABLE A-continued

| No. | R³ | R⁴ | R⁵ |
|---|---|---|---|
| 963 | OH | 4-Pyrimidyl | $C_2H_5$ |
| 964 | OH | 4-Pyrimidyl | $n-C_3H_7$ |
| 965 | OH | 4-Pyrimidyl | $i-C_3H_7$ |
| 966 | OH | 5-Pyrimidyl | H |
| 967 | OH | 5-Pyrimidyl | $CH_3$ |
| 968 | OH | 5-Pyrimidyl | $C_2H_5$ |
| 969 | OH | 5-Pyrimidyl | $n-C_3H_7$ |
| 970 | OH | 5-Pyrimidyl | $i-C_3H_7$ |
| 971 | OH | 1,3,5-Triazinyl | H |
| 972 | OH | 1,3,5-Triazinyl | $CH_3$ |
| 973 | OH | 1,3,5-Triazinyl | $C_2H_5$ |
| 974 | OH | 1,3,5-Triazinyl | $n-C_3H_7$ |
| 975 | OH | 1,3,5-Triazinyl | $i-C_3H_7$ |
| 976 | OH | 2-Furyl | H |
| 977 | OH | 2-Furyl | $CH_3$ |
| 978 | OH | 2-Furyl | $C_2H_5$ |
| 979 | OH | 2-Furyl | $n-C_3H_7$ |
| 980 | OH | 2-Furyl | $i-C_3H_7$ |
| 981 | OH | 3-Furyl | H |
| 982 | OH | 3-Furyl | $CH_3$ |
| 983 | OH | 3-Furyl | $C_2H_5$ |
| 984 | OH | 3-Furyl | $n-C_3H_7$ |
| 985 | OH | 3-Furyl | $i-C_3H_7$ |
| 986 | OH | 2-Thienyl | H |
| 987 | OH | 2-Thienyl | $CH_3$ |
| 988 | OH | 2-Thienyl | $C_2H_5$ |
| 989 | OH | 2-Thienyl | $n-C_3H_7$ |
| 990 | OH | 2-Thienyl | $i-C_3H_7$ |
| 991 | OH | 3-Thienyl | H |
| 992 | OH | 3-Thienyl | $CH_3$ |
| 993 | OH | 3-Thienyl | $C_2H_5$ |
| 994 | OH | 3-Thienyl | $n-C_3H_7$ |
| 995 | OH | 3-Thienyl | $i-C_3H_7$ |
| 996 | OH | 2-Oxazolyl | H |
| 997 | OH | 2-Oxazolyl | $CH_3$ |
| 998 | OH | 2-Oxazolyl | $C_2H_5$ |
| 999 | OH | 2-Oxazolyl | $n-C_3H_7$ |
| 1000 | OH | 2-Oxazolyl | $i-C_3H_7$ |
| 1001 | OH | 4-Oxazolyl | H |
| 1002 | OH | 4-Oxazolyl | $CH_3$ |
| 1003 | OH | 4-Oxazolyl | $C_2H_5$ |
| 1004 | OH | 4-Oxazolyl | $n-C_3H_7$ |
| 1005 | OH | 2-Thiazolyl | $i-C_3H_7$ |
| 1006 | OH | 2-Thiazolyl | H |
| 1007 | OH | 2-Thiazolyl | $CH_3$ |
| 1008 | OH | 2-Thiazolyl | $C_2H_5$ |
| 1009 | OH | 2-Thiazolyl | $n-C_3H_7$ |
| 1010 | OH | 2-Thiazolyl | $i-C_3H_7$ |
| 1011 | OH | 4-Thiazolyl | H |
| 1012 | OH | 4-Thiazolyl | $CH_3$ |
| 1013 | OH | 4-Thiazolyl | $C-H_5$ |
| 1014 | OH | 4-Isoxazolyl | $n-C_3H_7$ |
| 1015 | OH | 4-Isoxazolyl | $i-C_3H_7$ |
| 1016 | OH | 3-Isoxazolyl | H |
| 1017 | OH | 3-Isoxazolyl | $CH_3$ |
| 1018 | OH | 3-Isoxazolyl | $C_2H_5$ |
| 1019 | OH | 3-Isoxazolyl | $n-C_3H_7$ |
| 1020 | OH | 3-Isoxazolyl | $i-C_3H_7$ |
| 1021 | OH | 5-Isoxazolyl | H |
| 1022 | OH | 5-Isoxazolyl | $CH_3$ |
| 1023 | OH | 5-Isoxazolyl | $C_2H_5$ |
| 1024 | OH | 5-Isoxazolyl | $n-C_3H_7$ |
| 1025 | OH | 5-Isoxazolyl | $i-C_3H_7$ |
| 1026 | OH | 2-Imidazolyl | H |
| 1027 | OH | 2-Imidazolyl | $CH_3$ |
| 1028 | OH | 2-Imidazolyl | $C_2H_5$ |
| 1029 | OH | 2-Imidazolyl | $n-C_3H_7$ |
| 1030 | OH | 2-Imidazolyl | $i-C_3H_7$ |
| 1031 | OH | 3-Pyrazolyl | H |
| 1032 | OH | 3-Pyrazolyl | $CH_3$ |
| 1033 | OH | 3-Pyrazolyl | $C_2H_5$ |
| 1034 | OH | 3-Pyrazolyl | $n-C_3H_7$ |
| 1035 | OH | 3-Pyrazolyl | $i-C_3H_7$ |
| 1036 | OH | 4-Pyrazolyl | H |
| 1037 | OH | 4-Pyrazolyl | $CH_3$ |
| 1038 | OH | 4-Pyrazolyl | $C_2H_5$ |
| 1039 | OH | 4-Pyrazolyl | $n-C_3H_7$ |

TABLE A-continued

| No. | R³ | R⁴ | R⁵ |
|---|---|---|---|
| 1040 | OH | 4-Pyrazolyl | i-C₃H₇ |
| 1041 | H | H | H |
| 1042 | H | H | CH₃ |
| 1043 | H | H | C₂H₅ |
| 1044 | H | H | n-C₃H₇ |
| 1045 | H | H | i-C₃H₇ |
| 1046 | H | OH | H |
| 1047 | H | OH | CH₃ |
| 1048 | H | OH | C₂H₅ |
| 1049 | H | OH | n-C₃H₇ |
| 1050 | H | OH | i-C₃H₇ |
| 1051 | H | Cl | n-C₄H₉ |
| 1052 | H | Cl | CH₃ |
| 1053 | H | Cl | C₂H₅ |
| 1054 | H | Cl | n-C₃H₇ |
| 1055 | H | Cl | i-C₃H₇ |
| 1056 | H | OCH₃ | H |
| 1057 | H | OCH₃ | CH₃ |
| 1058 | H | OCH₃ | C₂H₅ |
| 1059 | H | OCH₃ | n-C₃H₇ |
| 1060 | H | OCH₃ | i-C₃H₇ |
| 1061 | H | CH₃ | H |
| 1062 | H | CH₃ | CH₃ |
| 1063 | H | CH₃ | C₂H₅ |
| 1064 | H | CH₃ | n-C₃H₇ |
| 1065 | H | CH₃ | i-C₃H₇ |
| 1066 | H | Cyclopropyl | H |
| 1067 | H | Cyclopropyl | CH₃ |
| 1068 | H | Cyclopropyl | C₂H₅ |
| 1069 | H | Cyclopropyl | n-C₃H₇ |
| 1070 | H | Cyclopropyl | i-C₃H₇ |
| 1071 | Cl | H | H |
| 1072 | Cl | H | CH₃ |
| 1073 | Cl | H | C₂H₅ |
| 1074 | Cl | H | n-C₃H₇ |
| 1075 | Cl | H | i-C₃H₇ |
| 1076 | Cl | OH | H |
| 1077 | Cl | OH | CH₃ |
| 1078 | Cl | OH | C₂H₅ |
| 1079 | Cl | OH | n-C₃H₇ |
| 1080 | Cl | OH | i-C₃H₇ |
| 1081 | Cl | Cl | n-C₄H₉ |
| 1082 | Cl | Cl | CH₃ |
| 1083 | Cl | Cl | C₂H₅ |
| 1084 | Cl | Cl | n-C₃H₇ |
| 1085 | Cl | Cl | i-C₃H₇ |
| 1086 | Cl | OCH₃ | H |
| 1087 | Cl | OCH₃ | CH₃ |
| 1088 | Cl | OCH₃ | C₂H₅ |
| 1089 | Cl | OCH₃ | n-C₃H₇ |
| 1090 | Cl | OCH₃ | i-C₃H₇ |
| 1091 | Cl | CH₃ | H |
| 1092 | Cl | CH₃ | CH₃ |
| 1093 | Cl | CH₃ | C₂H₅ |
| 1094 | Cl | CH₃ | n-C₃H₇ |
| 1095 | Cl | CH₃ | i-C₃H₇ |
| 1096 | Cl | Cyclopropyl | H |
| 1097 | Cl | Cyclopropyl | CH₃ |
| 1098 | Cl | Cyclopropyl | C₂H₅ |
| 1099 | Cl | Cyclopropyl | n-C₃H₇ |
| 1100 | Cl | Cyclopropyl | i-C₃H₇ |
| 1101 | SCH₃ | H | H |
| 1102 | SCH₃ | H | CH₃ |
| 1103 | SCH₃ | H | C₂H₅ |
| 1104 | SCH₃ | H | n-C₃H₇ |
| 1105 | SCH₃ | H | i-C₃H₇ |
| 1106 | SCH₃ | OH | H |
| 1107 | SCH₃ | OH | CH₃ |
| 1108 | SCH₃ | OH | C₂H₅ |
| 1109 | SCH₃ | OH | n-C₃H₇ |
| 1110 | SCH₃ | OH | i-C₃H₇ |
| 1111 | SCH₃ | CH₃ | H |
| 1112 | SCH₃ | CH₃ | CH₃ |
| 1113 | SCH₃ | CH₃ | C₂H₅ |
| 1114 | SCH₃ | CH₃ | n-C₃H₇ |
| 1115 | SCH₃ | CH₃ | i-C₃H₇ |
| 1116 | SCH₃ | SCH₃ | H |

TABLE A-continued

| No. | R³ | R⁴ | R⁵ |
|-----|----|----|----|
| 1117 | SCH₃ | SCH₃ | CH₃ |
| 1118 | SCH₃ | SCH₃ | C-H₅ |
| 1119 | SCH₃ | SCH₃ | n-C₃H₇ |
| 1120 | SCH₃ | SCH₃ | i-C₃H₇ |
| 1121 | SCH₃ | Cyclopropyl | H |
| 1122 | SCH₃ | Cyclopropyl | CH₃ |
| 1123 | SCH₃ | Cyclopropyl | C₂H₅ |
| 1124 | SCH₃ | Cyclopropyl | n-C₃H₇ |
| 1125 | SCH₃ | Cyclopropyl | i-C₃H₇ |
| 1126 | Cyclopropyl | H | H |
| 1127 | Cycloprbpyl | H | CH₃ |
| 1128 | Cyclopropyl | H | C₂H₅ |
| 1129 | Cyclopropyl | H | n-C₃H₇ |
| 1130 | Cyclopropyl | H | i-C₃H₇ |
| 1131 | Cyclopropyl | OH | H |
| 1132 | Cyclopropyl | OH | CH₃ |
| 1133 | Cyclopropyl | OH | C₂H₅ |
| 1134 | Cyclopropyl | OH | n-C₃H₇ |
| 1135 | Cyclopropyl | OH | i-C₃H₇ |
| 1136 | Cyclopropyl | Cl | n-C₄H₉ |
| 1137 | Cyclopropyl | Cl | CH₃ |
| 1138 | Cyclopropyl | Cl | C₂H₅ |
| 1139 | Cyclopropyl | Cl | n-C₃H₇ |
| 1140 | Cyclopropyl | Cl | i-C₃H₇ |
| 1141 | Cyclopropyl | OCH₃ | H |
| 1142 | Cyclopropyl | OCH₃ | CH₃ |
| 1143 | Cyclopropyl | OCH₃ | C₂H₅ |
| 1144 | Cyclopropyl | OCH₃ | n-C₃H₇ |
| 1145 | Cyclopropyl | OCH₃ | i-C₃H₇ |
| 1146 | Cyclopropyl | SCH₃ | H |
| 1147 | Cyclopropyl | SCH₃ | CH₃ |
| 1148 | Cyclopropyl | SCH₃ | C₂H₅ |
| 1149 | Cyclopropyl | SCH₃ | n-C₃H₇ |
| 1150 | Cyclopropyl | SCH₃ | i-C₃H₇ |
| 1151 | Cyclopropyl | CH₃ | H |
| 1152 | Cyclopropyl | CH₃ | CH₃ |
| 1153 | Cyclopropyl | CH₃ | C₂H₅ |
| 1154 | Cyclopropyl | CH₃ | n-C₃H₇ |
| 1155 | Cyclopropyl | CH₃ | i-C₃H₇ |
| 1156 | CH₃ | 2-F—C₆H₄ | H |
| 1157 | CH₃ | 2-F—C₆H₄ | CH₃ |
| 1158 | CH₃ | 2-F—C₆H₄ | C₂H₅ |
| 1159 | CH₃ | 2-F—C₆H₄ | n-C₃H₇ |
| 1160 | CH₃ | 2-F—C₆H₄ | i-C₃H₇ |
| 1161 | CH₃ | 2-F—C₆H₄ | n-C₄H₉ |
| 1162 | CH₃ | 2-F—C₆H₄ | t-C₄H₉ |
| 1163 | CH₃ | 2-F—C₆H₄ | n-C₆H₁₃ |
| 1164 | CH₃ | 2-F—C₆H₄ | Prop-1-en-3-yl |
| 1165 | CH₃ | 2-F—C₆H₄ | (E)-1-Chloroprop-1-en-3-yl |
| 1166 | CH₃ | 2-F—C₆H₄ | Propyn-3-yl |
| 1167 | CH₃ | 2-F—C₆H₄ | 3-Methylbut-2-en-1-yl |
| 1168 | CH₃ | 3-F—C₆H₄ | H |
| 1169 | CH₃ | 3-F—C₆H₄ | CH₃ |
| 1170 | CH₃ | 3-F—C₆H₄ | C₂H₅ |
| 1171 | CH₃ | 3-F—C₆H₄ | n-C₃H₇ |
| 1172 | CH₃ | 3-F—C₆H₄ | i-C₃H₇ |
| 1173 | CH₃ | 3-F—C₆H₄ | n-C₄H₉ |
| 1174 | CH₃ | 3-F—C₆H₄ | t-C₄H₉ |
| 1175 | CH₃ | 3-F—C₆H₄ | n-C₆H₁₃ |
| 1176 | CH₃ | 3-F—C₆H₄ | Prop-1-en-3-yl |
| 1177 | CH₃ | 3-F—C₆H₄ | (E)-1-Chloroprop-1-en-3-yl |
| 1178 | CH₃ | 3-F—C₆H₄ | Propyn-3-yl |
| 1179 | CH₃ | 3-F—C₆H₄ | 3-Methylbut-2-en-1-yl |
| 1180 | CH₃ | 4-F—C₆H₄ | H |
| 1181 | CH₃ | 4-F—C₆H₄ | CH₃ |
| 1182 | CH₃ | 4-F—C₆H₄ | C₂H₅ |
| 1183 | CH₃ | 4-F—C₆H₄ | n-C₃H₇ |
| 1184 | CH₃ | 4-F—C₆H₄ | i-C₃H₇ |
| 1185 | CH₃ | 4-F—C₆H₄ | n-C₄H₉ |
| 1186 | CH₃ | 4-F—C₆H₄ | t-C₄H₉ |
| 1187 | CH₃ | 4-F—C₆H₄ | n-C₆H₁₃ |
| 1188 | CH₃ | 4-F—C₆H₄ | Prop-1-en-3-yl |
| 1189 | CH₃ | 4-F—C₆H₄ | (E)-1-Chloroprop-1-en-3-yl |
| 1190 | CH₃ | 4-F—C₆H₄ | Propyn-3-yl |
| 1191 | CH₃ | 4-F—C₆H₄ | 3-Methylbut-2-en-1 |
| 1192 | CH₃ | 2-Cl—C₆H₄ | H |
| 1193 | CH₃ | 2-Cl—C₆H₄ | CH₃ |

TABLE A-continued

| No. | R³ | R⁴ | R⁵ |
|---|---|---|---|
| 1194 | $CH_3$ | 2-Cl—$C_6H_4$ | $C_2H_5$ |
| 1195 | $CH_3$ | 2-Cl—$C_6H_4$ | n-$C_3H_7$ |
| 1196 | $CH_3$ | 2-Cl—$C_6H_4$ | i-$C_3H_7$ |
| 1197 | $CH_3$ | 2-Cl—$C_6H_4$ | n-$C_4H_9$ |
| 1198 | $CH_3$ | 2-Cl—$C_6H_4$ | t-$C_4H_9$ |
| 1199 | $CH_3$ | 2-Cl—$C_6H_4$ | n-$C_6H_{13}$ |
| 1200 | $CH_3$ | 2-Cl—$C_6H_4$ | Prop-1-en-3-yl |
| 1201 | $CH_3$ | 2-Cl—$C_6H_4$ | (E)-1-Chloroprop-1-en-3-yl |
| 1202 | $CH_3$ | 2-Cl—$C_6H_4$ | Propyn-3-yl |
| 1203 | $CH_3$ | 2-Cl—$C_6H_4$ | 3-Methylbut-2-en-1-yl |
| 1204 | $CH_3$ | 3-Cl—$C_6H_4$ | H |
| 1205 | $CH_3$ | 3-Cl—$C_6H_4$ | $CH_3$ |
| 1206 | $CH_3$ | 3-Cl—$C_6H_4$ | $C_2H_5$ |
| 1207 | $CH_3$ | 3-Cl—$C_6H_4$ | n-$C_3H_7$ |
| 1208 | $CH_3$ | 3-Cl—$C_6H_4$ | i-$C_3H_7$ |
| 1209 | $CH_3$ | 3-Cl—$C_6H_4$ | n-$C_4H_9$ |
| 1210 | $CH_3$ | 3-Cl—$C_6H_4$ | t-$C_4H_9$ |
| 1211 | $CH_3$ | 3-Cl—$C_6H_4$ | n-$C_6H_{13}$ |
| 1212 | $CH_3$ | 3-Cl—$C_6H_4$ | Prop-1-en-3-yl |
| 1213 | $CH_3$ | 3-Cl—$C_6H_4$ | (E)-1-Chloroprop-1-en-3-yl |
| 1214 | $CH_3$ | 3-Cl—$C_6H_4$ | Propyn-3-yl |
| 1215 | $CH_3$ | 3-Cl—$C_6H_4$ | 3-Methylbut-2-en-1-yl |
| 1216 | $CH_3$ | 4-Cl—$C_6H_4$ | H |
| 1217 | $CH_3$ | 4-Cl—$C_6H_4$ | $CH_3$ |
| 1218 | $CH_3$ | 4-Cl—$C_6H_4$ | $C_2H_5$ |
| 1219 | $CH_3$ | 4-Cl—$C_6H_4$ | n-$C_3H_7$ |
| 1220 | $CH_3$ | 4-Cl—$C_6H_4$ | i-$C_3H_7$ |
| 1221 | $CH_3$ | 4-Cl—$C_6H_4$ | n-$C_4H_9$ |
| 1222 | $CH_3$ | 4-Cl—$C_6H_4$ | t-$C_4H_9$ |
| 1223 | $CH_3$ | 4-Cl—$C_6H_4$ | n-$C_6H_{13}$ |
| 1224 | $CH_3$ | 4-Cl—$C_6H_4$ | Prop-1-en-3-yl |
| 1225 | $CH_3$ | 4-Cl—$C_6H_4$ | (E)-1-Chloroprop-1-en-3-yl |
| 1226 | $CH_3$ | 4-Cl—$C_6H_4$ | Propyn-3-yl |
| 1227 | $CH_3$ | 4-Cl—$C_6H_4$ | 3-Methylbut-2-en-1-yl |
| 1228 | $CH_3$ | 2,3-$Cl_2$—$C_6H_3$ | H |
| 1229 | $CH_3$ | 2,3-$Cl_2$—$C_6H_3$ | $CH_3$ |
| 1230 | $CH_3$ | 2,3-$Cl_2$—$C_6H_3$ | $C_2H_5$ |
| 1231 | $CH_3$ | 2,3-$Cl_2$—$C_6H_3$ | n-$C_3H_7$ |
| 1232 | $CH_3$ | 2,3-$Cl_2$—$C_6H_3$ | i-$C_3H_7$ |
| 1233 | $CH_3$ | 2,3-$Cl_2$—$C_6H_3$ | n-$C_4H_9$ |
| 1234 | $CH_3$ | 2,3-$Cl_2$—$C_6H_3$ | t-$C_4H_9$ |
| 1235 | $CH_3$ | 2,3-$Cl_2$—$C_6H_3$ | n-$C_6H_{13}$ |
| 1236 | $CH_3$ | 2,3-$Cl_2$—$C_6H_3$ | Prop-1-en-3-yl |
| 1237 | $CH_3$ | 2,3-$Cl_2$—$C_6H_3$ | (E)-1-Chloroprop-1-en-3-yl |
| 1238 | $CH_3$ | 2,3-$Cl_2$—$C_6H_3$ | Propyn-3-yl |
| 1239 | $CH_3$ | 2,3-$Cl_2$—$C_6H_3$ | 3-Methylbut-2-en-1-yl |
| 1240 | $CH_3$ | 2,4-$Cl_2$—$C_6H_3$ | H |
| 1241 | $CH_3$ | 2,4-$Cl_2$—$C_6H_3$ | $CH_3$ |
| 1242 | $CH_3$ | 2,4-$Cl_2$—$C_6H_3$ | $C_2H_5$ |
| 1243 | $CH_3$ | 2,4-$Cl_2$—$C_6H_3$ | n-$C_3H_7$ |
| 1244 | $CH_3$ | 2,4-$Cl_2$—$C_6H_3$ | i-$C_3H_7$ |
| 1245 | $CH_3$ | 2,4-$Cl_2$—$C_6H_3$ | n-$C_4H_9$ |
| 1246 | $CH_3$ | 2,4-$Cl_2$—$C_6H_3$ | t-$C_4H_9$ |
| 1247 | $CH_3$ | 2,4-$Cl_2$—$C_6H_3$ | n-$C_6H_{13}$ |
| 1248 | $CH_3$ | 2,4-$Cl_2$—$C_6H_3$ | Prop-1-en-3-yl |
| 1249 | $CH_3$ | 2,4-$Cl_2$—$C_6H_3$ | (E)-1-Chloroprop-1-en-3-yl |
| 1250 | $CH_3$ | 2,4-$Cl_2$—$C_6H_3$ | Propyn-3-yl |
| 1251 | $CH_3$ | 2,4-$Cl_2$—$C_6H_3$ | 3-Methylbut-2-en-1-yl |
| 1252 | $CH_3$ | 2,5-$Cl_2$—$C_6H_3$ | H |
| 1253 | $CH_3$ | 2,5-$Cl_2$—$C_6H_3$ | $CH_3$ |
| 1254 | $CH_3$ | 2,5-$Cl_2$—$C_6H_3$ | $C_2H_5$ |
| 1255 | $CH_3$ | 2,5-$Cl_2$—$C_6H_3$ | n-$C_3H_7$ |
| 1256 | $CH_3$ | 2,5-$Cl_2$—$C_6H_3$ | i-$C_3H_7$ |
| 1257 | $CH_3$ | 2,5-$Cl_2$—$C_6H_3$ | n-$C_4H_9$ |
| 1258 | $CH_3$ | 2,5-$Cl_2$—$C_6H_3$ | t-$C_4H_9$ |
| 1259 | $CH_3$ | 2,5-$Cl_2$—$C_6H_3$ | n-$C_6H_{13}$ |
| 1260 | $CH_3$ | 2,5-$Cl_2$—$C_6H_3$ | Prop-1-en-3-yl |
| 1261 | $CH_3$ | 2,5-$Cl_2$—$C_6H_3$ | (E)-1-Chloroprop-1-en-3-yl |
| 1262 | $CH_3$ | 2,5-$Cl_2$—$C_6H_3$ | Propyn-3-yl |
| 1263 | $CH_3$ | 2,5-$Cl_2$—$C_6H_3$ | 3-Methylbut-2-en-1-yl |
| 1264 | $CH_3$ | 2,6-$Cl_2$—$C_6H_3$ | H |
| 1265 | $CH_3$ | 2,6-$Cl_2$—$C_6H_3$ | $CH_3$ |
| 1266 | $CH_3$ | 2,6-$Cl_2$—$C_6H_3$ | $C_2H_5$ |
| 1267 | $CH_3$ | 2,6-$Cl_2$—$C_6H_3$ | n-$C_3H_7$ |
| 1268 | $CH_3$ | 2,6-$Cl_2$—$C_6H_3$ | i-$C_3H_7$ |
| 1269 | $CH_3$ | 2,6-$Cl_2$—$C_6H_3$ | n-$C_4H_9$ |
| 1270 | $CH_3$ | 2,6-$Cl_2$—$C_6H_3$ | t-$C_4H_9$ |

TABLE A-continued

| No. | R³ | R⁴ | R⁵ |
|---|---|---|---|
| 1271 | CH₃ | 2,6-Cl₂—C₆H₃ | n-C₆H₁₃ |
| 1272 | CH₃ | 2,6-Cl₂—C₆H₃ | Prop-1-en-3-yl |
| 1273 | CH₃ | 2,6-Cl₂—C₆H₃ | (E)-1-Chloroprop-1-en-3-yl |
| 1274 | CH₃ | 2,6-Cl₂—C₆H₃ | Propyn-3-yl |
| 1275 | CH₃ | 2,6-Cl₂—C₆H₃ | 3-Methylbut-2-en-1-yl |
| 1276 | CH₃ | 3,4-Cl₂—C₆H₃ | H |
| 1277 | CH₃ | 3,4-Cl₂—C₆H₃ | CH₃ |
| 1278 | CH₃ | 3,4-Cl₂—C₆H₃ | C₂H₅ |
| 1279 | CH₃ | 3,4-Cl₂—C₆H₃ | n-C₃H₇ |
| 1280 | CH₃ | 3,4-Cl₂—C₆H₃ | i-C₃H₇ |
| 1281 | CH₃ | 3,4-Cl₂—C₆H₃ | n-C₄H₉ |
| 1282 | CH₃ | 3,4-Cl₂—C₆H₃ | t-C₄H₉ |
| 1283 | CH₃ | 3,4-Cl₂—C₆H₃ | n-C₆H-3 |
| 1284 | CH₃ | 3,4-Cl₂—C₆H₃ | Prop-1-en-3-yl |
| 1285 | CH₃ | 3,4-Cl₂—C₆H₃ | (E)-1-Chloroprop-1-en-3-yl |
| 1286 | CH₃ | 3,4-Cl₂—C₆H₃ | Propyn-3-yl |
| 1287 | CH₃ | 3,4-Cl₂—C₆H₃ | 3-Methylbut-2-en-1-yl |
| 1288 | CH₃ | 3,5-Cl₂—C₆H₃ | H |
| 1289 | CH₃ | 3,5-Cl₂—C₆H₃ | CH₃ |
| 1290 | CH₃ | 3,5-Cl₂—C₆H₃ | C₂H₅ |
| 1291 | CH₃ | 3,5-Cl₂—C₆H₃ | n-C₃H₇ |
| 1292 | CH₃ | 3,5-Cl₂—C₆H₃ | i-C₃H₇ |
| 1293 | CH₃ | 3,5-Cl₂—C₆H₃ | n-C₄H₉ |
| 1294 | CH₃ | 3,5-Cl₂—C₆H₃ | t-C₄H₉ |
| 1295 | CH₃ | 3,5-Cl₂—C₆H₃ | n-C₆H₁₃ |
| 1296 | CH₃ | 3,5-Cl₂—C₆H₃ | Prop-1-en-3-yl |
| 1297 | CH₃ | 3,5-Cl₂—C₆H₃ | (E)-1-Chloroprop-1-en-3-yl |
| 1298 | CH₃ | 3,5-Cl₂—C₆H₃ | Propyn-3-yl |
| 1299 | CH₃ | 3,5-Cl₂—C₆H₃ | 3-Methylbut-2-en-1-yl |
| 1300 | CH₃ | 2-Br—C₆H₄ | H |
| 1301 | CH₃ | 2-Br—C₆H₄ | CH₃ |
| 1302 | CH₃ | 2-Br—C₆H₄ | C₂H₅ |
| 1303 | CH₃ | 2-Br—C₆H₄ | n-C₃H₇ |
| 1304 | CH₃ | 2-Br—C₆H₄ | i-C₃H₇ |
| 1305 | CH₃ | 2-Br—C₆H₄ | n-C₄H₉ |
| 1306 | CH₃ | 2-Br—C₆H₄ | t-C₄H₉ |
| 1307 | CH₃ | 2-Br—C₆H₄ | n-C₆H₁₃ |
| 1308 | CH₃ | 2-Br—C₆H₄ | Prop-1-en-3-yl |
| 1309 | CH₃ | 2-Br—C₆H₄ | (E)-1-Chloroprop-1-en-3-yl |
| 1310 | CH₃ | 2-Br—C₆H₄ | Propyn-3-yl |
| 1311 | CH₃ | 2-Br—C₆H₄ | 3-Methylbut-2-en-1-yl |
| 1312 | CH₃ | 3-Br—C₆H₄ | H |
| 1313 | CH₃ | 3-Br—C₆H₄ | CH₃ |
| 1314 | CH₃ | 3-Br—C₆H₄ | C₂H₅ |
| 1315 | CH₃ | 3-Br—C₆H₄ | n-C₃H₇ |
| 1316 | CH₃ | 3-Br—C₆H₄ | i-C₃H₇ |
| 1317 | CH₃ | 3-Br—C₆H₄ | n-C₄H₉ |
| 1318 | CH₃ | 3-Br—C₆H₄ | t-C₄H₉ |
| 1319 | CH₃ | 3-Br—C₆H₄ | n-C₆H₁₃ |
| 1320 | CH₃ | 3-Br—C₆H₄ | Prop-1-en-3-yl |
| 1321 | CH₃ | 3-Br—C₆H₄ | (E)-1-Chloroprop-1-en-3-yl |
| 1322 | CH₃ | 3-Br—C₆H₄ | Propyn-3-yl |
| 1323 | CH₃ | 3-Br—C₆H₄ | 3-Methylbut-2-en-1-yl |
| 1324 | CH₃ | 4-Br—C₆H₄ | H |
| 1325 | CH₃ | 4-Br—C₆H₄ | CH₃ |
| 1326 | CH₃ | 4-Br—C₆H₄ | C₂H₅ |
| 1327 | CH₃ | 4-Br—C₆H₄ | n-C₃H₇ |
| 1328 | CH₃ | 4-Br—C₆H₄ | i-C₃H₇ |
| 1329 | CH₃ | 4-Br—C₆H₄ | n-C₄H₉ |
| 1330 | CH₃ | 4-Br—C₆H₄ | t-C₄H₉ |
| 1331 | CH₃ | 4-Br—C₆H₄ | n-C₆H₁₃ |
| 1332 | CH₃ | 4-Br—C₆H₄ | Prop-1-en-3-yl |
| 1333 | CH₃ | 4-Br—C₆H₄ | (E)-1-Chloroprop-1-en-3-yl |
| 1334 | CH₃ | 4-Br—C₆H₄ | Propyn-3-yl |
| 1335 | CH₃ | 4-Br—C₆H₄ | 3-Methylbut-2-en-1-yl |
| 1336 | CH₃ | 2-I—C₆H₄ | H |
| 1337 | CH₃ | 2-I—C₆H₄ | CH₃ |
| 1338 | CH₃ | 2-I—C₆H₄ | C₂H₅ |
| 1339 | CH₃ | 2-I—C₆H₄ | n-C₃H₇ |
| 1340 | CH₃ | 2-I—C₆H₄ | i-C₃H₇ |
| 1341 | CH₃ | 2-I—C₆H₄ | n-C₄H₉ |
| 1342 | CH₃ | 2-I—C₆H₄ | t-C₄H₉ |
| 1343 | CH₃ | 2-I—C₆H₄ | n-C₆H₁₃ |
| 1344 | CH₃ | 2-I—C₆H₄ | Prop-1-en-3-yl |
| 1345 | CH₃ | 2-I—C₆H₄ | (E)-1-Chloroprop-1-en-3-yl |
| 1346 | CH₃ | 2-I—C₆H₄ | Propyn-3-yl |
| 1347 | CH₃ | 2-I—C₆H₄ | 3-Methylbut-2-en-1-yl |

TABLE A-continued

| No. | R³ | R⁴ | R⁵ |
|---|---|---|---|
| 1348 | CH₃ | 3-I—C₆H₄ | H |
| 1349 | CH₃ | 3-I—C₆H₄ | CH₃ |
| 1350 | CH₃ | 3-I—C₆H₄ | C₂H₅ |
| 1351 | CH₃ | 3-I—C₆H₄ | n-C₃H₇ |
| 1352 | CH₃ | 3-I—C₆H₄ | i-C₃H₇ |
| 1353 | CH₃ | 3-I—C₆H₄ | n-C₄H₉ |
| 1354 | CH₃ | 3-I—C₆H₄ | t-C₄H₉ |
| 1355 | CH₃ | 3-I—C₆H₄ | n-C₆H₁₃ |
| 1356 | CH₃ | 3-I—C₆H₄ | Prop-1-en-3-yl |
| 1357 | CH₃ | 3-I—C₆H₄ | (E)-1-Chloroprop-1-en-3-yl |
| 1358 | CH₃ | 3-I—C₆H₄ | Propyn-3-yl |
| 1359 | CH₃ | 3-I—C₆H₄ | 3-Methylbut-2-en-1-yl |
| 1360 | CH₃ | 4-I—C₆H₄ | H |
| 1361 | CH₃ | 4-I—C₆H₄ | CH₃ |
| 1362 | CH₃ | 4-I—C₆H₄ | C₂H₅ |
| 1363 | CH₃ | 4-I—C₆H₄ | n-C₃H₇ |
| 1364 | CH₃ | 4-I—C₆H₄ | i-C₃H₇ |
| 1365 | CH₃ | 4-I—C₆H₄ | n-C₄H₉ |
| 1366 | CH₃ | 4-I—C₆H₄ | t-C₄H₉ |
| 1367 | CH₃ | 4-I—C₆H₄ | n-C₆H₁₃ |
| 1368 | CH₃ | 4-I—C₆H₄ | Prop-1-en-3-yl |
| 1369 | CH₃ | 4-I—C₆H₄ | (E)-1-Chloroprop-1-en-3-yl |
| 1370 | CH₃ | 4-I—C₆H₄ | Propyn-3-yl |
| 1371 | CH₃ | 4-I—C₆H₄ | 3-Methylbut-2-en-1-yl |
| 1372 | CH₃ | 2-CN—C₆H₄ | H |
| 1373 | CH₃ | 2-CN—C₆H₄ | CH₃ |
| 1374 | CH₃ | 2-CN—C₆H₄ | C₂H₅ |
| 1375 | CH₃ | 2-CN—C₆H₄ | n-C₃H₇ |
| 1376 | CH₃ | 2-CN—C₆H₄ | i-C₃H₇ |
| 1377 | CH₃ | 2-CN—C₆H₄ | n-C₄H₉ |
| 1378 | CH₃ | 2-CN—C₆H₄ | t-C₄H₉ |
| 1379 | CH₃ | 2-CN—C₆H₄ | n-C₆H₁₃ |
| 1380 | CH₃ | 2-CN—C₆H₄ | Prop-1-en-3-yl |
| 1381 | CH₃ | 2-CN—C₆H₄ | (E)-1-Chloroprop-1-en-3-yl |
| 1382 | CH₃ | 2-CN—C₆H₄ | Propyn-3-yl |
| 1383 | CH₃ | 2-CN—C₆H₄ | 3-Methylbut-2-en-i-yl |
| 1384 | CH₃ | 3-CN—C₆H₄ | H |
| 1385 | CH₃ | 3-CN—C₆H₄ | CH₃ |
| 1386 | CH₃ | 3-CN—C₆H₄ | C₂H₅ |
| 1387 | CH₃ | 3-CN—C₆H₄ | n-C₃H₇ |
| 1388 | CH₃ | 3-CN—C₆H₄ | i-C₃H₇ |
| 1389 | CH₃ | 3-CN—C₆H₄ | n-C₄H₉ |
| 1390 | CH₃ | 3-CN—C₆H₄ | t-C₄H₉ |
| 1391 | CH₃ | 3-CN—C₆H₄ | n-C₆H₁₃ |
| 1392 | CH₃ | 3-CN—C₆H₄ | Prop-1-en-3-yl |
| 1393 | CH₃ | 3-CN—C₆H₄ | (E)-1-Chloroprop-1-en-3-yl |
| 1394 | CH₃ | 3-CN—C₆H₄ | Propyn-3-yl |
| 1395 | CH₃ | 3-CN—C₆H₄ | 3-Methylbut-2-en-1-yl |
| 1396 | CH₃ | 4-CN—C₆H₄ | H |
| 1397 | CH₃ | 4-CN—C₆H₄ | CH₃ |
| 1398 | CH₃ | 4-CN—C₆H₄ | C₂H₅ |
| 1399 | CH₃ | 4-CN—C₆H₄ | n-C₃H₇ |
| 1400 | CH₃ | 4-CN—C₆H₄ | i-C₃H₇ |
| 1401 | CH₃ | 4-CN—C₆H₄ | n-C₄H₉ |
| 1402 | CH₃ | 4-CN—C₆H₄ | t-C₄H₉ |
| 1403 | CH₃ | 4-CN—C₆H₄ | n-C₆H₁₃ |
| 1404 | CH₃ | 4-CN—C₆H₄ | Prop-1-en-3-yl |
| 1405 | CH₃ | 4-CN—C₆H₄ | (E)-1-Chloroprop-1-en-3-yl |
| 1406 | CH₃ | 4-CN—C₆H₄ | Propyn-3-yl |
| 1407 | CH₃ | 4-CN—C₆H₄ | 3-Methylbut-2-en-1-yl |
| 1408 | CH₃ | 2-NO₂—C₆H₄ | H |
| 1409 | CH₃ | 2-NO₂—C₆H₄ | CH₃ |
| 1410 | CH₃ | 2-NO₂—C₆H₄ | C₂H₅ |
| 1411 | CH₃ | 2-NO₂—C₆H₄ | n-C₃H₇ |
| 1412 | CH₃ | 2-NO₂—C₆H₄ | i-C₃H₇ |
| 1413 | CH₃ | 2-NO₂—C₆H₄ | n-C₄H₉ |
| 1414 | CH₃ | 2-NO₂—C₆H₄ | t-C₄H₉ |
| 1415 | CH₃ | 2-NO₂—C₆H₄ | n-C₆H₁₃ |
| 1416 | CH₃ | 2-NO₂—C₆H₄ | Prop-1-en-3-yl |
| 1417 | CH₃ | 2-NO₂—C₆H₄ | (E)-1-Chloroprop-1-en-3-yl |
| 1418 | CH₃ | 2-NO₂—C₆H₄ | Propyn-3-yl |
| 1419 | CH₃ | 2-NO₂—C₆H₄ | 3-Methylbut-2-en-1-yl |
| 1420 | CH₃ | 3-NO₂—C₆H₄ | H |
| 1421 | CH₃ | 3-NO₂—C₆H₄ | CH₃ |
| 1422 | CH₃ | 3-NO₂—C₆H₄ | C₂H₅ |
| 1423 | CH₃ | 3-NO₂—C₆H₄ | n-C₃H₇ |
| 1424 | CH₃ | 3-NO₂—C₆H₄ | i-C₃H₇ |

TABLE A-continued

| No. | R³ | R⁴ | R⁵ |
|---|---|---|---|
| 1425 | CH₃ | 3-NO₂—C₆H₄ | n-C₄H₉ |
| 1426 | CH₃ | 3-NO₂—C₆H₄ | t-C₄H₉ |
| 1427 | CH₃ | 3-NO₂—C₆H₄ | n-C₆H₁₃ |
| 1428 | CH₃ | 3-NO₂—C₆H₄ | Prop-1-en-3-yl |
| 1429 | CH₃ | 3-NO₂—C₆H₄ | (E)-1-Chloroprop-1-en-3-yl |
| 1430 | CH₃ | 3-NO₂—C₆H₄ | Propyn-3-yl |
| 1431 | CH₃ | 3-NO₂—C₆H₄ | 3-Methylbut-2-en-1-yl |
| 1432 | CH₃ | 4-NO₂—C₆H₄ | H |
| 1433 | CH₃ | 4-NO₂—C₆H₄ | CH₃ |
| 1434 | CH₃ | 4-NO₂—C₆H₄ | C₂H₅ |
| 1435 | CH₃ | 4-NO₂—C₆H₄ | n-C₃H₇ |
| 1436 | CH₃ | 4-NO₂—C₆H₄ | i-C₃H₇ |
| 1437 | CH₃ | 4-NO₂—C₆H₄ | n-C₄H₉ |
| 1438 | CH₃ | 4-NO₂—C₆H₄ | t-C₄H₉ |
| 1439 | CH₃ | 4-NO₂—C₆H₄ | n-C₆H₁₃ |
| 1440 | CH₃ | 4-NO₂—C₆H₄ | Prop-1-en-3-yl |
| 1441 | CH₃ | 4-NO₂—C₆H₄ | (E)-1-Chloroprop-1-en-3-yl |
| 1442 | CH₃ | 4-NO₂—C₆H₄ | Propyn-3-yl |
| 1443 | CH₃ | 4-NO₂—C₆H₄ | 3-Methylbut-2-en-1-yl |
| 1444 | CH₃ | 2-CH₃—C₆H₄ | H |
| 1445 | CH₃ | 2-CH₃—C₆H₄ | CH₃ |
| 1446 | CH₃ | 2-CH₃—C₆H₄ | C₂H₅ |
| 1447 | CH₃ | 2-CH₃—C₆H₄ | n-C₃H₇ |
| 1448 | CH₃ | 2-CH₃—C₆H₄ | i-C₃H₇ |
| 1449 | CH₃ | 2-CH₃—C₆H₄ | n-C₄H₉ |
| 1450 | CH₃ | 2-CH₃—C₆H₄ | t-C₄H₉ |
| 1451 | CH₃ | 2-CH₃—C₆H₄ | n-C₆H₁₃ |
| 1452 | CH₃ | 2-CH₃—C₆H₄ | Prop-1-en-3-yl |
| 1453 | CH₃ | 2-CH₃—C₆H₄ | (E)-1-Chloroprop-1-en-3-yl |
| 1454 | CH₃ | 2-CH₃—C₆H₄ | Propyn-3-yl |
| 1455 | CH₃ | 2-CH₃—C₆H₄ | 3-Methylbut-2-en-1-yl |
| 1456 | CH₃ | 3-CH₃—C₆H₄ | H |
| 1457 | CH₃ | 3-CH₃—C₆H₄ | CH₃ |
| 1458 | CH₃ | 3-CH₃—C₆H₄ | C₂H₅ |
| 1459 | CH₃ | 3-CH₃—C₆H₄ | n-C₃H₇ |
| 1460 | CH₃ | 3-CH₃—C₆H₄ | i-C₃H₇ |
| 1461 | CH₃ | 3-CH₃—C₆H₄ | n-C₄H₉ |
| 1462 | CH₃ | 3-CH₃—C₆H₄ | t-C₄H₉ |
| 1463 | CH₃ | 3-CH₃—C₆H₄ | n-C₆H₁₃ |
| 1464 | CH₃ | 3-CH₃—C₆H₄ | Prop-1-en-3-yl |
| 1465 | CH₃ | 3-CH₃—C₆H₄ | (E)-1-Chloroprop-1-en-3-yl |
| 1466 | CH₃ | 3-CH₃—C₆H₄ | Propyn-3-yl |
| 1467 | CH₃ | 3-CH₃—C₆H₄ | 3-Methylbut-2-en-1-yl |
| 1468 | CH₃ | 4-CH₃—C₆H₄ | H |
| 1469 | CH₃ | 4-CH₃—C₆H₄ | CH₃ |
| 1470 | CH₃ | 4-CH₃—C₆H₄ | C₂H₅ |
| 1471 | CH₃ | 4-CH₃—C₆H₄ | n-C₃H₇ |
| 1472 | CH₃ | 4-CH₃—C₆H₄ | i-C₃H₇ |
| 1473 | CH₃ | 4-CH₃—C₆H₄ | n-C₄H₉ |
| 1474 | CH₃ | 4-CH₃—C₆H₄ | t-C₄H₉ |
| 1475 | CH₃ | 4-CH₃—C₆H₄ | n-C₆H₁₃ |
| 1476 | CH₃ | 4-CH₃—C₆H₄ | Prop-1-en-3-yl |
| 1477 | CH₃ | 4-CH₃—C₆H₄ | (E)-1-Chloroprop-1-en-3-yl |
| 1478 | CH₃ | 4-CH₃—C₆H₄ | Propyn-3-yl |
| 1479 | CH₃ | 4-CH₃—C₆H₄ | 3-Methylbut-2-en-1-yl |
| 1480 | CH₃ | 2,3-(CH₃)₂—C₆H₃ | H |
| 1481 | CH₃ | 2,3-(CH₃)₂—C₆H₃ | CH₃ |
| 1482 | CH₃ | 2,3-(CH₃)₂—C₆H₃ | C₂H₅ |
| 1483 | CH₃ | 2,3-(CH₃)₂—C₆H₃ | n-C₃H₇ |
| 1484 | CH₃ | 2,3-(CH₃)₂—C₆H₃ | i-C₃H₇ |
| 1485 | CH₃ | 2,3-(CH₃)₂—C₆H₃ | n-C₄H₉ |
| 1486 | CH₃ | 2,3-(CH₃)₂—C₆H₃ | t-C₄H₉ |
| 1487 | CH₃ | 2,3-(CH₃)₂—C₆H₃ | n-C₆H₁₃ |
| 1488 | CH₃ | 2,3-(CH₃)₂—C₆H₃ | Prop-1-en-3-yl |
| 1489 | CH₃ | 2,3-(CH₃)₂—C₆H₃ | (E)-1-Chloroprop-1-en-3-yl |
| 1490 | CH₃ | 2,3-(CH₃)₂—C₆H₃ | Propyn-3-yl |
| 1491 | CH₃ | 2,3-(CH₃)₂—C₆H₃ | 3-Methylbut-2-en-1-yl |
| 1492 | CH₃ | 2,4-(CH₃)₂—C₆H₃ | H |
| 1493 | CH₃ | 2,4-(CH₃)₂—C₆H₃ | CH₃ |
| 1494 | CH₃ | 2,4-(CH₃)₂—C₆H₃ | C₂H₅ |
| 1495 | CH₃ | 2,4-(CH₃)₂—C₆H₃ | n-C₃H₇ |
| 1496 | CH₃ | 2,4-(CH₃)₂—C₆H₃ | i-C₃H₇ |
| 1497 | CH₃ | 2,4-(CH₃)₂—C₆H₃ | n-C₄H₉ |
| 1498 | CH₃ | 2,4-(CH₃)₂—C₆H₃ | t-C₄H₉ |
| 1499 | CH₃ | 2,4-(CH₃)₂—C₆H₃ | n-C₆H₁₃ |
| 1500 | CH₃ | 2,4-(CH₃)₂—C₆H₃ | Prop-1-en-3-yl |
| 1501 | CH₃ | 2,4-(CH₃)₂—C₆H₃ | (E)-1-Chloroprop-1-en-3-yl |

TABLE A-continued

| No. | $R^3$ | $R^4$ | $R^5$ |
|---|---|---|---|
| 1502 | $CH_3$ | 2,4-$(CH_3)_2$—$C_6H_3$ | Propyn-3-yl |
| 1503 | $CH_3$ | 2,4-$(CH_3)_2$—$C_6H_3$ | 3-Methylbut-2-en-1-yl |
| 1504 | $CH_3$ | 2,5-$(CH_3)_2$—$C_6H_3$ | H |
| 1505 | $CH_3$ | 2,5-$(CH_3)_2$—$C_6H_3$ | $CH_3$ |
| 1506 | $CH_3$ | 2,5-$(CH_3)_2$—$C_6H_3$ | $C_2H_5$ |
| 1507 | $CH_3$ | 2,5-$(CH_3)_2$—$C_6H_3$ | n-$C_3H_7$ |
| 1508 | $CH_3$ | 2,5-$(CH_3)_2$—$C_6H_3$ | i-$C_3H_7$ |
| 1509 | $CH_3$ | 2,5-$(CH_3)_2$—$C_6H_3$ | n-$C_4H_9$ |
| 1510 | $CH_3$ | 2,5-$(CH_3)_2$—$C_6H_3$ | t-$C_4H_9$ |
| 1511 | $CH_3$ | 2,5-$(CH_3)_2$—$C_6H_3$ | n-$C_6H_{13}$ |
| 1512 | $CH_3$ | 2,5-$(CH_3)_2$—$C_6H_3$ | Prop-1-en-3-yl |
| 1513 | $CH_3$ | 2,5-$(CH_3)_2$—$C_6H_3$ | (E)-1-Chloroprop-1-en-3-yl |
| 1514 | $CH_3$ | 2,5-$(CH_3)_2$—$C_6H_3$ | Propyn-3-yl |
| 1515 | $CH_3$ | 2,5-$(CH_3)_2$—$C_6H_3$ | 3-Methylbut-2-en-1-yl |
| 1516 | $CH_3$ | 2,6-$(CH_3)_2$—$C_6H_3$ | H |
| 1517 | $CH_3$ | 2,6-$(CH_3)_2$—$C_6H_3$ | $CH_3$ |
| 1518 | $CH_3$ | 2,6-$(CH_3)_2$—$C_6H_3$ | $C_2H_5$ |
| 1519 | $CH_3$ | 2,6-$(CH_3)_2$—$C_6H_3$ | n-$C_3H_7$ |
| 1520 | $CH_3$ | 2,6-$(CH_3)_2$—$C_6H_3$ | i-$C_3H_7$ |
| 1521 | $CH_3$ | 2,6-$(CH_3)_2$—$C_6H_3$ | n-$C_4H_9$ |
| 1522 | $CH_3$ | 2,6-$(CH_3)_2$—$C_6H_3$ | t-$C_4H_9$ |
| 1523 | $CH_3$ | 2,6-$(CH_3)_2$—$C_6H_3$ | n-$C_6H_{13}$ |
| 1524 | $CH_3$ | 2,6-$(CH_3)_2$—$C_6H_3$ | Prop-1-en-3-yl |
| 1525 | $CH_3$ | 2,6-$(CH_3)_2$—$C_6H_3$ | (E)-1-Chloroprop-1-en-3-yl |
| 1526 | $CH_3$ | 2,6-$(CH_3)_2$—$C_6H_3$ | Propyn-3-yl |
| 1527 | $CH_3$ | 2,6-$(CH_3)_2$—$C_6H_3$ | 3-Methylbut-2-en-1-yl |
| 1528 | $CH_3$ | 3,4-$(CH_3)_2$—$C_6H_3$ | H |
| 1529 | $CH_3$ | 3,4-$(CH_3)_2$—$C_6H_3$ | $CH_3$ |
| 1530 | $CH_3$ | 3,4-$(CH_3)_2$—$C_6H_3$ | $C_2H_5$ |
| 1531 | $CH_3$ | 3,4-$(CH_3)_2$—$C_6H_3$ | n-$C_3H_7$ |
| 1532 | $CH_3$ | 3,4-$(CH_3)_2$—$C_6H_3$ | i-$C_3H_7$ |
| 1533 | $CH_3$ | 3,4-$(CH_3)_2$—$C_6H_3$ | n-$C_4H_9$ |
| 1534 | $CH_3$ | 3,4-$(CH_3)_2$—$C_6H_3$ | t-$C_4H_9$ |
| 1535 | $CH_3$ | 3,4-$(CH_3)_2$—$C_6H_3$ | n-$C_6H_{13}$ |
| 1536 | $CH_3$ | 3,4-$(CH_3)_2$—$C_6H_3$ | Prop-1-en-3-yl |
| 1537 | $CH_3$ | 3,4-$(CH_3)_2$—$C_6H_3$ | (E)-1-Chloroprop-1-en-3-yl |
| 1538 | $CH_3$ | 3,4-$(CH_3)_2$—$C_6H_3$ | Propyn-3-yl |
| 1539 | $CH_3$ | 3,4-$(CH_3)_2$—$C_6H_3$ | 3-Methylbut-2-en-1-yl |
| 1540 | $CH_3$ | 3,5-$(CH_3)_2$—$C_6H_3$ | H |
| 1541 | $CH_3$ | 3,5-$(CH_3)_2$—$C_6H_3$ | $CH_3$ |
| 1542 | $CH_3$ | 3,5-$(CH_3)_2$—$C_6H_3$ | $C_2H_5$ |
| 1543 | $CH_3$ | 3,5-$(CH_3)_2$—$C_6H_3$ | n-$C_3H_7$ |
| 1544 | $CH_3$ | 3,5-$(CH_3)_2$—$C_6H_3$ | i-$C_3H_7$ |
| 1545 | $CH_3$ | 3,5-$(CH_3)_2$—$C_6H_3$ | n-$C_4H_9$ |
| 1546 | $CH_3$ | 3,5-$(CH_3)_2$—$C_6H_3$ | t-$C_4H_9$ |
| 1547 | $CH_3$ | 3,5-$(CH_3)_2$—$C_6H_3$ | n-$C_6H_{13}$ |
| 1548 | $CH_3$ | 3,5-$(CH_3)_2$—$C_6H_3$ | Prop-1-en-3-yl |
| 1549 | $CH_3$ | 3,5-$(CH_3)_2$—$C_6H_3$ | (E)-1-Chloroprop-1-en-3-yl |
| 1550 | $CH_3$ | 3,5-$(CH_3)_2$—$C_6H_3$ | Propyn-3-yl |
| 1551 | $CH_3$ | 3,5-$(CH_3)_2$—$C_6H_3$ | 3-Methylbut-2-en-1-yl |
| 1552 | $CH_3$ | 2-$C_2H_5$—$C_6H_4$ | H |
| 1553 | $CH_3$ | 2-$C_2H_5$—$C_6H_4$ | $CH_3$ |
| 1554 | $CH_3$ | 2-$C_2H_5$—$C_6H_4$ | $C_2H_5$ |
| 1555 | $CH_3$ | 2-$C_2H_5$—$C_6H_4$ | n-$C_3H_7$ |
| 1556 | $CH_3$ | 2-$C_2H_5$—$C_6H_4$ | i-$C_3H_7$ |
| 1557 | $CH_3$ | 2-$C_2H_5$—$C_6H_4$ | n-$C_4H_9$ |
| 1558 | $CH_3$ | 2-$C_2H_5$—$C_6H_4$ | t-$C_4H_9$ |
| 1559 | $CH_3$ | 2-$C_2H_5$—$C_6H_4$ | n-$C_6H_{13}$ |
| 1560 | $CH_3$ | 2-$C_2H_5$—$C_6H_4$ | Prop-1-en-3-yl |
| 1561 | $CH_3$ | 2-$C_2H_5$—$C_6H_4$ | (E)-1-Chloroprop-1-en-3-yl |
| 1562 | $CH_3$ | 2-$C_2H_5$—$C_6H_4$ | Propyn-3-yl |
| 1563 | $CH_3$ | 2-$C_2H_5$—$C_6H_4$ | 3-Methylbut-2-en-1-yl |
| 1564 | $CH_3$ | 3-$C_2H_5$—$C_6H_4$ | H |
| 1565 | $CH_3$ | 3-$C_2H_5$—$C_6H_4$ | $CH_3$ |
| 1566 | $CH_3$ | 3-$C_2H_5$—$C_6H_4$ | $C_2H_5$ |
| 1567 | $CH_3$ | 3-$C_2H_5$—$C_6H_4$ | n-$C_3H_7$ |
| 1568 | $CH_3$ | 3-$C_2H_5$—$C_6H_4$ | i-$C_3H_7$ |
| 1569 | $CH_3$ | 3-$C_2H_5$—$C_6H_4$ | n-$C_4H_9$ |
| 1570 | $CH_3$ | 3-$C_2H_5$—$C_6H_4$ | t-$C_4H_9$ |
| 1571 | $CH_3$ | 3-$C_2H_5$—$C_6H_4$ | n-$C_6H_{13}$ |
| 1572 | $CH_3$ | 3-$C_2H_5$—$C_6H_4$ | Prop-1-en-3-yl |
| 1573 | $CH_3$ | 3-$C_2H_5$—$C_6H_4$ | (E)-1-Chloroprop-1-en-3-yl |
| 1574 | $CH_3$ | 3-$C_2H_5$—$C_6H_4$ | Propyn-3-yl |
| 1575 | $CH_3$ | 3-$C_2H_5$—$C_6H_4$ | 3-Methylbut-2-en-1-yl |
| 1576 | $CH_3$ | 4-$C_2H_5$—$C_6H_4$ | H |
| 1577 | $CH_3$ | 4-$C_2H_5$—$C_6H_4$ | $CH_3$ |
| 1578 | $CH_3$ | 4-$C_2H_5$—$C_6H_4$ | $C_2H_5$ |

TABLE A-continued

| No. | R³ | R⁴ | R⁵ |
|---|---|---|---|
| 1579 | CH₃ | 4-C₂H₅—C₆H₄ | n-C₃H₇ |
| 1580 | CH₃ | 4-C₂H₅—C₆H₄ | i-C₃H₇ |
| 1581 | CH₃ | 4-C₂H₅—C₆H₄ | n-C₄H₉ |
| 1582 | CH₃ | 4-C₂H₅—C₆H₄ | t-C₄H₉ |
| 1583 | CH₃ | 4-C₂H₅—C₆H₄ | n-C₆H₁₃ |
| 1584 | CH₃ | 4-C₂H₅—C₆H₄ | Prop-1-en-3-yl |
| 1585 | CH₃ | 4-C₂H₅—C₆H₄ | (E)-1-Chloroprop-1-en-3-yl |
| 1586 | CH₃ | 4-C₂H₅—C₆H₄ | Propyn-3-yl |
| 1587 | CH₃ | 4-C₂H₅—C₆H₄ | 3-Methylbut-2-en-1-yl |
| 1588 | CH₃ | 2-i-C₃H₇—C₆H₄ | H |
| 1589 | CH₃ | 2-i-C₃H₇—C₆H₄ | CH₃ |
| 1590 | CH₃ | 2-i-C₃H₇—C₆H₄ | C₂H₅ |
| 1591 | CH₃ | 2-i-C₃H₇—C₆H₄ | n-C₃H₇ |
| 1592 | CH₃ | 2-i-C₃H₇—C₆H₄ | i-C₃H₇ |
| 1593 | CH₃ | 2-i-C₃H₇—C₆H₄ | n-C₄H₉ |
| 1594 | CH₃ | 2-i-C₃H₇—C₆H₄ | t-C₄H₉ |
| 1595 | CH₃ | 2-i-C₃H₇—C₆H₄ | n-C₆H₁₃ |
| 1596 | CH₃ | 2-i-C₃H₇—C₆H₄ | Prop-1-en-3-yl |
| 1597 | CH₃ | 2-i-C₃H₇—C₆H₄ | (E)-1-Chloroprop-1-en-3-yl |
| 1598 | CH₃ | 2-i-C₃H₇—C₆H₄ | Propyn-3-yl |
| 1599 | CH₃ | 2-i-C₃H₇—C₆H₄ | 3-Methylbut-2-en-1-yl |
| 1600 | CH₃ | 3-i-C₃H₇—C₆H₄ | H |
| 1601 | CH₃ | 3-i-C₃H₇—C₆H₄ | CH₃ |
| 1602 | CH₃ | 3-i-C₃H₇—C₆H₄ | C₂H₅ |
| 1603 | CH₃ | 3-i-C₃H₇—C₆H₄ | n-C₃H₇ |
| 1604 | CH₃ | 3-i-C₃H₇—C₆H₄ | i-C₃H₇ |
| 1605 | CH₃ | 3-i-C₃H₇—C₆H₄ | n-C₄H₉ |
| 1606 | CH₃ | 3-i-C₃H₇—C₆H₄ | t-C₄H₉ |
| 1607 | CH₃ | 3-i-C₃H₇—C₆H₄ | n-C₆H₁₃ |
| 1608 | CH₃ | 3-i-C₃H₇—C₆H₄ | Prop-1-en-3-yl |
| 1609 | CH₃ | 3-i-C₃H₇—C₆H₄ | (E)-1-Chloroprop-1-en-3-yl |
| 1610 | CH₃ | 3-i-C₃H₇—C₆H₄ | Propyn-3-yl |
| 1611 | CH₃ | 3-i-C₃H₇—C₆H₄ | 3-Methylbut-2-en-1-yl |
| 1612 | CH₃ | 4-i-C₃H₇—C₆H₄ | H |
| 1613 | CH₃ | 4-i-C₃H₇—C₆H₄ | CH₃ |
| 1614 | CH₃ | 4-i-C₃H₇—C₆H₄ | C₂H₅ |
| 1615 | CH₃ | 4-i-C₃H₇—C₆H₄ | n-C₃H₇ |
| 1616 | CH₃ | 4-i-C₃H₇—C₆H₄ | i-C₃H₇ |
| 1617 | CH₃ | 4-i-C₃H₇—C₆H₄ | n-C₄H₉ |
| 1618 | CH₃ | 4-i-C₃H₇—C₆H₄ | t-C₄H₉ |
| 1619 | CH₃ | 4-i-C₃H₇—C₆H₄ | n-C₆H₁₃ |
| 1620 | CH₃ | 4-i-C₃H₇—C₆H₄ | Prop-1-en-3-yl |
| 1621 | CH₃ | 4-i-C₃H₇—C₆H₄ | (E)-1-Chloroprop1-en-3-yl |
| 1622 | CH₃ | 4-i-C₃H₇—C₆H₄ | Propyn-3-yl |
| 1623 | CH₃ | 4-i-C₃H₇—C₆H₄ | 3-Methylbut-2-en-1-yl |
| 1624 | CH₃ | 2-OH—C₆H₄ | H |
| 1625 | CH₃ | 2-OH—C₆H₄ | CH₃ |
| 1626 | CH₃ | 2-OH—C₆H₄ | C₂H₅ |
| 1627 | CH₃ | 2-OH—C₆H₄ | n-C₃H₇ |
| 1628 | CH₃ | 2-OH—C₆H₄ | i-C₃H₇ |
| 1629 | CH₃ | 2-OH—C₆H₄ | n-C₄H₉ |
| 1630 | CH₃ | 2-OH—C₆H₄ | t-C₄H₉ |
| 1631 | CH₃ | 2-OH—C₆H₄ | n-C₆H₁₃ |
| 1632 | CH₃ | 2-OH—C₆H₄ | Prop-1-en-3-yl |
| 1633 | CH₃ | 2-OH—C₆H₄ | (E)-1-Chloroprop-1-en-3-yl |
| 1634 | CH₃ | 2-OH—C₆H₄ | Propyn-3-yl |
| 1635 | CH₃ | 2-OH—C₆H₄ | 3-Methylbut-2-en-1-yl |
| 1636 | CH₃ | 3-OH—C₆H₄ | H |
| 1637 | CH₃ | 3-OH—C₆H₄ | CH₃ |
| 1638 | CH₃ | 3-OH—C₆H₄ | C₂H₅ |
| 1639 | CH₃ | 3-OH—C₆H₄ | n-C₃H₇ |
| 1640 | CH₃ | 3-OH—C₆H₄ | i-C₃H₇ |
| 1641 | CH₃ | 3-OH—C₆H₄ | n-C₄H₉ |
| 1642 | CH₃ | 3-OH—C₆H₄ | t-C₄H₉ |
| 1643 | CH₃ | 3-OH—C₆H₄ | n-C₆H₁₃ |
| 1644 | CH₃ | 3-OH—C₆H₄ | Prop-1-en-3-yl |
| 1645 | CH₃ | 3-OH—C₆H₄ | (E)-1-Chloroprop-1-en-3-yl |
| 1646 | CH₃ | 3-OH—C₆H₄ | Propyn-3-yl |
| 1647 | CH₃ | 3-OH—C₆H₄ | 3-Methylbut-2-en-1-yl |
| 1648 | CH₃ | 4-OH—C₆H₄ | H |
| 1649 | CH₃ | 4-OH—C₆H₄ | CH₃ |
| 1650 | CH₃ | 4-OH—C₆H₄ | C₂H₅ |
| 1651 | CH₃ | 4-OH—C₆H₄ | n-C₃H₇ |
| 1652 | CH₃ | 4-OH—C₆H₄ | i-C₃H₇ |
| 1653 | CH₃ | 4-OH—C₆H₄ | n-C₄H₉ |
| 1654 | CH₃ | 4-OH—C₆H₄ | t-C₄H₉ |
| 1655 | CH₃ | 4-OH—C₆H₄ | n-C₆H₁₃ |

TABLE A-continued

| No. | R³ | R⁴ | R⁵ |
|---|---|---|---|
| 1656 | $CH_3$ | 4-OH—$C_6H_4$ | Prop-1-en-3-yl |
| 1657 | $CH_3$ | 4-OH—$C_6H_4$ | (E)-1-Chloroprop-1-en-3-yl |
| 1658 | $CH_3$ | 4-OH—$C_6H_4$ | Propyn-3-yl |
| 1659 | $CH_3$ | 4-OH—$C_6H_4$ | 3-Methylbut-2-en-1-yl |
| 1660 | $CH_3$ | 2-$OCH_3$—$C_6H_4$ | H |
| 1661 | $CH_3$ | 2-$OCH_3$—$C_6H_4$ | $CH_3$ |
| 1662 | $CH_3$ | 2-$OCH_3$—$C_6H_4$ | $C_2H_5$ |
| 1663 | $CH_3$ | 2-$OCH_3$—$C_6H_4$ | n-$C_3H_7$ |
| 1664 | $CH_3$ | 2-$OCH_3$—$C_6H_4$ | i-$C_3H_7$ |
| 1665 | $CH_3$ | 2-$OCH_3$—$C_6H_4$ | n-$C_4H_9$ |
| 1666 | $CH_3$ | 2-$OCH_3$—$C_6H_4$ | t-$C_4H_9$ |
| 1667 | $CH_3$ | 2-$OCH_3$—$C_6H_4$ | n-$C_6H_{13}$ |
| 1668 | $CH_3$ | 2-$OCH_3$—$C_6H_4$ | Prop-1-en-3-yl |
| 1669 | $CH_3$ | 2-$OCH_3$—$C_6H_4$ | (E)-1-Chloroprop-1-en-3-yl |
| 1670 | $CH_3$ | 2-$OCH_3$—$C_6H_4$ | Propyn-3-yl |
| 1671 | $CH_3$ | 2-$OCH_3$—$C_6H_4$ | 3-Methylbut-2-en-1-yl |
| 1672 | $CH_3$ | 3-$OCH_3$—$C_6H_4$ | H |
| 1673 | $CH_3$ | 3-$OCH_3$—$C_6H_4$ | $CH_3$ |
| 1674 | $CH_3$ | 3-$OCH_3$—$C_6H_4$ | $C_2H_5$ |
| 1675 | $CH_3$ | 3-$OCH_3$—$C_6H_4$ | n-$C_3H_7$ |
| 1676 | $CH_3$ | 3-$OCH_3$—$C_6H_4$ | i-$C_3H_7$ |
| 1677 | $CH_3$ | 3-$OCH_3$—$C_6H_4$ | n-$C_4H_9$ |
| 1678 | $CH_3$ | 3-$OCH_3$—$C_6H_4$ | t-$C_4H_9$ |
| 1679 | $CH_3$ | 3-$OCH_3$—$C_6H_4$ | n-$C_6H_{13}$ |
| 1680 | $CH_3$ | 3-$OCH_3$—$C_6H_4$ | Prop-1-en-3-yl |
| 1681 | $CH_3$ | 3-$OCH_3$—$C_6H_4$ | (E)-1-Chloroprop-1-en-3-yl |
| 1682 | $CH_3$ | 3-$OCH_3$—$C_6H_4$ | Propyn-3-yl |
| 1683 | $CH_3$ | 3-$OCH_3$—$C_6H_4$ | 3-Methylbut-2-en-1-yl |
| 1684 | $CH_3$ | 4-$OCH_3$—$C_6H_4$ | H |
| 1685 | $CH_3$ | 4-$OCH_3$—$C_6H_4$ | $CH_3$ |
| 1686 | $CH_3$ | 4-$OCH_3$—$C_6H_4$ | $C_2H_5$ |
| 1687 | $CH_3$ | 4-$OCH_3$—$C_6H_4$ | n-$C_3H_7$ |
| 1688 | $CH_3$ | 4-$OCH_3$—$C_6H_4$ | i-$C_3H_7$ |
| 1689 | $CH_3$ | 4-$OCH_3$—$C_6H_4$ | n-$C_4H_9$ |
| 1690 | $CH_3$ | 4-$OCH_3$—$C_6H_4$ | t-$C_4H_9$ |
| 1691 | $CH_3$ | 4-$OCH_3$—$C_6H_4$ | n-$C_6H_{13}$ |
| 1692 | $CH_3$ | 4-$OCH_3$—$C_6H_4$ | Prop-1-en-3-yl |
| 1693 | $CH_3$ | 4-$OCH_3$—$C_6H_4$ | (E)1-Chloroprop-1-en-3-yl |
| 1694 | $CH_3$ | 4-$OCH_3$—$C_6H_4$ | Propyn-3-yl |
| 1695 | $CH_3$ | 4-$OCH_3$—$C_6H_4$ | 3-Methylbut-2-en-1-yl |
| 1696 | $CH_3$ | 2-$OC_2H_5$—$C_6H_4$ | H |
| 1697 | $CH_3$ | 2-$OC_2H_5$—$C_6H_4$ | $CH_3$ |
| 1698 | $CH_3$ | 2-$OC_2H_5$—$C_6H_4$ | $C_2H_5$ |
| 1699 | $CH_3$ | 2-$OC_2H_5$—$C_6H_4$ | n-$C_3H_7$ |
| 1700 | $CH_3$ | 2-$OC_2H_5$—$C_6H_4$ | i-$C_3H_7$ |
| 1701 | $CH_3$ | 2-$OC_2H_5$—$C_6H_4$ | n-$C_4H_9$ |
| 1702 | $CH_3$ | 2-$OC_2H_5$—$C_6H_4$ | t-$C_4H_9$ |
| 1703 | $CH_3$ | 2-$OC_2H_5$—$C_6H_4$ | n-$C_6H_{13}$ |
| 1704 | $CH_3$ | 2-$OC_2H_5$—$C_6H_4$ | Prop-1-en-3-yl |
| 1705 | $CH_3$ | 2-$OC_2H_5$—$C_6H_4$ | (E)-1-Chloroprop-1-en-3-yl |
| 1706 | $CH_3$ | 2-$OC_2H_5$—$C_6H_4$ | Propyn-3-yl |
| 1707 | $CH_3$ | 2-$OC_2H_5$—$C_6H_4$ | 3-Methylbut-2-en-1-yl |
| 1708 | $CH_3$ | 3-$OC_2H_5$—$C_6H_4$ | H |
| 1709 | $CH_3$ | 3-$OC_2H_5$—$C_6H_4$ | $CH_3$ |
| 1710 | $CH_3$ | 3-$OC_2H_5$—$C_6H_4$ | $C_2H_5$ |
| 1711 | $CH_3$ | 3-$OC_2H_5$—$C_6H_4$ | n-$C_3H_7$ |
| 1712 | $CH_3$ | 3-$OC_2H_5$—$C_6H_4$ | i-$C_3H_7$ |
| 1713 | $CH_3$ | 3-$OC_2H_5$—$C_6H_4$ | n-$C_4H_9$ |
| 1714 | $CH_3$ | 3-$OC_2H_5$—$C_6H_4$ | t-$C_4H_9$ |
| 1715 | $CH_3$ | 3-$OC_2H_5$—$C_6H_4$ | n-$C_6H_{13}$ |
| 1716 | $CH_3$ | 3-$OC_2H_5$—$C_6H_4$ | Prop-1-en-3-yl |
| 1717 | $CH_3$ | 3-$OC_2H_5$—$C_6H_4$ | (E)-1-Chloroprop-1-en-3-yl |
| 1718 | $CH_3$ | 3-$OC_2H_5$—$C_6H_4$ | Propyn-3-yl |
| 1719 | $CH_3$ | 3-$OC_2H_5$—$C_6H_4$ | 3-Methylbut-2-en-1-yl |
| 1720 | $CH_3$ | 4-$OC_2H_5$—$C_6H_4$ | H |
| 1721 | $CH_3$ | 4-$OC_2H_5$—$C_6H_4$ | $CH_3$ |
| 1722 | $CH_3$ | 4-$OC_2H_5$—$C_6H_4$ | $C_2H_5$ |
| 1723 | $CH_3$ | 4-$OC_2H_5$—$C_6H_4$ | n-$C_3H_7$ |
| 1724 | $CH_3$ | 4-$OC_2H_5$—$C_6H_4$ | i-$C_3H_7$ |
| 1725 | $CH_3$ | 4-$OC_2H_5$—$C_6H_4$ | n-$C_4H_9$ |
| 1726 | $CH_3$ | 4-$OC_2H_5$—$C_6H_4$ | t-$C_4H_9$ |
| 1727 | $CH_3$ | 4-$OC_2H_5$—$C_6H_4$ | n-$C_6H_{13}$ |
| 1728 | $CH_3$ | 4-$OC_2H_5$—$C_6H_4$ | Prop-1-en-3-yl |
| 1729 | $CH_3$ | 4-$OC_2H_5$—$C_6H_4$ | (E)-1-Chloroprop-1-en-3-yl |
| 1730 | $CH_3$ | 4-$OC_2H_5$—$C_6H_4$ | Propyn-3-yl |
| 1731 | $CH_3$ | 4-$OC_2H_5$—$C_6H_4$ | 3-Methylbut-2-en-1-yl |
| 1732 | $CH_3$ | 2-O-(i-$C_3H_7$)—$C_6H_4$ | H |

TABLE A-continued

| No. | R³ | R⁴ | R⁵ |
|---|---|---|---|
| 1733 | CH₃ | 2-O-(i-C₃H₇)—C₆H₄ | CH₃ |
| 1734 | CH₃ | 2-O-(i-C₃H₇)—C₆H₄ | C₂H₅ |
| 1735 | CH₃ | 2-O-(i-C₃H₇)—C₆H₄ | n-C₃H₇ |
| 1736 | CH₃ | 2-O-(i-C₃H₇)—C₆H₄ | i-C₃H₇ |
| 1737 | CH₃ | 2-O-(i-C₃H₇)—C₆H₄ | n-C₄H₉ |
| 1738 | CH₃ | 2-O-(i-C₃H₇)—C₆H₄ | t-C₄H₉ |
| 1739 | CH₃ | 2-O-(i-C₃H₇)—C₆H₄ | n-C₆H₁₃ |
| 1740 | CH₃ | 2-O-(i-C₃H₇)—C₆H₄ | Prop-1-en-3-yl |
| 1741 | CH₃ | 2-O-(i-C₃H₇)—C₆H₄ | (E)-1-Chloroprop-1-en-3-yl |
| 1742 | CH₃ | 2-O-(i-C₃H₇)—C₆H₄ | Propyn-3-yl |
| 1743 | CH₃ | 2-O-(i-C₃H₇)—C₆H₄ | 3-Methylbut-2-en-1-yl |
| 1744 | CH₃ | 3-O-(i-C₃H₇)—C₆H₄ | H |
| 1745 | CH₃ | 3-O-(i-C₃H₇)—C₆H₄ | CH₃ |
| 1746 | CH₃ | 3-O-(i-C₃H₇)—C₆H₄ | C₂H₅ |
| 1747 | CH₃ | 3-O-(i-C₃H₇)—C₆H₄ | n-C₃H₇ |
| 1748 | CH₃ | 3-O-(i-C₃H₇)—C₆H₄ | i-C₃H₇ |
| 1749 | CH₃ | 3-O-(i-C₃H₇)—C₆H₄ | n-C₄H₉ |
| 1750 | CH₃ | 3-O-(i-C₃H₇)—C₆H₄ | t-C₄H₉ |
| 1751 | CH₃ | 3-O-(i-C₃H₇)—C₆H₄ | n-C₆H₁₃ |
| 1752 | CH₃ | 3-O-(i-C₃H₇)—C₆H₄ | Prop-1-en-3-yl |
| 1753 | CH₃ | 3-O-(i-C₃H₇)—C₆H₄ | (E)-1-Chloroprop-1-en-3-yl |
| 1754 | CH₃ | 3-O-(i-C₃H₇)—C₆H₄ | Propyn-3-yl |
| 1755 | CH₃ | 3-O-(i-C₃H₇)—C₆H₄ | 3-Methylbut-2-en-1-yl |
| 1756 | CH₃ | 4-O-(i-C₃H₇)—C₆H₄ | H |
| 1757 | CH₃ | 4-O-(i-C₃H₇)—C₆H₄ | CH₃ |
| 1758 | CH₃ | 4-O-(i-C₃H₇)—C₆H₄ | C₂H₅ |
| 1759 | CH₃ | 4-O-(i-C₃H₇)—C₆H₄ | n-C₃H₇ |
| 1760 | CH₃ | 4-O-(i-C₃H₇)—C₆H₄ | i-C₃H₇ |
| 1761 | CH₃ | 4-O-(i-C₃H₇)—C₆H₄ | n-C₄H₉ |
| 1762 | CH₃ | 4-O-(i-C₃H₇)—C₆H₄ | t-C₄H₉ |
| 1763 | CH₃ | 4-O-(i-C₃H₇)—C₆H₄ | n-C₆H₁₃ |
| 1764 | CH₃ | 4-O-(i-C₃H₇)—C₆H₄ | Prop-1-en-3-yl |
| 1765 | CH₃ | 4-O-(i-C₃H₇)—C₆H₄ | (E)-1-Chloroprop-1-en-3-yl |
| 1766 | CH₃ | 4-O-(i-C₃H₇)—C₆H₄ | Propyn-3-yl |
| 1767 | CH₃ | 4-O-(i-C₃H₇)—C₆H₄ | 3-Methylbut-2-en-1-yl |
| 1768 | CH₃ | 2-O-(t-C₄H₉)—C₆H₄ | H |
| 1769 | CH₃ | 2-O-(t-C₄H₉)—C₆H₄ | CH₃ |
| 1770 | CH₃ | 2-O-(t-C₄H₉)—C₆H₄ | C₂H₅ |
| 1771 | CH₃ | 2-O-(t-C₄H₉)—C₆H₄ | n-C₃H₇ |
| 1772 | CH₃ | 2-O-(t-C₄H₉)—C₆H₄ | i-C₃H₇ |
| 1773 | CH₃ | 2-O-(t-C₄H₉)—C₆H₄ | n-C₄H₉ |
| 1774 | CH₃ | 2-O-(t-C₄H₉)—C₆H₄ | t-C₄H₉ |
| 1775 | CH₃ | 2-O-(t-C₄H₉)—C₆H₄ | n-C₆H₁₃ |
| 1776 | CH₃ | 2-O-(t-C₄H₉)—C₆H₄ | Prop-1-en-3-yl |
| 1777 | CH₃ | 2-O-(t-C₄H₉)—C₆H₄ | (E)-1-Chloroprop-1-en-3-yl |
| 1778 | CH₃ | 2-O-(t-C₄H₉)—C₆H₄ | Propyn-3-yl |
| 1779 | CH₃ | 2-O-(t-C₄H₉)—C₆H₄ | 3-Methylbut-2-en-1-yl |
| 1780 | CH₃ | 3-O-(t-C₄H₉)—C₆H₄ | H |
| 1781 | CH₃ | 3-O-(t-C₄H₉)—C₆H₄ | CH₃ |
| 1782 | CH₃ | 3-O-(t-C₄H₉)—C₆H₄ | C₂H₅ |
| 1783 | CH₃ | 3-O-(t-C₄H₉)—C₆H₄ | n-C₃H₇ |
| 1784 | CH₃ | 3-O-(t-C₄H₉)—C₆H₄ | i-C₃H₇ |
| 1785 | CH₃ | 3-O-(t-C₄H₉)—C₆H₄ | n-C₄H₉ |
| 1786 | CH₃ | 3-O-(t-C₄H₉)—C₆H₄ | t-C₄H₉ |
| 1787 | CH₃ | 3-O-(t-C₄H₉)—C₆H₄ | n-C₆H₁₃ |
| 1788 | CH₃ | 3-O-(t-C₄H₉)—C₆H₄ | Prop-1-en-3-yl |
| 1789 | CH₃ | 3-O-(t-C₄H₉)—C₆H₄ | (E)-1-Chloroprop-1-en-3-yl |
| 1790 | CH₃ | 3-O-(t-C₄H₉)—C₆H₄ | Propyn-3-yl |
| 1791 | CH₃ | 3-O-(t-C₄H₉)—C₆H₄ | 3-Methylbut-2-en-1-yl |
| 1792 | CH₃ | 4-O-(t-C₄H₉)—C₆H₄ | H |
| 1793 | CH₃ | 4-O-(t-C₄H₉)—C₆H₄ | CH₃ |
| 1794 | CH₃ | 4-O-(t-C₄H₉)—C₆H₄ | C₂H₅ |
| 1795 | CH₃ | 4-O-(t-C₄H₉)—C₆H₄ | n-C₃H₇ |
| 1796 | CH₃ | 4-O-(t-C₄H₉)—C₆H₄ | i-C₃H₇ |
| 1797 | CH₃ | 4-O-(t-C₄H₉)—C₆H₄ | n-C₄H₉ |
| 1798 | CH₃ | 4-O-(t-C₄H₉)—C₆H₄ | t-C₄H₉ |
| 1799 | CH₃ | 4-O-(t-C₄H₉)—C₆H₄ | n-C₆H₁₃ |
| 1800 | CH₃ | 4-O-(t-C₄H₉)—C₆H₄ | Prop-1-en-3-yl |
| 1801 | CH₃ | 4-O-(t-C₄H₉)—C₆H₄ | (E)-1-Chloroprop-1-en-3-yl |
| 1802 | CH₃ | 4-O-(t-C₄H₉)—C₆H₄ | Propyn-3-yl |
| 1803 | CH₃ | 4-O-(t-C₄H₉)—C₆H₄ | 3-Methylbut-2-en-1-yl |
| 1804 | CH₃ | 2-CF₃—C₆H₄ | H |
| 1805 | CH₃ | 2-CF₃—C₆H₄ | CH₃ |
| 1806 | CH₃ | 2-CF₃—C₆H₄ | C₂H₅ |
| 1807 | CH₃ | 2-CF₃—C₆H₄ | n-C₃H₇ |
| 1808 | CH₃ | 2-CF₃—C₆H₄ | i-C₃H₇ |
| 1809 | CH₃ | 2-CF₃—C₆H₄ | n-C₄H₉ |

TABLE A-continued

| No. | R³ | R⁴ | R⁵ |
|---|---|---|---|
| 1810 | CH₃ | 2-CF₃—C₆H₄ | t-C₄H₉ |
| 1811 | CH₃ | 2-CF₃—C₆H₄ | n-C₆H₁₃ |
| 1812 | CH₃ | 2-CF₃—C₆H₄ | Prop-1-en-3-yl |
| 1813 | CH₃ | 2-CF₃—C₆H₄ | (E)-1-Chloroprop-1-en-3-yl |
| 1814 | CH₃ | 2-CF₃—C₆H₄ | Propyn-3-yl |
| 1815 | CH₃ | 2-CF₃—C₆H₄ | 3-Methylbut-2-en-1-yl |
| 1816 | CH₃ | 3-CF₃—C₆H₄ | H |
| 1817 | CH₃ | 3-CF₃—C₆H₄ | CH₃ |
| 1818 | CH₃ | 3-CF₃—C₆H₄ | C₂H₅ |
| 1819 | CH₃ | 3-CF₃—C₆H₄ | n-C₃H₇ |
| 1820 | CH₃ | 3-CF₃—C₆H₄ | i-C₃H₇ |
| 1821 | CH₃ | 3-CF₃—C₆H₄ | n-C₄H₉ |
| 1822 | CH₃ | 3-CF₃—C₆H₄ | t-C₄H₉ |
| 1823 | CH₃ | 3-CF₃—C₆H₄ | n-C₆H₁₃ |
| 1824 | CH₃ | 3-CF₃—C₆H₄ | Prop-1-en-3-yl |
| 1825 | CH₃ | 3-CF₃—C₆H₄ | (E)-1-Chloroprop-1-en-3-yl |
| 1826 | CH₃ | 3-CF₃—C₆H₄ | Propyn-3-yl |
| 1827 | CH₃ | 3-CF₃—C₆H₄ | 3-Methylbut-2-en-1-yl |
| 1828 | CH₃ | 4-CF₃—C₆H₄ | H |
| 1829 | CH₃ | 4-CF₃—C₆H₄ | CH₃ |
| 1830 | CH₃ | 4-CF₃—C₆H₄ | C₂H₅ |
| 1831 | CH₃ | 4-CF₃—C₆H₄ | n-C₃H₇ |
| 1832 | CH₃ | 4-CF₃—C₆H₄ | i-C₃H₇ |
| 1833 | CH₃ | 4-CF₃—C₆H₄ | n-C₄H₉ |
| 1834 | CH₃ | 4-CF₃—C₆H₄ | t-C₄H₉ |
| 1835 | CH₃ | 4-CF₃—C₆H₄ | n-C₆H₁₃ |
| 1836 | CH₃ | 4-CF₃—C₆H₄ | Prop-1-en-3-yl |
| 1837 | CH₃ | 4-CF₃—C₆H₄ | (E)-1-Chloroprop-1-en-3-yl |
| 1838 | CH₃ | 4-CF₃—C₆H₄ | Propyn-3-yl |
| 1839 | CH₃ | 4-CF₃—C₆H₄ | 3-Methylbut-2-en-1-yl |
| 1840 | CH₃ | 2-NH₂—C₆H₄ | H |
| 1841 | CH₃ | 2-NH₂—C₆H₄ | CH₃ |
| 1842 | CH₃ | 2-NH₂—C₆H₄ | C₂H₅ |
| 1843 | CH₃ | 2-NH₂—C₆H₄ | n-C₃H₇ |
| 1844 | CH₃ | 2-NH₂—C₆H₄ | i-C₃H₇ |
| 1845 | CH₃ | 2-NH₂—C₆H₄ | n-C₄H₉ |
| 1846 | CH₃ | 2-NH₂—C₆H₄ | t-C₄H₉ |
| 1847 | CH₃ | 2-NH₂—C₆H₄ | n-C₆H₁₃ |
| 1848 | CH₃ | 2-NH₂—C₆H₄ | Prop-1-en-3-yl |
| 1849 | CH₃ | 2-NH₂—C₆H₄ | (E)-1-Chloroprop-1-en-3-yl |
| 1850 | CH₃ | 2-NH₂—C₆H₄ | Propyn-3-yl |
| 1851 | CH₃ | 2-NH₂—C₆H₄ | 3-Methylbut-2-en-1-yl |
| 1852 | CH₃ | 3-NH₂—C₆H₄ | H |
| 1853 | CH₃ | 3-NH₂—C₆H₄ | CH₃ |
| 1854 | CH₃ | 3-NH₂—C₆H₄ | C₂H₅ |
| 1855 | CH₃ | 3-NH₂—C₆H₄ | n-C₃H₇ |
| 1856 | CH₃ | 3-NH₂—C₆H₄ | i-C₃H₇ |
| 1857 | CH₃ | 3-NH₂—C₆H₄ | n-C₄H₉ |
| 1858 | CH₃ | 3-NH₂—C₆H₄ | t-C₄H₉ |
| 1859 | CH₃ | 3-NH₂—C₆H₄ | n-C₆H₁₃ |
| 1860 | CH₃ | 3-NH₂—C₆H₄ | Prop-1-en-3-yl |
| 1861 | CH₃ | 3-NH₂—C₆H₄ | (E)-1-Chloroprop-1-en-3-yl |
| 1862 | CH₃ | 3-NH₂—C₆H₄ | Propyn-3-yl |
| 1863 | CH₃ | 3-NH₂—C₆H₄ | 3-Methylbut-2-en-1-yl |
| 1864 | CH₃ | 4-NH₂—C₆H₄ | H |
| 1865 | CH₃ | 4-NH₂—C₆H₄ | CH₃ |
| 1866 | CH₃ | 4-NH₂—C₆H₄ | C₂H₅ |
| 1867 | CH₃ | 4-NH₂—C₆H₄ | n-C₃H₇ |
| 1868 | CH₃ | 4-NH₂—C₆H₄ | i-C₃H₇ |
| 1869 | CH₃ | 4-NH₂—C₆H₄ | n-C₄H₉ |
| 1870 | CH₃ | 4-NH₂—C₆H₄ | t-C₄H₉ |
| 1871 | CH₃ | 4-NH₂—C₆H₄ | n-C₆H₁₃ |
| 1872 | CH₃ | 4-NH₂—C₆H₄ | Prop-1-en-3-yl |
| 1873 | CH₃ | 4-NH₂—C₆H₄ | (E)-1-Chloroprop-1-en-3-yl |
| 1874 | CH₃ | 4-NH₂—C₆H₄ | Propyn-3-yl |
| 1875 | CH₃ | 4-NH₂—C₆H₄ | 3-Methylbut-2-en-1-yl |
| 1876 | CH₃ | 2-NMe₂—C₆H₄ | H |
| 1877 | CH₃ | 2-NMe₂—C₆H₄ | CH₃ |
| 1878 | CH₃ | 2-NMe₂—C₆H₄ | C₂H₅ |
| 1879 | CH₃ | 2-NMe₂—C₆H₄ | n-C₃H₇ |
| 1880 | CH₃ | 2-NMe₂—C₆H₄ | i-C₃H₇ |
| 1881 | CH₃ | 2-NMe₂—C₆H₄ | n-C₄H₉ |
| 1882 | CH₃ | 2-NMe₂—C₆H₄ | t-C₄H₉ |
| 1883 | CH₃ | 2-NMe₂—C₆H₄ | n-C₆H₁₃ |
| 1884 | CH₃ | 2-NMe₂—C₆H₄ | Prop-1-en-3-yl |
| 1885 | CH₃ | 2-NMe₂—C₆H₄ | (E)-1-Chloroprop-1-en-3-yl |
| 1886 | CH₃ | 2-NMe₂—C₆H₄ | Propyn-3-yl |

TABLE A-continued

| No. | R³ | R⁴ | R⁵ |
|---|---|---|---|
| 1887 | CH₃ | 2-NMe₂—C₆H₄ | 3-Methylbut-2-en-1-yl |
| 1888 | CH₃ | 3-NMe₂—C₆H₄ | H |
| 1889 | CH₃ | 3-NMe₂—C₆H₄ | CH₃ |
| 1890 | CH₃ | 3-NMe₂—C₆H₄ | C₂H₅ |
| 1891 | CH₃ | 3-NMe₂—C₆H₄ | n-C₃H₇ |
| 1892 | CH₃ | 3-NMe₂—C₆H₄ | i-C₃H₇ |
| 1893 | CH₃ | 3-NMe₂—C₆H₄ | n-C₄H₉ |
| 1894 | CH₃ | 3-NMe₂—C₆H₄ | t-C₄H₉ |
| 1895 | CH₃ | 3-NMe₂—C₆H₄ | n-C₆H₁₃ |
| 1896 | CH₃ | 3-NMe₂—C₆H₄ | Prop-1-en-3-yl |
| 1897 | CH₃ | 3-NMe₂—C₆H₄ | (E)-1-Chloroprop-1-en-3-yl |
| 1898 | CH₃ | 3-NMe₂—C₆H₄ | Propyn-3-yl |
| 1899 | CH₃ | 3-NMe₂—C₆H₄ | 3-Methylbut-2-en-1-yl |
| 1900 | CH₃ | 4-NMe₂—C₆H₄ | H |
| 1901 | CH₃ | 4-NMe₂—C₆H₄ | CH₃ |
| 1902 | CH₃ | 4-NMe₂—C₆H₄ | C₂H₅ |
| 1903 | CH₃ | 4-NMe₂—C₆H₄ | n-C₃H₇ |
| 1904 | CH₃ | 4-NMe₂—C₆H₄ | i-C₃H₇ |
| 1905 | CH₃ | 4-NMe₂—C₆H₄ | n-C₄H₉ |
| 1906 | CH₃ | 4-NMe₂—C₆H₄ | t-C₄H₉ |
| 1907 | CH₃ | 4-NMe₂—C₆H₄ | n-C₆H₁₃ |
| 1908 | CH₃ | 4-NMe₂—C₆H₄ | Prop-1-en-3-yl |
| 1909 | CH₃ | 4-NMe₂—C₆H₄ | (E)-1-Chloroprop-1-en-3-yl |
| 1910 | CH₃ | 4-NMe₂—C₆H₄ | Propyn-3-yl |
| 1911 | CH₃ | 4-NMe₂—C₆H₄ | 3-Methylbut-2-en-1-yl |
| 1912 | CH₃ | 2-Aminothiocarbonyl-C₆H₄ | H |
| 1913 | CH₃ | 2-Aminothiocarbonyl-C₆H₄ | CH₃ |
| 1914 | CH₃ | 2-Aminothiocarbonyl-C₆H₄ | C₂H₅ |
| 1915 | CH₃ | 2-Aminothiocarbonyl-C₆H₄ | n-C₃H₇ |
| 1916 | CH₃ | 2-Aminothiocarbonyl-C₆H₄ | i-C₃H₇ |
| 1917 | CH₃ | 2-Aminothiocarbonyl-C₆H₄ | n-C₄H₉ |
| 1918 | CH₃ | 2-Aminothiocarbonyl-C₆H₄ | t-C₄H₉ |
| 1919 | CH₃ | 2-Aminothiocarbonyl-C₆H₄ | n-C₆H₁₃ |
| 1920 | CH₃ | 2-Aminothiocarbonyl-C₆H₄ | Prop-1-en-3-yl |
| 1921 | CH₃ | 2-Aminothiocarbonyl-C₆H₄ | (E)-1-Chloroprop-1-en-3-yl |
| 1922 | CH₃ | 2-Aminothiocarbonyl-C₆H₄ | Propyn-3-yl |
| 1923 | CH₃ | 2-Aminothiocarbonyl-C₆H₄ | 3-Methylbut-2-en-1-yl |
| 1924 | CH₃ | 3-Aminothiocarbonyl-C₆H₄ | H |
| 1925 | CH₃ | 3-Aminothiocarbonyl-C₆H₄ | CH₃ |
| 1926 | CH₃ | 3-Aminothiocarbonyl-C₆H₄ | C₂H₅ |
| 1927 | CH₃ | 3-Aminothiocarbonyl-C₆H₄ | n-C₃H₇ |
| 1928 | CH₃ | 3-Aminothiocarbonyl-C₆H₄ | i-C₃H₇ |
| 1929 | CH₃ | 3-Aminothiocarbonyl-C₆H₄ | n-C₄H₉ |
| 1930 | CH₃ | 3-Aminothiocarbonyl-C₆H₄ | t-C₄H₉ |
| 1931 | CH₃ | 3-Aminothiocarbonyl-C₆H₄ | n-C₆H₁₃ |
| 1932 | CH₃ | 3-Aminothiocarbonyl-C₆H₄ | Prop-1-en-3-yl |
| 1933 | CH₃ | 3-Aminothiocarbonyl-C₆H₄ | (E)-1-Chloroprop-1-en-3-yl |
| 1934 | CH₃ | 3-Aminothiocarbonyl-C₆H₄ | Propyn-3-yl |
| 1935 | CH₃ | 3-Aminothiocarbonyl-C₆H₄ | 3-Methylbut-2-en-1-yl |
| 1936 | CH₃ | 4-Aminothiocarbonyl-C₆H₄ | H |
| 1937 | CH₃ | 4-Amimothiocarbonyl-C₆H₄ | CH₃ |
| 1938 | CH₃ | 4-Aminothiocarbonyl-C₆H₄ | C₂H₅ |
| 1939 | CH₃ | 4-Aminothiocarbonyl-C₆H₄ | n-C₃H₇ |
| 1940 | CH₃ | 4-Aminothiocarbonyl-C₆H₄ | i-C₃H₇ |
| 1941 | CH₃ | 4-Aminothiocarbonyl-C₆H₄ | n-C₄H₉ |
| 1942 | CH₃ | 4-Aminothiocarbonyl-C₆H₄ | t-C₄H₉ |
| 1943 | CH₃ | 4-Aminothiocarbonyl-C₆H₄ | n-C₆H₁₃ |
| 1944 | CH₃ | 4-Aminothiocarbonyl-C₆H₄ | Prop-1-en-3-yl |
| 1945 | CH₃ | 4-Aminothiocarbonyl-C₆H₄ | (E)-1-Chloroprop-1-en-3-yl |
| 1946 | CH₃ | 4-Aminothiocarbonyl-C₆H₄ | Propyn-3-yl |
| 1947 | CH₃ | 4-Aminothiocarbonyl-C₆H₄ | 3-Methylbut-2-en-1-yl |
| 1948 | CH₃ | 2-OCF₃—C₆H₄ | H |
| 1949 | CH₃ | 2-OCF₃—C₆H₄ | CH₃ |
| 1950 | CH₃ | 2-OCF₃—C₆H₄ | C₂H₅ |
| 1951 | CH₃ | 2-OCF₃—C₆H₄ | n-C₃H₇ |
| 1952 | CH₃ | 2-OCF₃—C₆H₄ | i-C₃H₇ |
| 1953 | CH₃ | 2-OCF₃—C₆H₄ | n-C₄H₉ |
| 1954 | CH₃ | 2-OCF₃—C₆H₄ | t-C₄H₉ |
| 1955 | CH₃ | 2-OCF₃—C₆H₄ | n-C₆H₁₃ |
| 1956 | CH₃ | 2-OCF₃—C₆H₄ | Prop-1-en-3-yl |
| 1957 | CH₃ | 2-OCF₃—C₆H₄ | (E)-1-Chloroprop-1-en-3-yl |
| 1958 | CH₃ | 2-OCF₃—C₆H₄ | Propyn-3-yl |
| 1959 | CH₃ | 2-OCF₃—C₆H₄ | 3-Methylbut-2-en-1-yl |
| 1960 | CH₃ | 3-OCF₃—C₆H₄ | H |
| 1961 | CH₃ | 3-OCF₃—C₆H₄ | CH₃ |
| 1962 | CH₃ | 3-OCF₃—C₆H₄ | C₂H₅ |
| 1963 | CH₃ | 3-OCF₃—C₆H₄ | n-C₃H₇ |

TABLE A-continued

| No. | R³ | R⁴ | R⁵ |
|---|---|---|---|
| 1964 | CH₃ | 3-OCF₃—C₆H₄ | i-C₃H₇ |
| 1965 | CH₃ | 3-OCF₃—C₆H₄ | n-C₄H₉ |
| 1966 | CH₃ | 3-OCF₃—C₆H₄ | t-C₄H₉ |
| 1967 | CH₃ | 3-OCF₃—C₆H₄ | n-C₆H₁₃ |
| 1968 | CH₃ | 3-OCF₃—C₆H₄ | Prop-1-en-3-yl |
| 1969 | CH₃ | 3-OCF₃—C₆H₄ | (E)-1-Chloroprop-1-en-3-yl |
| 1970 | CH₃ | 3-OCF₃—C₆H₄ | Propyn-3-yl |
| 1971 | CH₃ | 3-OCF₃—C₆H₄ | 3-Methylbut-2-en-1-yl |
| 1972 | CH₃ | 4-OCF₃—C₆H₄ | H |
| 1973 | CH₃ | 4-OCF₃—C₆H₄ | CH₃ |
| 1974 | CH₃ | 4-OCF₃—C₆H₄ | C₂H₅ |
| 1975 | CH₃ | 4-OCF₃—C₆H₄ | n-C₃H₇ |
| 1976 | CH₃ | 4-OCF₃—C₆H₄ | i-C₃H₇ |
| 1977 | CH₃ | 4-OCF₃—C₆H₄ | n-C₄H₉ |
| 1978 | CH₃ | 4-OCF₃—C₆H₄ | t-C₄H₉ |
| 1979 | CH₃ | 4-OCF₃—C₆H₄ | n-C₆H₁₃ |
| 1980 | CH₃ | 4-OCF₃—C₆H₄ | Prop-1-en-3-yl |
| 1981 | CH₃ | 4-OCF₃—C₆H₄ | (E)-1-Chloroprop-1-en-3-yl |
| 1982 | CH₃ | 4-OCF₃—C₆H₄ | Propyn-3-yl |
| 1983 | CH₃ | 4-OCF₃—C₆H₄ | 3-Methylbut-2-en-1-yl |
| 1984 | CH₃ | 2-SCH₃—C₆H₄ | H |
| 1985 | CH₃ | 2-SCH₃—C₆H₄ | CH₃ |
| 1986 | CH₃ | 2-SCH₃—C₆H₄ | C₂H₅ |
| 1987 | CH₃ | 2-SCH₃—C₆H₄ | n-C₃H₇ |
| 1988 | CH₃ | 2-SCH₃—C₆H₄ | i-C₃H₇ |
| 1989 | CH₃ | 2-SCH₃—C₆H₄ | n-C₄H₉ |
| 1990 | CH₃ | 2-SCH₃—C₆H₄ | t-C₄H₉ |
| 1991 | CH₃ | 2-SCH₃—C₆H₄ | n-C₆H₁₃ |
| 1992 | CH₃ | 2-SCH₃—C₆H₄ | Prop-1-en-3-yl |
| 1993 | CH₃ | 2-SCH₃—C₆H₄ | (E)-1-Chloroprop-1-en-3-yl |
| 1994 | CH₃ | 2-SCH₃—C₆H₄ | Propyn-3-yl |
| 1995 | CH₃ | 2-SCH₃—C₆H₄ | 3-Methylbut-2-en-1-yl |
| 1996 | CH₃ | 3-SCH₃—C₆H₄ | H |
| 1997 | CH₃ | 3-SCH₃—C₆H₄ | CH₃ |
| 1998 | CH₃ | 3-SCH₃—C₆H₄ | C₂H₅ |
| 1999 | CH₃ | 3-SCH₃—C₆H₄ | n-C₃H₇ |
| 2000 | CH₃ | 3-SCH₃—C₆H₄ | i-C₃H₇ |
| 2001 | CH₃ | 3-SCH₃—C₆H₄ | n-C₄H₉ |
| 2002 | CH₃ | 3-SCH₃—C₆H₄ | t-C₄H₉ |
| 2003 | CH₃ | 3-SCH₃—C₆H₄ | n-C₆H₁₃ |
| 2004 | CH₃ | 3-SCH₃—C₆H₄ | Prop-1-en-3-yl |
| 2005 | CH₃ | 3-SCH₃—C₆H₄ | (E)-1-Chloroprop-1-en-3-yl |
| 2006 | CH₃ | 3-SCH₃—C₆H₄ | Propyn-3-yl |
| 2007 | CH₃ | 3-SCH₃—C₆H₄ | 3-Methylbut-2-en-1-yl |
| 2008 | CH₃ | 4-SCH₃—C₆H₄ | H |
| 2009 | CH₃ | 4-SCH₃—C₆H₄ | CH₃ |
| 2010 | CH₃ | 4-SCH₃—C₆H₄ | C₂H₅ |
| 2011 | CH₃ | 4-SCH₃—C₆H₄ | n-C₃H₇ |
| 2012 | CH₃ | 4-SCH₃—C₆H₄ | i-C₃H₇ |
| 2013 | CH₃ | 4-SCH₃—C₆H₄ | n-C₄H₉ |
| 2014 | CH₃ | 4-SCH₃—C₆H₄ | t-C₄H₉ |
| 2015 | CH₃ | 4-SCH₃—C₆H₄ | n-C₆H₁₃ |
| 2016 | CH₃ | 4-SCH₃—C₆H₄ | Prop-1-en-3-yl |
| 2017 | CH₃ | 4-SCH₃—C₆H₄ | (E)-1-Chloroprop-1-en-3-yl |
| 2018 | CH₃ | 4-SCH₃—C₆H₄ | Propyn-3-yl |
| 2019 | CH₃ | 4-SCH₃—C₆H₄ | 3-Methylbut-2-en-1-yl |
| 2020 | CH₃ | 2-Methylsulfonyl-C₆H₄ | H |
| 2021 | CH₃ | 2-Methylsulfonyl-C₆H₄ | CH₃ |
| 2022 | CH₃ | 2-Methylsulfonyl-C₆H₄ | C₂H₅ |
| 2023 | CH₃ | 2-Methylsulfonyl-C₆H₄ | n-C₃H₇ |
| 2024 | CH₃ | 2-Methylsulfonyl-C₆H₄ | i-C₃H₇ |
| 2025 | CH₃ | 2-Methylsulfonyl-C₆H₄ | n-C₄H₉ |
| 2026 | CH₃ | 2-Methylsulfonyl-C₆H₄ | t-C₄H₉ |
| 2027 | CH₃ | 2-Methylsulfonyl-C₆H₄ | n-C₆H₁₃ |
| 2028 | CH₃ | 2-Methylsulfonyl-C₆H₄ | Prop-1-en-3-yl |
| 2029 | CH₃ | 2-Methylsulfonyl-C₆H₄ | (E)-1-Chloroprop-1-en-3-yl |
| 2030 | CH₃ | 2-Methylsulfonyl-C₆H₄ | Propyn-3-yl |
| 2031 | CH₃ | 2-Methylsulfonyl-C₆H₄ | 3-Methylbut-2-en-1-yl |
| 2032 | CH₃ | 3-Methylsulfonyl-C₆H₄ | H |
| 2033 | CH₃ | 3-Methylsulfonyl-C₆H₄ | CH₃ |
| 2034 | CH₃ | 3-Methylsulfonyl-C₆H₄ | C₂H₅ |
| 2035 | CH₃ | 3-Methylsulfonyl-C₆H₄ | n-C₃H₇ |
| 2036 | CH₃ | 3-Methylsulfonyl-C₆H₄ | i-C₃H₇ |
| 2037 | CH₃ | 3-Methylsulfonyl-C₆H₄ | n-C₄H₉ |
| 2038 | CH₃ | 3-Methylsulfonyl-C₆H₄ | t-C₄H₉ |
| 2039 | CH₃ | 3-Methylsulfonyl-C₆H₄ | n-C₆H₁₃ |
| 2040 | CH₃ | 3-Methylsulfonyl-C₆H₄ | Prop-1-en-3-yl |

TABLE A-continued

| No. | R³ | R⁴ | R⁵ |
|---|---|---|---|
| 2041 | CH₃ | 3-Methylsulfonyl-C₆H₄ | (E)-1-Chloroprop-1en-3-yl |
| 2042 | CH₃ | 3-Methylsulfonyl-C₆H₄ | Propyn-3-yl |
| 2043 | CH₃ | 3-Methylsulfonyl-C₆H₄ | 3-Methylbut-2-en-1-yl |
| 2044 | CH₃ | 4-Methylsulfonyl-C₆H₄ | H |
| 2045 | CH₃ | 4-Methylsulfonyl-C₆H₄ | CH₃ |
| 2046 | CH₃ | 4-Methylsulfonyl-C₆H₄ | C₂H₅ |
| 2047 | CH₃ | 4-Methylsulfonyl-C₆H₄ | n-C₃H₇ |
| 2048 | CH₃ | 4-Methylsulfonyl-C₆H₄ | i-C₃H₇ |
| 2049 | CH₃ | 4-Methylsulfonyl-C₆H₄ | n-C₄H₉ |
| 2050 | CH₃ | 4-Methylsulfonyl-C₆H₄ | t-C₄H₉ |
| 2051 | CH₃ | 4-Methylsulfonyl-C₆H₄ | n-C₆H₁₃ |
| 2052 | CH₃ | 4-Methylsulfonyl-C₆H₄ | Prop-1-en-3-yl |
| 2053 | CH₃ | 4-Methylsulfonyl-C₆H₄ | (E)-1-Chloroprop-1-en-3-yl |
| 2054 | CH₃ | 4-Methylsulfonyl-C₆H₄ | Propyn-3-yl |
| 2055 | CH₃ | 4-Methylsulfonyl-C₆H₄ | 3-Methylbut-2-en-1-yl |
| 2056 | CH₃ | 2-Methoxycarbonyl-C₆H₄ | H |
| 2057 | CH₃ | 2-Methoxycarbonyl-C₆H₄ | CH₃ |
| 2058 | CH₃ | 2-Methoxycarbonyl-C₆H₄ | C₂H₅ |
| 2059 | CH₃ | 2-Methoxycarbonyl-C₆H₄ | n-C₃H₇ |
| 2060 | CH₃ | 2-Methoxycarbonyl-C₆H₄ | i-C₃H₇ |
| 2061 | CH₃ | 2-Methoxycarbonyl-C₆H₄ | n-C₄H₉ |
| 2062 | CH₃ | 2-Methoxycarbonyl-C₆H₄ | t-C₄H₉ |
| 2063 | CH₃ | 2-Methoxycarbonyl-C₆H₄ | n-C₆H₁₃ |
| 2064 | CH₃ | 2-Methoxycarbonyl-C₆H₄ | Prop-1-en-3-yl |
| 2065 | CH₃ | 2-Methoxycarbonyl-C₆H₄ | (E)-1-Chloroprop-1-en-3-yl |
| 2966 | CH₃ | 2-Methoxycarbonyl-C₆H₄ | Propyn-3-yl |
| 2067 | CH₃ | 2-Methoxycarbonyl-C₆H₄ | 3-Methylbut-2-en-1-yl |
| 2068 | CH₃ | 3-Methoxycarbonyl-C₆H₄ | H |
| 2069 | CH₃ | 3-Methoxycarbonyl-C₆H₄ | CH₃ |
| 2070 | CH₃ | 3-Methoxycarbonyl-C₆H₄ | C₂H₅ |
| 2071 | CH₃ | 3-Methoxycarbonyl-C₆H₄ | n-C₃H₇ |
| 2072 | CH₃ | 3-Methoxycarbonyl-C₆H₄ | i-C₃H₇ |
| 2073 | CH₃ | 3-Methoxycarbonyl-C₆H₄ | n-C₄H₉ |
| 2074 | CH₃ | 3-Methoxycarbonyl-C₆H₄ | t-C₄H₉ |
| 2075 | CH₃ | 3-Methoxycarbonyl-C₆H₄ | n-C₆H₁₃ |
| 2076 | CH₃ | 3-Methoxycarbonyl-C₆H₄ | Prop-1-en-3-yl |
| 2077 | CH₃ | 3-Methoxycarbonyl-C₆H₄ | (E)-1-Chloroprop-1-en-3-yl |
| 2078 | CH₃ | 3-Methoxycarbonyl-C₆H₄ | Propyn-3-yl |
| 2079 | CH₃ | 3-Methoxycarbonyl-C₆H₄ | 3-Methylbut-2-en-1-yl |
| 2080 | CH₃ | 4-Methoxycarbonyl-C₆H₄ | H |
| 2081 | CH₃ | 4-Methoxycarbonyl-C₆H₄ | CH₃ |
| 2082 | CH₃ | 4-Methoxycarbonyl-C₆H₄ | C₂H₅ |
| 2083 | CH₃ | 4-Methoxycarbonyl-C₆H₄ | n-C₃H₇ |
| 2084 | CH₃ | 4-Methoxycarbonyl-C₆H₄ | i-C₃H₇ |
| 2085 | CH₃ | 4-Methoxycarbonyl-C₆H₄ | n-C₄H₉ |
| 2086 | CH₃ | 4-Methoxycarbbnyl-C₆H₄ | t-C₄H₉ |
| 2087 | CH₃ | 4-Methoxycarbonyl-C₆H₄ | n-C₆H₁₃ |
| 2088 | CH₃ | 4-Methoxycarbonyl-C₆H₄ | Prop-1-en-3-yl |
| 2089 | CH₃ | 4-Methoxycarbonyl-C₆H₄ | (E)-1-Chloroprop-1-en-3-yl |
| 2090 | CH₃ | 4-Methoxycarbonyl-C₆H₄ | Propyn-3-yl |
| 2091 | CH₃ | 4-Methoxycarbonyl-C₆H₄ | 3-Methylbut-2-en-1-yl |
| 2092 | CH₃ | 2-Ethoxycarbonyl-C₆H₄ | H |
| 2093 | CH₃ | 2-Ethoxycarbonyl-C₆H₄ | CH₃ |
| 2094 | CH₃ | 2-Ethoxycarbonyl-C₆H₄ | C₂H₅ |
| 2095 | CH₃ | 2-Ethoxycarbonyl-C₆H₄ | n-C₃H₇ |
| 2096 | CH₃ | 2-Ethoxycarbonyl-C₆H₄ | i-C₃H₇ |
| 2097 | CH₃ | 2-Ethoxycarbonyl-C₆H₄ | n-C₄H₉ |
| 2098 | CH₃ | 2-Ethoxycarbonyl-C₆H₄ | t-C₄H₉ |
| 2099 | CH₃ | 2-Ethoxycarbonyl-C₆H₄ | n-C₆H₁₃ |
| 2100 | CH₃ | 2-Ethoxycarbonyl-C₆H₄ | Prop-1-en-3-yl |
| 2101 | CH₃ | 2-Ethoxycarbonyl-C₆H₄ | (E)-1-Chloroprop-1-en-3-yl |
| 2102 | CH₃ | 2-Ethoxycarbonyl-C₆H₄ | Propyn-3-yl |
| 2103 | CH₃ | 2-Ethoxycarbonyl-C₆H₄ | 3-Methylbut-2-en-1-yl |
| 2104 | CH₃ | 3-Ethoxycarbonyl-C₆H₄ | H |
| 2105 | CH₃ | 3-Ethoxycarbonyl-C₆H₄ | CH₃ |
| 2106 | CH₃ | 3-Ethoxycarbonyl-C₆H₄ | C₂H₅ |
| 2107 | CH₃ | 3-Ethoxycarbonyl-C₆H₄ | n-C₃H₇ |
| 2108 | CH₃ | 3-Ethoxycarbonyl-C₆H₄ | i-C₃H₇ |
| 2109 | CH₃ | 3-Ethoxycarbonyl-C₆H₄ | n-C₄H₉ |
| 2110 | CH₃ | 3-Ethoxycarbonyl-C₆H₄ | t-C₄H₉ |
| 2111 | CH₃ | 3-Ethoxycarbonyl-C₆H₄ | n-C₆H₁₃ |
| 2112 | CH₃ | 3-Ethoxycarbonyl-C₆H₄ | Prop-1-en-3-yl |
| 2113 | CH₃ | 3-Ethoxycarbonyl-C₆H₄ | (E)-1-Chloroprop-1-en-3-yl |
| 2114 | CH₃ | 3-Ethoxycarbonyl-C₆H₄ | Propyn-3-yl |
| 2115 | CH₃ | 3-Ethoxycarbonyl-C₆H₄ | 3-Methylbut-2-en-1-yl |
| 2116 | CH₃ | 4-Ethoxycarbonyl-C₆H₄ | H |
| 2117 | CH₃ | 4-Ethoxycarbonyl-C₆H₄ | CH₃ |

TABLE A-continued

| No. | R³ | R⁴ | R⁵ |
|---|---|---|---|
| 2118 | CH₃ | 4-Ethoxycarbonyl-C₆H₄ | C₂H₅ |
| 2119 | CH₃ | 4-Ethoxycarbonyl-C₆H₄ | n-C₃H₇ |
| 2120 | CH₃ | 4-Ethoxycarbonyl-C₆H₄ | i-C₃H₇ |
| 2121 | CH₃ | 4-Ethoxycarbonyl-C₆H₄ | n-C₄H₉ |
| 2122 | CH₃ | 4-Ethoxycarbonyl-C₆H₄ | t-C₄H₉ |
| 2123 | CH₃ | 4-Ethoxycarbonyl-C₆H₄ | n-C₆H₁₃ |
| 2124 | CH₃ | 4-Ethoxycarbonyl-C₆H₄ | Prpp-1-en-3-yl |
| 2125 | CH₃ | 4-Ethoxycarbonyl-C₆H₄ | (E)-1-Chloroprop-1-en-3-yl |
| 2126 | CH₃ | 4-Ethoxycarbonyl-C₆H₄ | Propyn-3-yl |
| 2127 | CH₃ | 4-Ethoxycarbonyl-C₆H₄ | 3-Methylbut-2-en-1-yl |
| 2128 | CH₃ | 2-Aminocarbonyl-C₆H₄ | H |
| 2129 | CH₃ | 2 Aminocarbonyl-C₆H₄ | CH₃ |
| 2130 | CH₃ | 2-Aminocarbonyl-C₅H₄ | C₂H₅ |
| 2131 | CH₃ | 2 Aminocarbonyl-C₆H₄ | n-C₃H₇ |
| 2132 | CH₃ | 2 Aminocarbonyl-C₆H₄ | i-C₃H₇ |
| 2133 | CH₃ | 2-Aminocarbonyl-C₆H₄ | n-C₄H₉ |
| 2134 | CH₃ | 2-Aminocarbonyl-C₆H₄ | t-C₄H₉ |
| 2135 | CH₃ | 2-Aminocarbonyl-C₆H₄ | n-C₆H₁₃ |
| 2136 | CH₃ | 2-Aminocarbonyl-C₆H₄ | Prop-1-en-3-yl |
| 2137 | CH₃ | 2-Aminocarbonyl-C₆H₄ | (E)-1-Chloroprop-1-en-3-yl |
| 2138 | CH₃ | 2-Aminocarbonyl-C₆H₄ | Propyn-3-yl |
| 2139 | CH₃ | 2-Aminocarbonyl-C₆H₄ | 3-Methylbut-2-en-1-yl |
| 2140 | CH₃ | 3-Aminocarbonyl-C₆H₄ | H |
| 2141 | CH₃ | 3-Aminocarbonyl-C₆H₄ | CH₃ |
| 2142 | CH₃ | 3-Aminocarbonyl-C₆H₄ | C₂H₅ |
| 2143 | CH₃ | 3-Aminocarbonyl-C₆H₄ | n-C₃H₇ |
| 2144 | CH₃ | 3-Aminocarbonyl-C₆H₄ | i-C₃H₇ |
| 2145 | CH₃ | 3-Aminocarbonyl-C₆H₄ | n-C₄H₉ |
| 2146 | CH₃ | 3-Aminocarbonyl-C₆H₄ | t-C₄H₉ |
| 2147 | CH₃ | 3-Aminocarbonyl-C₆H₄ | n-C₆H₁₃ |
| 2148 | CH₃ | 3-Aminocarbonyl-C₆H₄ | Prop-1-en-3-yl |
| 2149 | CH₃ | 3-Aminocarbonyl-C₆H₄ | (E)-1-Chloroprop-1-en-3-yl |
| 2150 | CH₃ | 3-Aminocarbonyl-C₆H₄ | Propyn-3-yl |
| 2151 | CH₃ | 3-Aminocarbonyl-C₆H₄ | 3-Methylbut-2-en-1-yl |
| 2152 | CH₃ | 4-Aminocarbonyl-C₆H₄ | H |
| 2153 | CH₃ | 4-Aminocarbonyl-C₆H₄ | CH₃ |
| 2154 | CH₃ | 4-Aminocarbonyl-C₆H₄ | C₂H₅ |
| 2155 | CH₃ | 4-Aminocarbonyl-C₆H₄ | n-C₃H₇ |
| 2156 | CH₃ | 4-Aminocarbonyl-C₆H₄ | i-C₃H₇ |
| 2157 | CH₃ | 4-Aminocarbonyl-C₆H₄ | n-C₄H₉ |
| 2158 | CH₃ | 4-Aminocarbonyl-C₆H₄ | t-C₄H₉ |
| 2159 | CH₃ | 4-Aminocarbonyl-C₆H₄ | n-C₆H₁₃ |
| 2160 | CH₃ | 4-Aminocarbonyl-C₆H₄ | Prop-1-en-3-yl |
| 2161 | CH₃ | 4-Aminocarbonyl-C₆H₄ | (E)-1-Chloroprop-1-en-3-yl |
| 2162 | CH₃ | 4-Aminocarbonyl-C₆H₄ | Propyn-3-yl |
| 2163 | CH₃ | 4-Aminocarbonyl-C₆H₄ | 3-Methylbut-2-en-1-yl |
| 2164 | CH₃ | 2-(N-Methylaminocarbonyl)-C₆H₄ | H |
| 2165 | CH₃ | 2-(N-Methylaminocarbonyl)-C₆H₄ | CH₃ |
| 2166 | CH₃ | 2-(N-Methylaminocarbonyl)-C₆H₄ | C₂H₅ |
| 2167 | CH₃ | 2-(N-Methylaminocarbonyl)-C₆H₄ | n-C₃H₇ |
| 2168 | CH₃ | 2-(N-Methylaminocarbonyl)-C₆H₄ | i-C₃H₇ |
| 2169 | CH₃ | 2-(N-Methylaminocarbonyl)-C₆H₄ | n-C₄H₉ |
| 2170 | CH₃ | 2-(N-Methylaminocarbonyl)-C₆H₄ | t-C₄H₉ |
| 2171 | CH₃ | 2-(N-Methylaminocarbonyl)-C₆H₄ | n-C₆H₁₃ |
| 2172 | CH₃ | 2-(N-Methylaminocarbonyl)-C₆H₄ | Prop-1-en-3-yl |
| 2173 | CH₃ | 2-(N-Methylaminocarbonyl)-C₆H₄ | (E)-1-Chloroprop-1-en-3-yl |
| 2174 | CH₃ | 2-(N-Methylaminocarbonyl)-C₆H₄ | Propyn-3-yl |
| 2175 | CH₃ | 2-(N-Methylaminocarbonyl)-C₆H₄ | 3-Methylbut-2-en-1-yl |
| 2176 | CH₃ | 3-(N-Methylaminocarbonyl)-C₆H₄ | H |
| 2177 | CH₃ | 3-(N-Methylaminocarbonyl)-C₆H₄ | CH₃ |
| 2178 | CH₃ | 3-(N-Methylaminocarbonyl)-C₆H₄ | C₂H₅ |
| 2179 | CH₃ | 3-(N-Methylaminocarbonyl)-C₆H₄ | n-C₃H₇ |
| 2180 | CH₃ | 3-(N-Methylaminocarbonyl)-C₆H₄ | i-C₃H₇ |
| 2181 | CH₃ | 3-(N-Methylaminocarbonyl)-C₆H₄ | n-C₄H₉ |
| 2182 | CH₃ | 3-(N-Methylaminocarbonyl)-C₆H₄ | t-C₄H₉ |
| 2183 | CH₃ | 3-(N-Methylaminocarbonyl)-C₆H₄ | n-C₆H₁₃ |
| 2184 | CH₃ | 3-(N-Methylaminocarbonyl)-C₆H₄ | Prop-1-en-3-yl |
| 2185 | CH₃ | 3-(N-Methylaminocarbonyl)-C₆H₄ | (E)-1-Chloroprop-1-en-3-yl |
| 2186 | CH₃ | 3-(N-Methylaminocarbonyl)-C₆H₄ | Propyn-3-yl |
| 2187 | CH₃ | 3-(N-Methylaminocarbonyl)-C₆H₄ | 3-Methylbut-2-en-1-yl |
| 2188 | CH₃ | 4-(N-Methylaminocarbonyl)-C₆H₄ | H |
| 2189 | CH₃ | 4-(N-Methylaminocarbonyl)-C₆H₄ | CH₃ |
| 2190 | CH₃ | 4-(N-Methylaminocarbonyl)-C₆H₄ | C₂H₅ |
| 2191 | CH₃ | 4-(N-Methylaminocarbonyl)-C₆H₄ | n-C₃H₇ |
| 2192 | CH₃ | 4-(N-Methylaminocarbonyl)-C₆H₄ | i-C₃H₇ |
| 2193 | CH₃ | 4-(N-Methylaminocarbonyl)-C₆H₄ | n-C₄H₉ |
| 2194 | CH₃ | 4-(N-Methylaminocarbonyl)-C₆H₄ | t-C₄H₉ |

TABLE A-continued

| No. | R³ | R⁴ | R⁵ |
|---|---|---|---|
| 2195 | CH₃ | 4-(N-Methylaminocarbonyl)-C₆H₄ | n-C₆H₁₃ |
| 2196 | CH₃ | 4-(N-Methylaminocarbonyl)-C₆H₄ | Prop-1-en-3-yl |
| 2197 | CH₃ | 4-(N-Methylaminocarbonyl)-C₆H₄ | (E)-1-Chloroprop-1-en-3-yl |
| 2198 | CH₃ | 4-(N-Methylaminocarbonyl)-C₆H₄ | Propyn-3-yl |
| 2199 | CH₃ | 4-(N-Methylaminocarbonyl)-C₆H₄ | 3-Methylbut-2-en-1-yl |
| 2200 | CH₃ | 2-Dimethylaminocarbonyl-C₆H₄ | H |
| 2201 | CH₃ | 2-Dimethylaminocarbonyl-C₆H₄ | CH₃ |
| 2202 | CH₃ | 2-Dimethylaminocarbonyl-C₆H₄ | C₂H₅ |
| 2203 | CH₃ | 2-Dimethylaminocarbonyl-C₆H₄ | n-C₃H₇ |
| 2204 | CH₃ | 2-Dimethylaminocarbonyl-C₆H₄ | i-C₃H₇ |
| 2205 | CH₃ | 2-Dimethylaminocarbonyl-C₆H₄ | n-C₄H₉ |
| 2206 | CH₃ | 2-Dimethylaminocarbonyl-C₆H₄ | t-C₄H₉ |
| 2207 | CH₃ | 2-Dimethylaminocarbonyl-C₆H₄ | n-C₆H₁₃ |
| 2208 | CH₃ | 2-Dimethylaminocarbonyl-C₆H₄ | Prop-1-en-3-yl |
| 2209 | CH₃ | 2-Dimethylaminocarbonyl-C₆H₄ | (E)-1-Chloroprop-1-en-3-yl |
| 2210 | CH₃ | 2-Dimethylaminocarbonyl-C₆H₄ | Propyn-3-yl |
| 2211 | CH₃ | 2-Dimethylaminocarbonyl-C₆H₄ | 3-Methylbut-2-en-1-yl |
| 2212 | CH₃ | 3-Dimethylaminocarbonyl-C₆H₄ | H |
| 2213 | CH₃ | 3-Dimethylaminocarbonyl-C₆H₄ | CH₃ |
| 2214 | CH₃ | 3-Dimethylaminocarbonyl-C₆H₄ | C₂H₅ |
| 2215 | CH₃ | 3-Dimethylaminocarbonyl-C₆H₄ | n-C₃H₇ |
| 2216 | CH₃ | 3-Dimethylaminocarbonyl-C₆H₄ | i-C₃H₇ |
| 2217 | CH₃ | 3-Dimethylaminocarbonyl-C₆H₄ | n-C₄H₉ |
| 2218 | CH₃ | 3-Dimethylaminocarbonyl-C₆H₄ | t-C₄H₉ |
| 2219 | CH₃ | 3-Dimethylaminocarbonyl-C₆H₄ | n-C₆H₁₃ |
| 2220 | CH₃ | 3-Dimethylaminocarbonyl-C₆H₄ | Prop-1-en-3-yl |
| 2221 | CH₃ | 3-Dimethylaminocarbonyl-C₆H₄ | (E)-1-Chloroprop-1-en-3-yl |
| 2222 | CH₃ | 3-Dimethylaminocarbonyl-C₆H₄ | Propyn-3-yl |
| 2223 | CH₃ | 3-Dimethylaminocarbonyl-C₆H₄ | 3-Methylbut-2-en-1-yl |
| 2224 | CH₃ | 4-Dimethylaminocarbonyl-C₆H₄ | H |
| 2225 | CH₃ | 4-Dimethylaminocarbonyl-C₆H₄ | CH₃ |
| 2226 | CH₃ | 4-Dimethylaminocarbonyl-C₆H₄ | C₂H₅ |
| 2227 | CH₃ | 4-Dimethylaminocarbonyl-C₆H₄ | n-C₃H₇ |
| 2228 | CH₃ | 4-Dimethylaminocarbonyl-C₆H₄ | i-C₃H₇ |
| 2229 | CH₃ | 4-Dimethylaminocarbonyl-C₆H₄ | n-C₄H₉ |
| 2230 | CH₃ | 4-Dimethylaminocarbonyl-C₆H₄ | t-C₄H₉ |
| 2231 | CH₃ | 4-Dimethylaminocarbonyl-C₆H₄ | n-C₆H₁₃ |
| 2232 | CH₃ | 4-Dimethylaminocarbonyl-C₆H₄ | Prop-1-en-3-yl |
| 2233 | CH₃ | 4-Dimethylaminocarbonyl-C₆H₄ | (E)-1-Chloroprop-1-en-3-yl |
| 2234 | CH₃ | 4-Dimethylaminocarbonyl-C₆H₄ | Propyn-3-yl |
| 2235 | CH₃ | 4-Dimethylaminocarbonyl-C₆H₄ | 3-Methylbut-2-en-1-yl |
| 2236 | CH₃ | C₂H₅ | H |
| 2237 | CH₃ | C₂H₅ | CH₃ |
| 2238 | CH₃ | C₂H₅ | C₂H₅ |
| 2239 | CH₃ | C₂H₅ | n-C₃H₇ |
| 2240 | CH₃ | C₂H₅ | i-C₃H₇ |
| 2241 | CH₃ | C₂H₅ | Cyclopropyl |
| 2242 | CH₃ | C₂H₅ | n-C₄H₉ |
| 2243 | CH₃ | C₂H₅ | t-C₄H₉ |
| 2244 | CH₃ | C₂H₅ | n-C₆H₁₃ |
| 2245 | CH₃ | C₂H₅ | (E)-1-Chloropropen-3-yl |
| 2246 | CH₃ | C₂H₅ | Propyn-3-yl |
| 2247 | CH₃ | C₂H₅ | 3-Methylbut-2-en-1-yl |
| 2248 | CH₃ | C₂H₅ | 2-Naphthyl-CH₂ |
| 2249 | CH₃ | C₂H₅ | 4-Cl—C₆H₄—CH₂ |
| 2250 | CH₃ | C₂H₅ | (E)-4-(4'-Chlorophenyl)but-2-en-1-yl |
| 2251 | CH₃ | C₂H₅ | 6-(4'-Chlorophenyl)hex-1-yl |
| 2252 | CH₃ | C₂H₅ | 3-CF₃—C₆H₄ |
| 2253 | CH₃ | n-C₃H₇ | H |
| 2254 | CH₃ | n-C₃H₇ | CH₃ |
| 2255 | CH₃ | n-C₃H₇ | C₂H₅ |
| 2256 | CH₃ | n-C₃H₇ | n-C₃H₇ |
| 2257 | CH₃ | n-C₃H₇ | i-C₃H₇ |
| 2258 | CH₃ | n-C₃H₇ | Cyclopropyl |
| 2259 | CH₃ | n-C₃H₇ | n-C₄H₉ |
| 2260 | CH₃ | n-C₃H₇ | t-C₄H₉ |
| 2261 | CH₃ | n-C₃H₇ | n-C₆H₁₃ |
| 2262 | CH₃ | n-C₃H₇ | (E)-1-Chloropropen-3-yl |
| 2263 | CH₃ | n-C₃H₇ | Propyn-3-yl |
| 2264 | CH₃ | n-C₃H₇ | 3-Methylbut-2-en-1-yl |
| 2265 | CH₃ | n-C₃H₇ | 2-Naphthyl-CH₂ |
| 2266 | CH₃ | n-C₃H₇ | 4-Cl—C₆H₄—CH₂ |
| 2267 | CH₃ | n-C₃H₇ | (E)-4-(4'-Chlorophenyl)but-2-en-1-yl |
| 2268 | CH₃ | n-C₃H₇ | 6-(4'-Chlorophenyl)hex-1-yl |
| 2269 | CH₃ | n-C₃H₇ | 3-CF₃—C₆H₄ |
| 2270 | CH₃ | i-C₃H₇ | H |
| 2271 | CH₃ | i-C₃H₇ | CH₃ |

TABLE A-continued

| No. | R³ | R⁴ | R⁵ |
|---|---|---|---|
| 2272 | CH₃ | i-C₃H₇ | C₂H₅ |
| 2273 | CH₃ | i-C₃H₇ | n-C₃H₇ |
| 2274 | CH₃ | i-C₃H₇ | i-C₃H₇ |
| 2275 | CH₃ | i-C₃H₇ | Cyclopropyl |
| 2276 | CH₃ | i-C₃H₇ | n-C₄H₉ |
| 2277 | CH₃ | i-C₃H₇ | t-C₄H₉ |
| 2278 | CH₃ | i-C₃H₇ | n-C₆H₁₃ |
| 2279 | CH₃ | i-C₃H₇ | (E)-1-Chloropropen-3-yl |
| 2280 | CH₃ | i-C₃H₇ | Propyn-3-yl |
| 2281 | CH₃ | i-C₃H₇ | 3-Methylbut-2-en-1-yl |
| 2282 | CH₃ | i-C₃H₇ | 2 Naphthyl-CH₂ |
| 2283 | CH₃ | i-C₃H₇ | 4-Cl—C₆H₄—CH₂ |
| 2284 | CH₃ | i-C₃H₇ | (E)-4-(4'-Chlorophenyl)but-2-en-1-yl |
| 2285 | CH₃ | i-C₃H₇ | 6-(4'-Chlorophenyl)hex-1-yl |
| 2286 | CH₃ | i-C₃H₇ | 3-CF₃—C₆H₄ |
| 2287 | CH₃ | n-C₄H₉ | H |
| 2288 | CH₃ | n-C₄H₉ | CH₃ |
| 2289 | CH₃ | n-C₄H₉ | C₂H₅ |
| 2290 | CH₃ | n-C₄H₉ | n-C₃H₇ |
| 2291 | CH₃ | n-C₄H₉ | i-C₃H₇ |
| 2292 | CH₃ | n-C₄H₉ | Cyclopropyl |
| 2293 | CH₃ | n-C₄H₉ | n-C₄H₉ |
| 2294 | CH₃ | n-C₄H₉ | t-C₄H₉ |
| 2295 | CH₃ | n-C₄H₉ | n-C₆H₁₃ |
| 2296 | CH₃ | n-C₄H₉ | (E)1-Chloropropen-3-yl |
| 2297 | CH₃ | n-C₄H₉ | Propyn-3-yl |
| 2298 | CH₃ | n-C₄H₉ | 3-Methylbut-2-en-1-yl |
| 2299 | CH₃ | n-C₄H₉ | 2-Naphthyl-CH₂ |
| 2300 | CH₃ | n-C₄H₉ | 4-Cl—C₆H₄—CH₂ |
| 2301 | CH₃ | n-C₄H₉ | (E)-4-(4'-Chlorophenyl)but-2-en-1-yl |
| 2302 | CH₃ | n-C₄H₉ | 6-(4'-Chlorophenyl)hex-1-yl |
| 2303 | CH₃ | n-C₄H₉ | 3-CF₃—C₆H₄ |
| 2304 | CH₃ | CH₃—CH(CH₃)—CH₂ | H |
| 2305 | CH₃ | CH₃—CH(CH₃)—CH₂ | CH₃ |
| 2306 | CH₃ | CH₃—CH(CH₃)—CH₂ | C₂H₅ |
| 2307 | CH₃ | CH₃—CH(CH₃)—CH₂ | n-C₃H₇ |
| 2308 | CH₃ | CH₃—CH(CH₃)—CH₂ | i-C₃H₇ |
| 2309 | CH₃ | CH₃—CH(CH₃)—CH₂ | Cyclopropyl |
| 2310 | CH₃ | CH₃—CH(CH₃)—CH₂ | n-C₄H₉ |
| 2311 | CH₃ | CH₃—CH(CH₃)—CH₂ | t-C₄H₉ |
| 2312 | CH₃ | CH₃—CH(CH₃)—CH₂ | n-C₆H₁₃ |
| 2313 | CH₃ | CH₃—CH(CH₃)—CH₂ | (E)-1-Chloropropen-3-yl |
| 2314 | CH₃ | CH₃—CH(CH₃)—CH₂ | Propyn-3-yl |
| 2315 | CH₃ | CH₃—CH(CH₃)—CH₂ | 3-Methylbut-2-en-1-yl |
| 2316 | CH₃ | CH₃—CH(CH₃)—CH₂ | 2-Naphthyl-CH₂ |
| 2317 | CH₃ | CH₃—CH(CH₃)—CH₂ | 4-Cl—C₆H₄—CH₂ |
| 2318 | CH₃ | CH₃—CH(CH₃)—CH₂ | (E)-4-(4'-Chlorophenyl)but-2-en-1-yl |
| 2319 | CH₃ | CH₃—CH(CH₃)—CH₂ | 6-(4'-Chlorophenyl)hex-1-yl |
| 2320 | CH₃ | CH₃—CH(CH₃)—CH₂ | 3-CF₃—C₆H₄ |
| 2321 | CH₃ | CH₃—CH₂—CH(CH₃) | H |
| 2322 | CH₃ | CH₃—CH₂—CH(CH₃) | CH₃ |
| 2323 | CH₃ | CH₃—CH₂—CH(CH₃) | C₂H₅ |
| 2324 | CH₃ | CH₃—CH₂—CH(CH₃) | n-C₃H₇ |
| 2325 | CH₃ | CH₃—CH₂—CH(CH₃) | i-C₃H₇ |
| 2326 | CH₃ | CH₃—CH₂—CH(CH₃) | Cyclopropyl |
| 2327 | CH₃ | CH₃—CH₂—CH(CH₃) | n-C₄H₉ |
| 2328 | CH₃ | CH₃—CH₂—CH(CH₃) | t-C₄H₉ |
| 2329 | CH₃ | CH₃—CH₂—CH(CH₃) | n-C₆H₁₃ |
| 2330 | CH₃ | CH₃—CH₂—CH(CH₃) | (E)-1-Chloropropen-3-yl |
| 2331 | CH₃ | CH₃—CH₂—CH(CH₃) | Propyn-3-yl |
| 2332 | CH₃ | CH₃—CH₂—CH(CH₃) | 3-Methylbut-2-en-1-yl |
| 2333 | CH₃ | CH₃—CH₂—CH(CH₃) | 2-Naphthyl-CH₂ |
| 2334 | CH₃ | CH₃—CH₂—CH(CH₃) | 4-Cl—C₆H₄—CH₂ |
| 2335 | CH₃ | CH₃—CH₂—CH(CH₃) | (E)-4-(41-Chlorophenyl)but-2-en-1-yl |
| 2336 | CH₃ | CH₃—CH₂—CH(CH₃) | 6-(4'-Chlorophenyl)hex-1-yl |
| 2337 | CH₃ | CH₃—CH₂—CH(CH₃) | 3-CF₃—C₆H₄ |
| 2338 | CH₃ | CF₃ | H |
| 2339 | CH₃ | CF₃ | CH₃ |
| 2340 | CH₃ | CF₃ | C₂H₅ |
| 2341 | CH₃ | CF₃ | n-C₃H₇ |
| 2342 | CH₃ | CF₃ | i-C₃H₇ |
| 2343 | CH₃ | CF₃ | Cyclopropyl |
| 2344 | CH₃ | CF₃ | n-C₄H₉ |
| 2345 | CH₃ | CF₃ | t-C₄H₉ |
| 2346 | CH₃ | CF₃ | n-C₆H₁₃ |
| 2347 | CH₃ | CF₃ | (E)-1-Chloropropen-3-yl |
| 2349 | CH₃ | CF₃ | Propyn-3-yl |

TABLE A-continued

| No. | R³ | R⁴ | R⁵ |
|---|---|---|---|
| 2349 | CH₃ | CF₃ | 3-Methylbut-2-en-1-yl |
| 2350 | CH₃ | CF₃ | 2-Naphthyl-CH₂ |
| 2351 | CH₃ | CF₃ | 4-Cl—C₆H₄—CH₂ |
| 2352 | CH₃ | CF₃ | (E)-4-(4'-Chlorophenyl)but-2-en-1-yl |
| 2353 | CH₃ | CF₃ | 6-(4'-Chlorophenyl)hex-1-yl |
| 2354 | CH₃ | CF₃ | 3-CF₃—C₆H₄ |
| 2355 | CH₃ | N-Pyrrolyl | H |
| 2356 | CH₃ | N-Pyrrolyl | CH₃ |
| 2357 | CH₃ | N-Pyrrolyl | C₂H₅ |
| 2358 | CH₃ | N-Pyrrolyl | n-C₃H₇ |
| 2359 | CH₃ | N-Pyrrolyl | i-C₃H₇ |
| 2360 | CH₃ | N-Pyrazolyl | H |
| 2361 | CH₃ | N-Pyrazolyl | CH₃ |
| 2362 | CH₃ | N-Pyrazolyl | C₂H₅ |
| 2363 | CH₃ | N-Pyrazolyl | n-C₃H₇ |
| 2364 | CH₃ | N-Pyrazolyl | i-C₃H₇ |
| 2365 | CH₃ | N-Imidazolyl | H |
| 2366 | CH₃ | N-Imidazolyl | CH₃ |
| 2367 | CH₃ | N-Imidazolyl | C₂H₅ |
| 2368 | CH₃ | N-Imidazolyl | n-C₃H₇ |
| 2369 | CH₃ | N-Imidazolyl | i-C₃H₇ |
| 2370 | CH₃ | (N-1)-1,2,4-Triazolyl | H |
| 2371 | CH₃ | (N-1)-1,2,4-Triazolyl | CH₃ |
| 2372 | CH₃ | (N-1)-1,2,4-Triazolyl | C₂H₅ |
| 2373 | CH₃ | (N-1)-1,2,4-Triazolyl | n-C₃H₇ |
| 2374 | CH₃ | (N-1)-1,2,4-Triazolyl | i-C₃H₇ |
| 2375 | CH₃ | N-Indolyl | H |
| 2376 | CH₃ | N-Indolyl | CH₃ |
| 2377 | CH₃ | N-Indolyl | C₂H₅ |
| 2378 | CH₃ | N-Indolyl | n-C₃H₇ |
| 2379 | CH₃ | N-Indolyl | i-C₃H₇ |
| 2380 | CH₃ | N-Morpholinyl | H |
| 2381 | CH₃ | N-Morpholinyl | CH₃ |
| 2382 | CH₃ | N-Morpholinyl | C₂H₅ |
| 2383 | CH₃ | N-Morpholinyl | n-C₃H₇ |
| 2384 | CH₃ | N-Morpholinyl | i-C₃H₇ |
| 2385 | CH₃ | N-(2,6-Dimethyl)morpholinyl | H |
| 2386 | CH₃ | N-(2,6-Dimethyl)morpholinyl | CH₃ |
| 2387 | CH₃ | N-(2,6-Dimethyl)morpholinyl | C₂H₅ |
| 2388 | CH₃ | N-(2,6-Dimethyl)morpholinyl | n-C₃H₇ |
| 2389 | CH₃ | N-(2,6-Dimethyl)morpholinyl | i-C₃H₇ |
| 2390 | CH₃ | N-Pyrrolidinyl | H |
| 2391 | CH₃ | N-Pyrrolidinyl | CH₃ |
| 2392 | CH₃ | N-Pyrrolidinyl | C₂H₅ |
| 2393 | CH₃ | N-Pyrrolidinyl | n-C₃H₇ |
| 2394 | CH₃ | N-Pyrrolidinyl | i-C₃H₇ |
| 2395 | CH₃ | N-Pyridinyl | H |
| 2396 | CH₃ | N-Pyridinyl | CH₃ |
| 2397 | CH₃ | N-Pyridinyl | C₂H₅ |
| 2398 | CH₃ | N-Pyridinyl | n-C₃H₇ |
| 2399 | CH₃ | N-Pyridinyl | i-C₃H₇ |
| 2400 | CH₃ | n-Piperazinyl | H |
| 2401 | CH₃ | n-Piperazinyl | CH₃ |
| 2402 | CH₃ | n-Piperazinyl | C₂H₅ |
| 2403 | CH₃ | n-Piperazinyl | n-C₃H₇ |
| 2404 | CH₃ | n-Piperazinyl | i-C₃H₇ |
| 2405 | CH₃ | OCH₃ | n-C₄H₉ |
| 2406 | CH₃ | OCH₃ | t-C₄H₉ |
| 2407 | CH₃ | OCH₃ | n-C₆H₁₃ |
| 2408 | CH₃ | OCH₃ | Prop-1-en-3-yl |
| 2409 | CH₃ | OCH₃ | (E)-1-Chloroprop-1-en-3-yl |
| 2410 | CH₃ | OCH₃ | Propyn-3-yl |
| 2411 | CH₃ | OCH₃ | 3-Methylbut-2-en-1-yl |
| 2412 | CH₃ | OC₂H₅ | H |
| 2413 | CH₃ | OC₂H₅ | CH₃ |
| 2414 | CH₃ | OC₂H₅ | C₂H₅ |
| 2415 | CH₃ | OC₂H₅ | n-C₃H₇ |
| 2416 | CH₃ | OC₂H₅ | i-C₃H₇ |
| 2417 | CH₃ | OC₂H₅ | n-C₄H₉ |
| 2418 | CH₃ | OC₂H₅ | t-C₄H₉ |
| 2419 | CH₃ | OC₂H₅ | n-C₆H₁₃ |
| 2420 | CH₃ | OC₂H₅ | Prop-1-en-3-yl |
| 2421 | CH₃ | OC₂H₅ | (E)-1-Chloroprop-1-en-3-yl |
| 2422 | CH₃ | OC₂H₅ | Propyn-3-yl |
| 2423 | CH₃ | OC₂H₅ | 3-Methylbut-2-en-1-yl |
| 2424 | CH₃ | O-n-C₃H₇ | H |
| 2425 | CH₃ | O-n-C₃H₇ | CH₃ |

TABLE A-continued

| No. | R³ | R⁴ | R⁵ |
|---|---|---|---|
| 2426 | CH₃ | O-n-C₃H₇ | C₂H₅ |
| 2427 | CH₃ | O-n-C₃H₇ | n-C₃H₇ |
| 2428 | CH₃ | O-n-C₃H₇ | i-C₃H₇ |
| 2429 | CH₃ | O-n-C₃H₇ | n-C₄H₉ |
| 2430 | CH₃ | O-n-C₃H₇ | t-C₄H₉ |
| 2431 | CH₃ | O-n-C₃H₇ | n-C₆H₁₃ |
| 2432 | CH₃ | O-n-C₃H₇ | Prop-1-en-3-yl |
| 2433 | CH₃ | O-n-C₃H₇ | (E)-1-Chloroprop-1-en-3-yl |
| 2434 | CH₃ | O-n-C₃H₇ | Propyn-3-yl |
| 2435 | CH₃ | O-n-C₃H₇ | 3-Methylbut-2-en-1-yl |
| 2436 | CH₃ | O-i-C₃H₇ | H |
| 2437 | CH₃ | O-i-C₃H₇ | CH₃ |
| 2438 | CH₃ | O-i-C₃H₇ | C₂H₅ |
| 2439 | CH₃ | O-i-C₃H₇ | n-C₃H₇ |
| 2440 | CH₃ | O-i-C₃H₇ | i-C₃H₇ |
| 2441 | CH₃ | O-i-C₃H₇ | n-C₄H₉ |
| 2442 | CH₃ | O-i-C₃H₇ | t-C₄H₉ |
| 2443 | CH₃ | O-i-C₃H₇ | n-C₆H₁₃ |
| 2444 | CH₃ | O-i-C₃H₇ | Prop-1-en-3-yl |
| 2445 | CH₃ | O-i-C₃H₇ | (E)-1-Chloroprop-1-en-3-yl |
| 2446 | CH₃ | O-i-C₃H₇ | Propyn-3-yl |
| 2447 | CH₃ | O-i-C₃H₇ | 3-Methylbut-2-en-1-yl |
| 2448 | CH₃ | O-n-C₄H₉ | H |
| 2449 | CH₃ | O-n-C₄H₉ | CH₃ |
| 2450 | CH₃ | O-n-C₄H₉ | C₂H₅ |
| 2451 | CH₃ | O-n-C₄H₉ | n-C₃H₇ |
| 2452 | CH₃ | O-n-C₄H₉ | i-C₃H₇ |
| 2453 | CH₃ | O-n-C₄H₉ | n-C₄H₉ |
| 2454 | CH₃ | O-n-C₄H₉ | t-C₄H₉ |
| 2455 | CH₃ | O-n-C₄H₉ | n-C₆H₁₃ |
| 2456 | CH₃ | O-n-C₄H₉ | Prop-1-en-3-yl |
| 2457 | CH₃ | O-n-C₄H₉ | (E)-1-Chloroprop-1-en-3-yl |
| 2458 | CH₃ | O-n-C₄H₉ | Propyn-3-yl |
| 2459 | CH₃ | O-n-C₄H₉ | 3-MethylbMt-2-en-1-yl |
| 2460 | CH₃ | O-i-C₄H₉ | H |
| 2461 | CH₃ | O-i-C₄H₉ | CH₃ |
| 2462 | CH₃ | O-i-C₄H₉ | C₂H₅ |
| 2463 | CH₃ | O-i-C₄H₉ | n-C₃H₇ |
| 2464 | CH₃ | O-i-C₄H₉ | i-C₃H₇ |
| 2465 | CH₃ | O-i-C₄H₉ | n-C₄H₉ |
| 2466 | CH₃ | O-i-C₄H₉ | t-C₄H₉ |
| 2467 | CH₃ | O-i-C₄H₉ | n-C₆H₁₃ |
| 2468 | CH₃ | O-i-C₄H₉ | Prop-1-en-3-yl |
| 2469 | CH₃ | O-i-C₄H₉ | (E)-1-Chloroprop-1-en-3-yl |
| 2470 | CH₃ | O-i-C₄H₉ | Propyn-3-yl |
| 2471 | CH₃ | O-i-C₄H₉ | 3-Methylbut-2-en-1-yl |
| 2472 | CH₃ | O-s-C₄H₉ | H |
| 2473 | CH₃ | O-s-C₄H₉ | CH₃ |
| 2474 | CH₃ | O-s-C₄H₉ | C₂H₅ |
| 2475 | CH₃ | O-s-C₄H₉ | n-C₃H₇ |
| 2476 | CH₃ | O-s-C₄H₉ | i-C₃H₇ |
| 2477 | CH₃ | O-s-C₄H₉ | n-C₄H₉ |
| 2478 | CH₃ | O-s-C₄H₉ | t-C₄H₉ |
| 2479 | CH₃ | O-s-C₄H₉ | n-C₆H₁₃ |
| 2480 | CH₃ | O-s-C₄H₉ | Prop-1-en-3-yl |
| 2481 | CH₃ | O-s-C₄H₉ | (E)-1-Chloroprop-1-en-3-yl |
| 2482 | CH₃ | O-s-C₄H₉ | Propyn-3-yl |
| 2483 | CH₃ | O-s-C₄H₉ | 3-Methylbut-2-en-1-yl |
| 2484 | CH₃ | O-t-C₄H₉ | H |
| 2485 | CH₃ | O-t-C₄H₉ | CH₃ |
| 2486 | CH₃ | O-t-C₄H₉ | C₂H₅ |
| 2487 | CH₃ | O-t-C₄H₉ | n-C₃H₇ |
| 2488 | CH₃ | O-t-C₄H₉ | i-C₃H₇ |
| 2489 | CH₃ | O-t-C₄H₉ | n-C₄H₉ |
| 2490 | CH₃ | O-t-C₄H₉ | t-C₄H₉ |
| 2491 | CH₃ | O-t-C₄H₉ | n-C₆H₁₃ |
| 2492 | CH₃ | O-t-C₄H₉ | Prop-1-en-3-yl |
| 2493 | CH₃ | O-t-C₄H₉ | (E)-1-Chloroprop-1-en-3-yl |
| 2494 | CH₃ | O-t-C₄H₉ | Propyn-3-yl |
| 2495 | CH₃ | O-t-C₄H₉ | 3-Methylbut-2-en-1-yl |

The compounds I are suitable as fungicides.

The compounds I are distinguished by an outstanding activity against a broad spectrum of phytopathogenic fungi, in particular from the Ascomycetes and Basidiomycetes classes. They are systemically active in some cases and can be employed as foliar and soil fungicides.

They are of particular importance for the control of a multiplicity of fungi on various crop plants such as wheat, rye, barley, oats, rice, corn, grass, cotton, soybeans, coffee, sugar cane, grapes, fruit and decorative plants and vegetable plants such as cucumbers, beans and cucurbits, and on the seeds of these plants.

They are specifically suitable for the control of the following plant diseases:

Erysiphe graminis (powdery mildew) in cereals, Erysiphe cichoracearum and Sphaerotheca fuliginea on cucurbits, Podosphaera leucotricha on apples, Uncinula necator on vines, Puccinia species on cereals, Rhizoctonia species on cotton and grass, Ustilago species on cereals and sugar cane, Venturia inaequalis (scab) on apples, Helminthosporium species on cereals, Septoria nodorum on wheat, Botrytis cinerea (gray mold) on strawberries, vines, Cercospora arachidicola on groundnuts, Pseudocercosporella herpotrichoides on wheat, barley, Pyricularia oryzae on rice, Phytophthora infestans on potatoes and tomatoes, Fusarium and Verticillium species on various plants, Plasmopara viticola on vines, Alternaria species on vegetables and fruit.

The compounds I are applied by treating the fungi or the plants, seeds, materials or the soil to be protected from fungal attack with a fungicidally effective amount of the active compounds. They are applied before or after the infection of the materials, plants or seeds by the fungi.

They can be converted into the customary formulations, such as solutions, emulsions, suspensions, dusts, powders, pastes and granules. The application form depends on the particular intended use; they should in any case guarantee a fine and uniform dispersion of the ortho-substituted benzyl ester of a cyclopropanecarboxylic acid [sic]. The formulations are prepared in a known manner, eg. by extending the active compound with solvents and/or carriers, if desired using emulsifiers and dispersants, it also being possible to use other organic solvents as auxiliary solvents when water is used as a diluent. Suitable auxiliary substances for this purpose are essentially: solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water; carriers such as ground natural minerals (eg. kaolins, argillaceous earths, talc, chalk) and ground synthetic minerals (eg. highly disperse silicic acid, silicates); emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

The fungicidal compositions in general contain from 0.1 to 95, preferably from 0.5 to 90%, by weight of active compound.

Depending on the type of effect desired, the application rates are from 0.01 to 2.0 kg of active compound per ha.

In seed treatment, active compound amounts of from 0.001 to 0.1 g, preferably 0.01 to 0.05 g, per kilogram of seed are in general needed.

The compositions according to the invention, in the application form as fungicides, can also be present together with other active compounds, the [sic] eg. with herbicides, insecticides, growth regulators, fungicides or alternatively with fertilizers.

On mixing with fungicides, in many cases an increase in the fungicidal spectrum of action is obtained here.

The following list of fungicides with which the compounds according to the invention can be applied together should illustrate the combination possibilities, but not restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediamine bisdithiocarbamate, tetramethylthiuram disulfides [sic], ammonia complex of zinc (N,N-ethylenebisdithiocarbamate), ammonia complex of zinc (N,N'-propylenebisdithiocarbamate), zinc (N,N'-propylenebisdithiocarbamate), N,N-polypropylenebis(thiocarbamoyl) disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropylcarbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino) phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazole carbamate, 2-methoxycarbonylaminobenzimidazole, 2-(fur-2-yl) benzimidazole, 2-(thiazol-4-yl)benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfadiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thio-1-oxide [sic], 8-hydroxyquinoline or its copper salt, 2,3-dihydro-5-carboxanilido-6-methyl-1,4-oxathiin, 2,3-dihydro-5-carboxanilido-6-methyl-1,4-oxathiin-4,4-dioxide, 2-methyl-5,6dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(1-(2,2,2-trichloroethyl)formamide [sic], 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol -1-yl)-2-butanol, α-(2-chlorophenyl)-α-(4-chlorophenyl)-5-pyrimidinemethnol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and also various fungicides, such as dodecylguanidine acetate, 3-[3-(3,5-dimethyl-2-oxycyclohexyl)-2-hydroxyethyl]glutarimide, hexachlorobenzene, DL-methyl-N-(2,6-dimethylphenyl)-N-2-furoyl alaninate, DL-N-(2,6-dimethylphenyl)-N-(2'- methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(-5-methyl-5-methoxymethyl]-1,3-oxazolidine-2,4-dione [sic], 3-(3,5-dichlorophenyl)-1-isopropylcarbamoylhydantoin, N-(3,5-dichlorophenyl)-1,2-dimethylcyclopropane-1,2-dicarboximide, 2-cyano-[N-ethyl-aminocarbonyl-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

The compounds of the formula I are additionally suitable to control pests from the class of insects, arachnids and nematodes effectively. They can be employed as pesticides in plant protection and in the hygiene, stored products protection and veterinary sectors.

The harmful insects include from the order of the butterflies (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus* [sic] *sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.*

From the order of the dipterous insects (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina* [sic]*, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterous insects (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the bugs (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the plant-sucking insects (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterous insects (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, spiders (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotet-*

*ranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root gall nematodes, eg. *Meloidogyne hapla, Meloidogyne incognita, Meloidogyne javanica*, cyst-forming nematodes, eg. *Globodera rostochiensis, Heterodera avenae, Heterodera glycines, Heterodera schachtii, Heterodera trifolii*, stem and leaf eelworms, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active compounds can be applied as such or in the form of their formulations or the application forms prepared therefrom, eg. in the form of directly sprayable solutions, powders, suspensions or dispersions, emulsions, oil dispersions, pastes, dusts, broadcasting compositions or granules by spraying, atomizing, dusting, broadcasting or pouring. The application forms depend entirely on the purposes of use; they should in any case as far as possible guarantee the finest dispersion of the active compounds according to the invention.

The active compound concentrations in the ready-for-application preparations can be varied within substantial ranges.

In general, they are from 0.0001 to 10%, preferably from 0.01 to 1%.

The active compounds can also be used with success in ultra-low volume processes (ULV), where it is possible to apply formulations containing more than 95% by weight of active compound or even the active compound without additives.

The application rate of active compound for controlling pests under outdoor conditions is from 0.1 to 2.0, preferably from 0.2 to 1.0 kg/ha.

For the preparation of directly sprayable solutions, emulsions, pastes or oil dispersions, mineral oil fractions of medium to high boiling point, such as kerosene or diesel oil, and also coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water are suitable.

Aqueous application forms can be prepared from emulsion concentrates, pastes or wettable powders (oil dispersions) by addition of water. For the preparation of emulsions, pastes or oil dispersions, the substances can be homogenized in water as such or dissolved in an oil or solvent, by means of wetting agents, adherents, dispersants or emulsifiers. However, concentrates consisting of active substance, wetting agent, adherent, dispersant or emulsifier and possibly solvent or oil can also be prepared, which are suitable for dilution with water.

Suitable surface-active substances are alkali metal, alkaline earth metal and ammonium salts of lignosulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and their alkali metal and alkaline earth metal salts, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenol ether, ethoxylated isooctylphenol, octylphenol, nonylphenol, alkylphenol polyglycol ether, tributylphenyl polyglycol ether, alkylaryl polyether alcohols, isotridecyl alcohol, fatty alcohol ethylene oxide condensates, ethoxylated castor oil, polyoxyethylene alkyl ether, ethoxylated polyoxypropylene, lauryl alcohol polyglycol ether acetal, sorbitol esters, lignin-sulfite waste liquors and methylcellulose.

Powders, scattering compositions and dusts can be prepared by mixing or joint grinding of the active substances with a solid carrier.

The formulations in general contain from 0.01 to 95% by weight, preferably from 0.1 to 90% by weight, of the active compound. The active compounds are employed here in a purity of from 90% to 100%, preferably 95% to 100% (according to NMR spectrum).

Examples of formulations are:

I. 5 parts by weight of a compound according to the invention are intimately mixed with 95 parts by weight of finely divided kaolin. A dust which contains 5% by weight of the active compound is obtained in this way.

II. 30 parts by weight of a compound according to the invention are intimately mixed with a mixture of 92 parts by weight of powdered silica gel and 8 parts by weight of paraffin oil which has been sprayed onto the surface of this silica gel. A preparation of the active compound having good adhesion is obtained in this way (active compound content 23% by weight).

III. 10 parts by weight of a compound according to the invention are dissolved in a mixture which consists of 90 parts by weight of xylene, 6 parts by weight of the addition product of 8 to 10 mol of ethylene oxide to 1 mol of oleic acid N-monoethanolamide, 2 parts by weight of calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture which consists of 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound according to the invention are well mixed with 3 parts by weight of the sodium salt of diisobutylnaphthalene-alpha-sulfonic acid, parts by weight of the sodium salt of a lignosulfonic acid from a sulfite waste liquor and 7 parts by weight of powdered silica gel and the mixture is ground in a hammer mill (active compound content 80% by weight).

VI. 90 parts by weight of a compound according to the invention are mixed with 10 parts by weight of N-methyl-α-pyrrolidone and a solution is obtained which is suitable for application in the form of very small drops (active compound content 90% by weight).

VII. 20 parts by weight of a compound according to the invention are dissolved in a mixture which consists of 40 parts by weight of cyclohexanone, 30 parts by weight of isobutanol, 20 parts by weight of the addition product of 7 mol of ethylene oxide to 1 mol of isooctylphenol and parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

VIII. 20 parts by weight of a compound according to the invention are well mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray liquor is obtained which contains 0.1% by weight of the active compound.

Granules, eg. coated, impregnated and homogeneous granules, can be produced by binding the active compounds to solid carriers. Solid carriers are eg. mineral earths, such as silica gel, silicic acids, silica gels [sic], silicates, talc, kaolin, attapulgite, limestone, lime, chalk, bole, loess, clay, dolomite, diatomaceous earth, calcium sulfate and magnesium sulfate, magnesium oxide, ground synthetic materials, fertilizers, such as eg. ammonium sulfate, ammonium phosphate, ammonium nitrate, ureas and vegetable products, such as grain meal, tree bark, wood and nutshell meal, cellulose powder and other solid carriers.

Oils of various types, herbicides, fungicides, other pesticides and bactericides can be added to the active compounds, if appropriate also just immediately before application (tank-mix). These agents can be admixed to the compositions according to the invention in the weight ratio 1:10–10:1.

SYNTHESIS EXAMPLES

The procedure described in the synthesis examples below are utilized with appropriate modification of the starting compounds to obtain further compounds I. The compounds thus obtained are shown in the following table with physical data.

1. Methyl N-methoxy-N-(2-(1'-methyl-1'-methoximino-1"-phenyl-iminoxymethylphenyl)carbamate [sic]

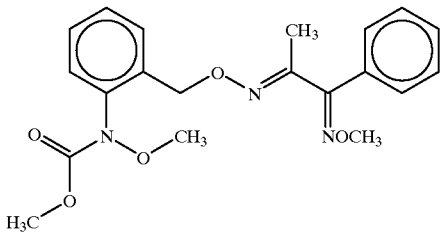

a) Methyl N-methoxy-N-(2-(1'-methyl-1'-benzoyl)iminoxymethylphenyl)carbamate

A mixture of g (0.15 ml) of a-hydroximinopropiophenoneoxime, 42 g (0.12 ml) of methyl N-(2-bromomethylphenyl)-N-methoxycarbamate (WO 93/15046; purity about 80%) and 42.3 g (0.3 mol) of $K_2CO_3$ in 100 ml of dimethylformamide is stirred overnight at room temperature. The reaction mixture is then diluted with water and the aqueous phase is extracted three times with methyl t-butyl ether. The combined organic phases are extracted once with water, dried over $MgSO_4$ and concentrated. The residue is purified by column chromatography using cyclohexane/ethyl acetate mixtures. 30 g (70%) of the title compound are obtained as a pale yellow oil.

$^1$H-NMR (CDCl$_3$; δ in ppm): 7.75 (d,1H,phenyl); 7.4 (m,8H,phenyl); 5.3 (s,2H,OCH$_2$); 3.7 (s,3H,OCH$_3$); 3.6 (s,3H,OCH$_3$); 2.2 (s,3H,CH$_3$)

b) Methyl N-methoxy-N-(2-(1'-methyl-1'-methoximino-1"-phenyl)iminoxymethylphenyl)carbamate

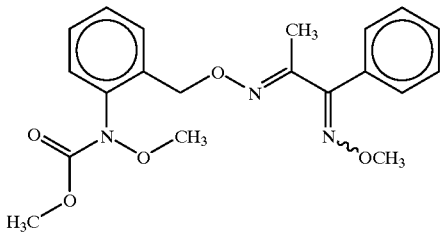

A mixture of 0.8 g (10 ml) of methoxyamine hydrochloride, 0.9 g (12 mol) of pyridine and 3 g of the ketone from Example 1a in 15 ml of methanol is stirred at room temperature for 3 days. The reaction mixture is then diluted with water and the aqueous phase is extracted three times with methylene chloride. The combined organic phases are extracted with dilute hydrochloric acid solution and water, dried over MgSO$_4$ and concentrated. As a residue, 1.5 g (47%) of the title compound (2 isomers, about 2:1) are obtained as a yellow oil.

$^1$H-NMR (CDCl$_3$; δ in ppm): Isomer A (larger amount): 5.25 (s,2H,OCH$_2$); 4.0 (s,3H,OCH$_3$); 3.70 (s,3H,OCH$_3$); 3.6 (s,3H,OCH$_3$); 2.15 (s,3H,CH$_3$) Isomer B (smaller amount): 5.05 (s,2H,OCH$_2$); 3.9 (s,3H,OCH$_3$); 3.68 (s,3H,OCH$_3$); 3.45 (s,3H,OCH$_3$); 2.2 (s,3H,CH$_3$)

The signals of the aromatic protons of the two isomers are not resolved: 7.5 (d,broad); 7.2–7.4 (m); 7.15 (m)

2. N-Methyl-N'-methoxy-N'-(2-(1'-methyl-1'-methoximino-1"-ethyl)iminoxymethylphenyl)urea

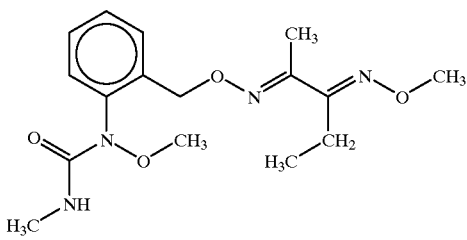

a) N-Methyl-N'-methoxy-N'-(2-(1'-methyl-1'-propionyl)iminoxymethylphenyl)urea

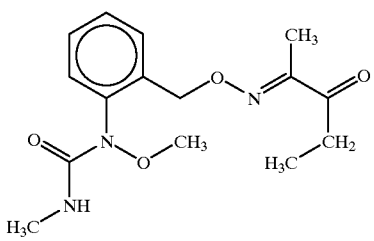

A mixture of 1.9 g (16 mmol) of a-hydroximino-3-pentanone, 5 g (15 mmol) of phenyl N-methoxy-N-(2-bromomethylphenyl)carbamate (prepared similarly to WO 93/15046) and 4.1 g (30 mmol) of K$_2$CO$_3$ in 20 ml of dimethylformamide is stirred overnight at room temperature. The reaction mixture is then diluted with water and the aqueous phase is extracted three times with methyl t-butyl ether. The combined organic phases are dried over $MgSO_4$, filtered with suction through $Al_2O_3$ and concentrated.

The residue is treated with 20 ml of 40% strength aqueous methylamine solution and stirred overnight at room temperature.

The reaction mixture is then extracted three times with methyl t-butyl ether. The combined organic phases are extracted once with water, dried over $MgSO_4$ and concentrated. The residue is purified by column chromatography using cyclohexane/ethyl acetate mixtures. 2.7 g (59%) of the title compound are obtained as a pale yellow oil.

$^1$H-NMR (CDCl$_3$; δ in ppm): 7.45 (m,1H,phenyl); 7.35 (m,3H,phenyl); 6.1 (s,broad,1H,NH); 5.4 (s,2H,OCH$_2$); 3.7 (s,3H,OCH$_3$); 2.9 (d,3H,N—CH$_3$); 2.8 (q,2H,CH$_2$—CH$_3$); 2.0 (s,3H,CH$_3$); 1.1 (t,3H,CH$_2$—CH$_3$)

b) N-Methyl-N'-methoxy-N'-(2-(1'-methyl-1'-methoximino-1"-ethyl)iminoxymethylphenyl)urea

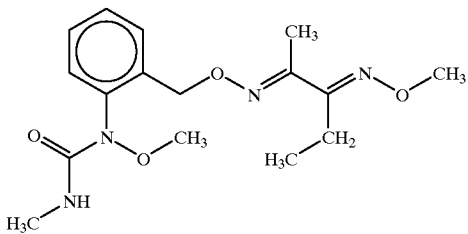

A mixture of 2.7 g (8.8 mmol) of the ketone from Example 2a and 1.5 g (18 mmol) of methoxy amine.HCl [sic] in 15 ml of methanol is stirred overnight at room temperature. The reaction mixture is then diluted with water and the aqueous phase is extracted three times with methyl t-butyl ether. The combined organic phases are extracted once with water, dried over $MgSO_4$ and concentrated. The residue crystallizes and is is [sic] washed with hexane with stirring. 1.5 g (51%) of the title compound are obtained as colorless crystals (m.p.=92° C.).

$^1$H-NMR (CDCl$_3$; δ in ppm): 7.45 (m,1H,phenyl); 7.3 (m,3H,phenyl); 6.0 (s,broad,1H,NH); 5.3 (s,2H,O—CH$_2$); 3.95 (s,3H,OCH$_3$); 3.7 (s,3H,OCH$_3$); 2.9 (d,3H,N—CH$_3$); 2.5 (q,2H,CH$_2$—CH$_3$); 2.05 (s,3H,CH$_3$); 0.95 (t,3H,CH$_2$—CH$_3$)

TABLE I

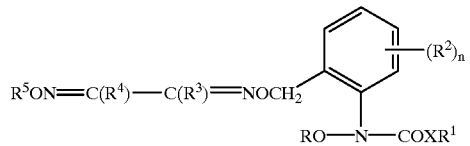

| No | X | R | $R^1$ | $R_n^2$ | $R^3$ | $R^4$ | $R^5$ | M.p. [° C.]; IR [cm$^{-1}$] |
|---|---|---|---|---|---|---|---|---|
| 01 | O | CH$_3$ | CH$_3$ | H | CH$_3$ | C$_6$H$_5$ | CH$_3$ | 1739, 1711, 1456, 1442, 1342, 1101, 1055, 1034, 767, 694 (EE:ZE = 1:2) |
| 02 | O | CH$_3$ | CH$_3$ | H | CH$_3$ | C$_6$H$_5$ | C$_2$H$_5$ | 1749, 1711, 1456, 1442, 1357, 1092, 1035, 987, 927, 767 |
| 03 | O | CH$_3$ | CH$_3$ | H | CH$_3$ | C$_6$H$_5$ | (CH$_2$)$_2$CH$_3$ | 1740, 1712, 1456, 1442, 1343, 1098, 1067, 1027, 989, 767 |
| 04 | O | CH$_3$ | CH$_3$ | H | CH$_3$ | C$_6$H$_5$ | CH(CH$_3$)$_2$ | 1740, 1712, 1456, 1442, 1349, 1342, 1327, 1121, 1028, 975 |
| 05 | O | CH$_3$ | CH$_3$ | H | CH$_3$ | C$_6$H$_5$ | (CH$_2$)$_3$CH$_3$ | 1740, 1712, 1456, 1442, 1361, 1029, 1016, 978 |
| 06 | O | CH$_3$ | CH$_3$ | H | CH$_3$ | CH$_3$ | CH$_3$ | 76 |
| 07 | O | CH$_3$ | CH$_3$ | H | CH$_3$ | CH$_3$ | C$_2$H$_5$ | 76 |
| 08 | O | CH$_3$ | CH$_3$ | H | CH$_3$ | CH$_3$ | (CH$_2$)$_2$CH$_3$ | 2965, 1742, 1456, 1440, 1365, 1341, 1046, 1020, 990, 927 |
| 09 | O | CH$_3$ | CH$_3$ | H | CH$_3$ | C$_2$H$_5$ | CH$_3$ | 1741, 1456, 1441, 1359, 1337, 1100, 1051, 1030, 893, 877 |
| 10 | O | CH$_3$ | CH$_3$ | H | CH$_3$ | C$_2$H$_5$ | C$_2$H$_5$ | 66 |
| 11 | O | CH$_3$ | CH$_3$ | H | CH$_3$ | C$_2$H$_5$ | (CH$_2$)$_2$CH$_3$ | 2968, 2936, 1742, 1456, 1440, 1359, 1341, 1027, 991, 959 |

TABLE-continued

I $R^5ON=C(R^4)-C(R^3)=NOCH_2$ — [phenyl with $(R^2)_n$ and $RO-N-COXR^1$ substituents]

| No | X | R | R¹ | R$_n^2$ | R³ | R⁴ | R⁵ | M.p. [° C.]; IR [cm⁻¹] |
|----|---|-----|-----|---|-----|--------------------|----------|-------------------------|
| 12 | O | CH₃ | CH₃ | H | CH₃ | CH(CH₃)2 | CH₃ | 1741, 1456, 1441, 1350, 1251, 1097, 1048, 1029, 1014 |
| 13 | O | CH₃ | CH₃ | H | CH₃ | 4-OCH₃—C₆H₄ | CH₃ | 1738, 1710, 1608, 1512, 1456, 1441, 1343, 1252, 1175, 1033 |
| 14 | O | CH₃ | CH₃ | H | CH₃ | 4-Cl—C₆H₄ | C₂H₅ | 1740, 1711, 1491, 1456, 1440, 1357, 1092, 1051, 1031, 1013 |
| 15 | O | CH₃ | CH₃ | H | CH₃ | 4-F—C₆H₄ | CH₃ | 1739, 1711, 1509, 1456, 1441, 1341, 1226, 1052, 1035, 1013 |
| 16 | NH | CH₃ | CH₃ | H | CH₃ | C₂H₅ | CH₃ | 92 |
| 17 | O | CH₃ | CH₃ | H | CH₃ | 4-CH₃—C₆H₄ | CH₃ | 1739, 1711, 1456, 1440, 1340, 1101, 1067, 1051, 1030, 1013 |
| 18 | O | CH₃ | CH₃ | H | CH₃ | 4-OCH₃—C₆H₄ | C₂H₅ | 1739, 1711, 1512, 1456, 1441, 1356, 1343, 1252, 1176, 1034 |
| 19 | O | CH₃ | CH₃ | H | CH₃ | 4-Cl—C₆H₄ | CH₃ | 1739, 1711, 1491, 1456, 1440, 1339, 1092, 1051, 1034, 1013 |
| 20 | O | CH₃ | CH₃ | H | CH₃ | 4-CH₃—C₆H₄ | C₂H₅ | 1740, 1731, 1439, 1318, 1264, 1102, 1003, 968, 862, 761 |
| 21 | O | CH₃ | CH₃ | H | CH₃ | 4-F—C₆H₄ | C₂H₅ | 1740, 1711, 1509, 1441, 1357, 1340, 1227, 1051, 1033, 1014 |
| 22 | O | CH₃ | CH₃ | H | CH₃ | 4-Br-C₆H₄ | C₂H₅ | 1739, 1711, 1487, 1456, 1440, 1356, 1071, 1054, 1009, 979 |
| 23 | O | CH₃ | CH₃ | H | CH₃ | C₆H₅ | CH₃ | 65 (E:E) |
| 24 | O | CH₃ | CH₃ | H | CH₃ | 4-Br—C₆H₄ | CH₃ | 1739, 1711, 1488, 1456, 1440, 1338, 1072, 1050, 1032, 1009 |
| 25 | O | CH₃ | CH₃ | H | CH₃ | CN | CH₃ | 1739, 1711, 1456, 1441, 1357, 1248, 1109, 1064, 1020, 890 |
| 26 | O | CH₃ | CH₃ | H | CH₃ | CONH₂ | CH₃ | 1738, 1710, 1456, 1441, 1356, 1089, 1046, 991, 886, 766 |
| 27 | O | CH₃ | CH₃ | H | CH₃ | 3-CF₃—C₆H₄ | CH₂C≡CH | 1736, 1441, 1335, 1325, 1250, 1168, 1127, 1099, 1074, 1007 |
| 28 | O | CH₃ | CH₃ | H | CH₃ | 4-CF₃—C₆H₄ | CH₂C≡CH | 1738, 1441, 1326, 1271, 1168, 1126, 1112, 1069, 1060, 1006 |
| 29 | O | CH₃ | CH₃ | H | CH₃ | 4-CH(CH₃)₂—C₆H₄ | CH₂C≡CH | 2960, 1738, 1711, 1456, 1440, 1354, 1257, 1101, 1027, 1007 |
| 30 | O | CH₃ | CH₃ | H | CH₃ | 4-C(CH₃)₃—C₆H₄ | CH₂C≡CH | 2962, 1739, 1456, |

TABLE-continued $$R^5ON{=}C(R^4){-}C(R^3){=}NOCH_2{-}\underset{\underset{RO-N-COXR^1}{}}{C_6H_3(R^2)_n}$$

I

| No | X | R | $R^1$ | $R_n^2$ | $R^3$ | $R^4$ | $R^5$ | M.p. [° C.]; IR [cm$^{-1}$] |
|---|---|---|---|---|---|---|---|---|
| 31 | O | CH$_3$ | CH$_3$ | H | CH$_3$ | 3,5-Cl$_2$—C$_6$H$_3$ | CH$_2$C≡CH | 1440, 1362, 1351, 1267, 1109, 1027, 1007 1738, 1562, 1456, 1440, 1354, 1259, 1102, 1006, 993, 764 |
| 32 | O | CH$_3$ | CH$_3$ | H | OC$_2$H$_5$ | CH$_3$ | CH$_3$ | 1740, 1456, 1441, 1366, 1343, 1251, 1144, 1105, 1059, 1027 |
| 33 | O | CH$_3$ | CH$_3$ | H | SCH$_3$ | CH$_3$ | CH$_3$ | 1739, 1711, 1456, 1440, 1337, 1102, 1049, 1022, 988, 878 |

Examples of the Action Against Harmful Fungi

It was possible to show the fungicidal action of the compounds of the general formula I by the following tests:

The active compounds were prepared as a 20% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight Emulphor® EL (Emulan® EL, emulsifier based on ethoxylated fatty alcohols) and diluted with water according to the concentration desired.

Action Against *Pyricularia oryzae* (rice blast)

Rice seedlings (variety: Tai Nong 67) were sprayed with the active compound preparation until dripping wet. After 24 hours, the plants were sprayed with an aqueous spore suspension of the fungus *Pyricularia oryzae* and kept for 6 days at from 22 to 24° C. and a relative atmospheric humidity of from 95 to 99%. Assessment was carried out visually.

In this test, the plants treated with 63 ppm of the compounds 01 to 07 according to the invention showed an attack of 15% or less while the untreated plants were attacked to 60%.

In a corresponding test, the plants treated with 63 ppm of the compounds 08 to 15, 17, 19 and 21 to 24 according to the invention showed an attack of 15% or less, while the untreated plants were attacked to 60%.

Action Against *Puccinia recondita* (brown rust of wheat)

Leaves of wheat seedlings (Kanzler variety) were dusted with spores of brown rust ((*Puccinia recondita*). The plants treated in this way were incubated for 24 h at from 20 to 22° C. and a relative atmospheric humidity of from 90 to 95% and then treated with the aqueous active compound preparation. After a further 8 days at from 20 to 22° C. and 65–70% relative atmospheric humidity, the extent of fungal development was determined. Assessment was carried out visually.

In this test, the plants treated with 250 ppm of the compounds 01 to 05 and 07 according to the invention showed an attack of 15% or less, while the untreated plants were attacked to 70%.

In a corresponding test, the plants treated with 250 ppm of the compounds 08 to 15 and 17 to 24 according to the invention showed an attack of 5% or less, while the untreated plants were attacked to 70%.

Examples of the Action Against Animal Pests

It was possible to show the insecticidal action of the compounds of the general formula I by the following tests:

The active compounds were prepared a) as a 0.1% strength solution in acetone or b) as a 10% strength emulsion in a mixture of 70% by weight of cyclohexanol, 20% by weight of Nekanil® LN (Lutensol® AP6, wetting agent having emulsifier and dispersant action based on ethoxylated alkylphenols) and 10% by weight of Emulphor® EL, [lacuna] emulsifier based on ethoxylated fatty alcohols) and diluted with acetone in the case of a) or with water in the case of b) according to the desired concentration.

After conclusion of the tests, the lowest concentration at which the compounds still caused an 80–100% inhibition or mortality in comparison with untreated control tests [sic] was determined in each case (activity threshold or minimum concentration).

We claim:

1. An iminooxymethylenanilide of the formula I

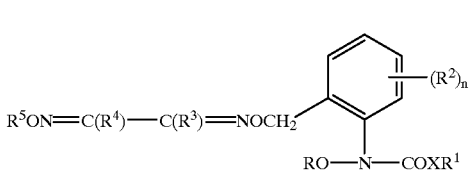

where the substituents and the index have the following meanings:

R is hydrogen,
  unsubst. or subst. alkyl, alkenyl, alkynyl, cycloalkyl, cycloalkenyl, cycloalkynyl, alkylcarbonyl or alkoxycarbonyl;

$R^1$ is alkyl, alkenyl, alkynyl, cycloalkyl or cycloalkenyl and in the case where X is NR$^a$, additionally hydrogen;

X is a direct bond, O or NR$^a$;

R$^a$ is hydrogen, alkyl, alkenyl, alkynyl, cycloalkyl or cycloalkenyl;

R$^2$ is cyano, nitro, trifluoromethyl, halogen, $C_1$–$C_4$-alkyl or $C_1$–$C_4$-alkoxy;

n is 0, 1 or 2, it being possible for the radicals R$^2$ to be different id n is 2;

R$^3$ is hydrogen, hydroxyl, cyano, cyclopropyl, trifluoromethyl, halogen, $C_1$–$C_6$-alkyl, $C_1$–$C_6$-alkoxy or $C_1$–$C_6$-alkylthio;

R$^4$ is hydrogen, cyano, nitro, hydroxyl, amino, halogen, $C_1$–$C_6$-alkyl, $C_1$–$C_6$-alkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkenylthio, $C_2$–$C_6$-alkenylamino, N-$C_2$–$C_6$-alkenyl-N-$C_1$–$C_6$-alkylamino, $C_2$–$C_6$-alkynyl, $C_2$–$C_6$-alkynyloxy, $C_2$–$C_6$-alkynylthio, $C_2$–$C_6$-alkynylamino, N-$C_2$–$C_6$-alkynyl-N-$C_1$–$C_6$-alkylamino, it being possible for the hydrocarbon radicals of these groups to be partially or completely halogenated or to carry one to three of the following radicals: cyano, nitro, hydroxyl, mercapto, amino, carboxyl, aminocarbonyl, aminothiocarbonyl, halogen, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkoxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio, hetaryl-$C_1$–$C_4$-alkylthio, it being possible for the cyclic radicals in turn to be partially or completely halogenated and/or to carry one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and C(=NOR$^6$)—A$_n$—R$^7$;

$C_3$–$C_6$-cycloalkyl, $C_3$–$C_6$-cycloalkoxy, $C_3$–$C_6$-cycloalkylthio, $C_3$–$C_6$-cycloalkylamino, N-$C_3$–$C_6$-cycloalkyl-N-$C_1$–$C_6$-alkylamino, $C_3$–$C_6$-cycloalkenyl, $C_3$–$C_6$-cycloalkenyloxy, $C_3$–$C_6$-cycloalkenylthio, $C_3$–$C_6$-cycloalkenylamino, N-$C_3$–$C_6$-cycloalkenyl-N-$C_1$–$C_6$-alkylamino, heterocyclyl, heterocyclyloxy, heterocyclylthio, heterocyclylamino, N-heterocyclyl-N-$C_1$–$C_6$-alkylamino, aryl, aryloxy, arylthio, arylamino, N-aryl-N-$C_1$–$C_6$-alkylamino, hetaryl, hetaryloxy, hetarylthio, hetarylamino, N-hetaryl-N-$C_1$–$C_6$-alkylamino, it being possible for the cyclic radicals to be partially or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl and hetaryloxy;

R$^5$ is hydrogen,
$C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_1$–$C_{10}$-alkenylcarbonyl, $C_1$–$C_{10}$-alkynylcarbonyl or $C_1$–$C_{10}$-alkylsulfonyl, it being possible for these radicals to be partially or completely halogenated or to carry one to three of the following groups: cyano, nitro, hydroxy, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkoxy, heterocyclyl, heterocyclyloxy, benzyl, benzyloxy, aryl, aryloxy, arylthio, hetaryl, hetaryloxy and hetarylthio, it being possible for the cyclic groups in turn to be partially or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and C(=NOR$^6$)—A$_n$—R$^7$; aryl, arylcarbonyl, arylsulfonyl, hetaryl, hetarylcarbonyl or hetarylsulfonyl, it being possible for these radicals to be partially or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy or C(=NOR$^6$)—A$_n$—R$^7$;

A being oxygen, sulfur or nitrogen and the nitrogen carrying hydrogen or $C_1$–$C_6$-alkyl;

m being 0 or 1;

R$^6$ being hydrogen, $C_1$–$C_6$-alkyl, $C_2$–$C_6$-alkenyl or $C_2$–$C_6$-alkynyl and $R^7$ being hydrogen, $C_1$–$C_6$-alkyl, $C_2$–$C_6$-alkenyl or $C_2$–$C_6$-alkynyl, or its salts.

2. The compound of the formula I as defined in claim 1, where n is 0.

3. The compound of the formula I as defined in claim 1, where $R^1$ is methyl.

4. A process for preparing a compound of the formula I as defined in claim 1, where R is not hydrogen and $R^3$ is not halogen, which comprises reacting a benzyl derivative of the formula II

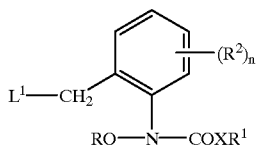  (II)

where $L^1$ is a nucleophilically replaceable leaving group, with an oxime of the formula III $R^5ON=C(R^4)—C(R^3)=NOH$   (III).

5. A process for preparing a compound of the formula I as defined in claim 1, where R is not hydrogen and $R^3$ and $R^4$ are not halogen, which comprises reacting a benzyl derivative of the formula II

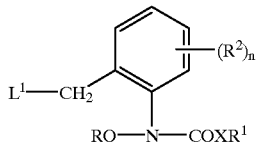  (II)

where $L^1$ is a nucleophilically replaceable leaving group, with a dioxime of the formula IV $HON=C(R^4)—C(R^3)=NOH$   (IV)

to give a compound of the formula V

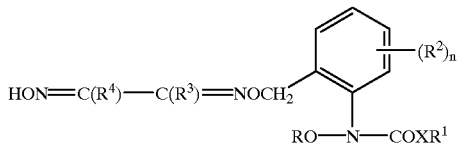  (V)

and reacting V with a compound of the formula VI $R^5—L^2$   (VI)

where $L^2$ a nucleophilically replaceable leaving group, to give I.

6. A process for preparing a compound of the formula I as defined in claim 1, where $R^3$ is not halogen, which comprises reacting a benzyl derivative of the formula II

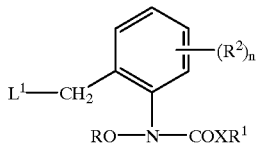  (II)

where $L^1$ is a nucleophilically replaceable leaving group, with a ketoxime of the formula VII $O=C(R^4)—C(R^3)=NOH$   (VII)

to give a compound of the formula VIII

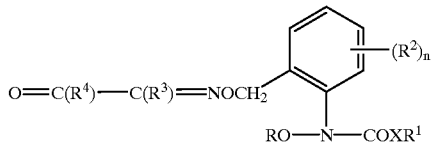  (VIII)

then reacting VIII either a) first with hydroxylamine or its salt and then with a compound of the formula $R^5—L^2$ where $L^2$ is a nucleophilically replaceable leaving group or b) with a hydroxylamine or a hydroxylammonium salt of the formula IXa or IXb $R^5—ONH_2$   (IXa)

$R^5—ONH_3^\oplus\ Q^\ominus$   (IXb)

where $Q^\ominus$ is the anion of an acid, to give I.

7. A composition against animal pests or harmful fungi, containing customary additives and an effective amount of a compound of the formula I as defined in claim 1.

8. The composition defined in claim 7 for controlling animal pests of the insects, arachnids or nematodes class.

9. A method for controlling animal pests or harmful fungi, which comprises treating the pests or harmful fungi, their habitat or the plants, surfaces, materials or spaces to be kept free from them with an effective amount of a compound of the formula I as defined in claim 1.

10. The use of the compounds I as claimed in claim 1 for preparing compositions against animal pests or harmful fungi.

11. The use of the compounds I as claimed in claim 1 for controlling animal pests or harmful fungi.

12. The compound of the formula VIII as defined in claim 6.

13. The use of the compounds of the formula VIII as given in claim 6 as intermediates.

14. A compound of the formula X

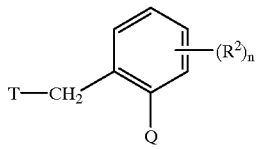

(X)

where the index and the substituents have the following meanings:

Q is $NO_2$, HNOH or $N(OR)-CO_2C_6H_5$;

T is $O=C(R^4)-C(R^3)=NO-$, $HON=C(R^4)-C(R^3)=NO-$ or $R^5ON=C(R^4)-C(R^3)=NO-$, the substituents R, $R^2$, $R^3$, $R^4$ and $R^5$ and the index n having the meanings set forth in claim 1.

15. The use of the compounds of the formula X as claimed in claim 14 as intermediates.

16. A compound of the formula XI

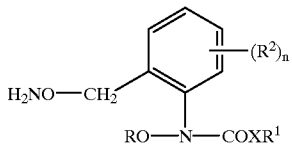

(XI)

where the index n and the substituents R, $R^1$ and $R^2$ have the meanings set forth in claim 1.

17. The use of the compounds of the formula XI as claimed in claim 16 as intermediates.

18. The compound of the formula I as defined in claim 1 where $R^4$ is aryl or hetaryl, it being possible for the cyclic radicals to be partially or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl and hetaryloxy; and $R^5$ is hydrogen, $C_1$–$C_{10}$-alkyl, $C_2$–$C_{10}$-alkenyl or $C_2$–$C_{10}$-alkynyl, it being possible for these radicals to be partially or completely halogenated.

19. The compound of the formula I as defined in claim 18 wherein $R^4$ is phenyl, it being possible for the phenyl radical to be partially or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-halocalkyl, $C_1$–$C_6$-alkylsulfonyl, $C_1$–$C_6$-alkylsulfoxyl, $C_3$–$C_6$-cloalkyl, $C_1$–$C_6$-alkoxy, $C_1$–$C_6$-haloalkoxy, $C_1$–$C_6$-alkoxycarbonyl $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkyaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl and hetaryloxy.

20. The compound of the formula I as defined in claim 18 wherein n is 0;

R, $R^1$, $R^3$ and $R^5$ are, independently of one another, $C_1$–$C_4$-alkyl,

X is oxygen, and $R^4$ is unsubstituted or partially or completely halogenated phenyl.

* * * * *

UNITED STATES PATENT AND TRADEMARK OFFICE
CERTIFICATE OF CORRECTION

PATENT NO.: 5,977,399

DATED: November 2, 1999

INVENTOR(S): MUELLER et al.

It is certified that error appears in the above-identified patent and that said Letters Patent is hereby corrected as shown below:

Col. 101, claim 5, line 63, after "$L^2$" insert --is--.

Col. 104, claim 19, line 23, "$C_3$-$C_6$-cloalkyl" should be --$C_3$-$C_6$-cycloalkyl--.

Signed and Sealed this

Ninth Day of May, 2000

Attest:

Q. TODD DICKINSON

*Attesting Officer*  *Director of Patents and Trademarks*